(12) United States Patent
Warner

(10) Patent No.: US 12,020,872 B2
(45) Date of Patent: Jun. 25, 2024

(54) STILBENE AND FUSED STILBENE DERIVATIVES AS SOLAR CELL DYES

(71) Applicant: AMBIENT PHOTONICS, INC., Mill Valley, CA (US)

(72) Inventor: John C. Warner, Wilmington, MA (US)

(73) Assignee: AMBIENT PHOTONICS, INC., Scotts Valley, CA (US)

(*) Notice: Subject to any disclaimer, the term of this patent is extended or adjusted under 35 U.S.C. 154(b) by 0 days.

(21) Appl. No.: 18/156,925

(22) Filed: Jan. 19, 2023

(65) Prior Publication Data

US 2023/0154691 A1    May 18, 2023

Related U.S. Application Data

(62) Division of application No. 16/611,963, filed as application No. PCT/US2018/031489 on May 8, 2018, now Pat. No. 11,664,171.

(60) Provisional application No. 62/503,645, filed on May 9, 2017.

(51) Int. Cl.
| | |
|---|---|
| *H01G 9/20* | (2006.01) |
| *C07D 307/79* | (2006.01) |
| *C07D 307/81* | (2006.01) |
| *C09B 23/10* | (2006.01) |
| *C09B 23/14* | (2006.01) |
| *C09B 57/00* | (2006.01) |
| *H10K 85/60* | (2023.01) |
| *H10K 30/15* | (2023.01) |
| *H10K 102/10* | (2023.01) |

(52) U.S. Cl.
CPC ......... *H01G 9/2059* (2013.01); *C07D 307/79* (2013.01); *C07D 307/81* (2013.01); *C09B 23/105* (2013.01); *C09B 23/148* (2013.01); *C09B 57/008* (2013.01); *H10K 85/636* (2023.02); *H10K 30/151* (2023.02); *H10K 85/6574* (2023.02); *H10K 2102/102* (2023.02); *Y02E 10/542* (2013.01); *Y02E 10/549* (2013.01); *Y02P 70/50* (2015.11)

(58) Field of Classification Search
CPC .. C09B 23/148; C09B 23/105; H10K 85/636; H10K 85/6574
See application file for complete search history.

(56) References Cited

U.S. PATENT DOCUMENTS

| | | |
|---|---|---|
| 10,590,100 B2 | 3/2020 | Warner et al. |
| 11,286,233 B2 | 3/2022 | Warner |
| 2013/0074935 A1 | 3/2013 | Warner et al. |
| 2016/0190466 A1 | 6/2016 | Pfister et al. |
| 2021/0082632 A1 | 3/2021 | Warner |

FOREIGN PATENT DOCUMENTS

| | | |
|---|---|---|
| CN | 104649949 A | 5/2015 |
| EP | 2899799 A1 | 7/2015 |
| JP | 2009-187821 A | 8/2020 |
| WO | WO94/05025 A1 | 3/1994 |
| WO | WO2016/111636 A1 | 7/2016 |
| WO | WO2017/056053 A1 | 4/2017 |

OTHER PUBLICATIONS

International Search Report and Written Opinion for PCT Patent App. No. PCT/US2018/031489 (Sep. 10, 2018).
Pubchem, CID 3517936, Sep. 8, 2005, pp. 1-20, retrieved from the Internet <URL: https://pubchem.ncbi.nlm.nih.gov/compound/3517936>.
International Preliminary Report on Patentability for PCT Patent App. No. PCT/US2018/031489 (Nov. 21, 2019).
Raoui, M., et al., "Highly fluorescent extended 2-(2'-hydroxyphenyl)benzazole dyes: synthesis, optical properties and first-principle calculations," Chem. Commun. 2016;52:9216-9219.
Extended European Search Report for European Patent App. No. 18798831.6 (Feb. 16, 2021).

*Primary Examiner* — Anthony Ho
(74) *Attorney, Agent, or Firm* — Cermak & McGowan LLP; Malcolm K. McGowan

(57) ABSTRACT

The present application discloses stilbene derivative compounds and phenylbenzofuran compositions, useful in the manufacture of dye-sensitized solar cells and other similar technology.

14 Claims, No Drawings

STILBENE AND FUSED STILBENE DERIVATIVES AS SOLAR CELL DYES

CROSS-REFERENCE TO RELATED APPLICATIONS

This application is a divisional of U.S. application Ser. No. 16/611,63, filed 8 Nov. 2019, which is a national stage entry of PCT/US2018,031489, filed 8 May 2018, which claims priority from U.S. Provisional Application 62/503,645, filed 9 May 2017. The contents of these priority applications are incorporated herein by reference in their entirety.

TECHNICAL FIELD

The present invention is in the field of material compositions used to assemble dye sensitized solar cells (DSSC) and other dye sensitized electronic devices such as information storage devices, sensing devices and imaging devices. In particular, it concerns the utility of novel organic chromophores as the sensitizing dyes in dye sensitized electronic devices.

BACKGROUND

Sensitization of semiconductor solids such as metal oxides in imaging devices, memories, sensors, and solar cells can serve as an effective means of energy transduction. These devices use metal oxides, such as titanium dioxide that are transparent to light but can be sensitized to the desired spectrum through the use of sensitizing agents that absorb light energy and transduce it into electrical power or an electrical signal. This sensitization occurs through charge injection into the metal oxide from the excited state of the dye sensitizer. Sensitizers such as transition metal complexes, inorganic colloids and organic dye molecules are used.

Prominent among such technologies is the dye-sensitized metal oxide solar cell (DSSC). DSSCs use a dye to absorb light and initiate a rapid electron transfer to a nanostructured oxide such as $TiO_2$. The mesoscopic structure of the $TiO_2$ allows building of thick, nanoporous films with active-layer thicknesses of several microns. The dye is then adsorbed on the large surface area of the mesoporous $TiO_2$. Charge balance and transport is achieved by a layer having a REDOX couple, such as iodide/triiodide, Co(II)/Co(III) complexes, and Cu(I)/Cu(II) complexes.

Dyes based on transition metal complexes are disclosed in Gratzel et al., U.S. Pat. Nos. 4,927,721 and 5,350,644. These dye materials are disposed on mesoporous metal oxides that have a high surface area on which the absorbing, sensitizing layer can be formed. This results in a high absorptivity of light in the cell. Dyes such as Ru(II) (2,2'-bipyridyl 4,4' dicarboxylate)$_2$ (NCS)$_2$ have been found to be efficient sensitizers and can be attached to the metal oxide solid through carboxyl or phosphonate groups on the periphery of the compounds. However, when transition metal ruthenium complexes are used as sensitizers they must be applied to the mesoporous metal oxide layers in a coat as thick as 10 micrometers or thicker in order to absorb enough solar radiation to attain sufficient power conversion efficiencies. Further, the ruthenium complexes are expensive. In addition, such dyes must be applied using volatile organic solvents, co-solvents, and diluents because they are not dispersible in water. Volatile organic compounds (VOCs) are significant pollutants that can affect the environment and human health. While VOCs are usually not acutely toxic, they may have chronic health and environmental effects. For this reason, governments around the world are seeking to reduce the levels of VOCs.

One type of dye-sensitized solar cell is known as the Gratzel cell. Hamann et al., "Advancing beyond current generation dye-sensitized solar cells," (the disclosure of which is incorporated in its entirety by reference, hereinafter "Hamann") describes the Gratzel cell. The Gratzel cell includes crystalline titanium dioxide nanoparticles serving as a photoanode in the photovoltaic cell. The titanium dioxide is coated with light sensitive dyes. The titanium dioxide photoanode includes 10-20 nm diameter titanium dioxide particles forming a 12 μm transparent film. The 12 μm titanium dioxide film is made by sintering the 10-20 nm diameter titanium dioxide particles so that they have a high surface area. The titanium dioxide photoanode also includes a 4 μm film of titanium dioxide particles having a diameter of about 400 nm. The coated titanium dioxide films are located between two transparent conducting oxide (TCO) electrodes. Also disposed between the two TCO electrodes is an electrolyte with a redox shuttle.

The Gratzel cell may be made by first constructing a top portion. The top portion may be constructed by depositing fluorine-doped tin dioxide (SnO.sub.2F) on a transparent plate, which is usually glass. A thin layer of titanium dioxide ($TiO_2$) is deposited on the transparent plate having a conductive coating. The $TiO_2$ coated plate is then dipped into a photosensitized dye such as ruthenium-polypyridine dye in solution. A thin layer of the dye covalently bonds to the surface of the titanium dioxide. A bottom portion of the Gratzel cell is made from a conductive plate coated with platinum metal. The top portion and the bottom portion are then joined and sealed. The electrolyte, such as iodide-triiodide, is then typically inserted between the top and bottom portions of the Gratzel cell.

Typically, thin films for Dye Sensitized Solar Cells (DSSC) are composed of a single metal oxide—usually titanium dioxide, which in addition to nanoparticles, may be utilized in the form of larger 200 to 400 nm scale particles or as dispersed nanoparticles formed in-situ from a titanium alkoxide solution. In one embodiment, the present application discloses the use of multiple morphologies of titanium oxide as well as other metal oxides, which provide a boost in efficiency over the single metal oxide system. The additional metal oxides that may be employed include, but are not limited to, alpha aluminum oxide, gamma aluminum oxide, fumed silica, silica, diatomaceous earth, aluminum titanate, hydroxyapatite, calcium phosphate and iron titanate; and mixtures thereof. These materials may be utilized in conjunction with traditional titanium oxide thin films or with a thin film dye sensitized solar cell system as described in U.S. Provisional Patent Application No. 61/237,137, filed Aug. 26, 2009, entitled "Low Cost Thin Film for Dye Sensitized Solar Cells," the disclosure of which is incorporated herein by reference in its entirety.

In operation, the dye absorbs sunlight, which results in the dye molecules becoming excited and transmitting electrons into the titanium dioxide. The titanium dioxide accepts the energized electrons, which travel to a first TCO electrode. Concurrently, the second TCO electrode serves as a counter electrode, which uses a redox couple such as iodide-triiodide ($I_3^-$/$I^-$) to regenerate the dye. If the dye molecule is not reduced back to its original state, the oxidized dye molecule decomposes. As the dye-sensitized solar cell undergoes a large number of the oxidation-reduction cycles in the lifetime of operation, more and more dye molecules undergo decomposition over time, and the cell energy conversion efficiency decreases.

Hattori and his coworkers (S. Hattori, Y. Wada, S. Yanagida and S. Fukuzumi, J. Am. Chem. Soc., 2005, 127, 9648) have used copper (I/II) redox couples in DSSCs using ruthenium-based dyes, with very low resulting efficiencies. Peng Wang and his coworkers improved the performance of copper redox-based dye DSSCs using an organic dye (Yu Bai, Qingjiang Yu, Ning Cai, Yinghui Wang, Min Zhang and Peng Wang, Chem. Commun., 2011, 47, 4376-4378). The voltage generated from such cells far exceeded voltage generated by any iodide/triiodide based redox couple.

SUMMARY OF THE INVENTION

A dye sensitized solar cell (DSSC) is a low-cost solar cell, often a thin film solar cell. The present application discloses high efficient dye sensitized solar cells, and solar cell dyes for use in such DSSCs. In a particular embodiment, the solar cell is based on a semiconductor that is formed between a photo-sensitized anode and an electrode.

Described here is a solar cell dye for use in a DSSC, wherein the dye is a compound of formula I:

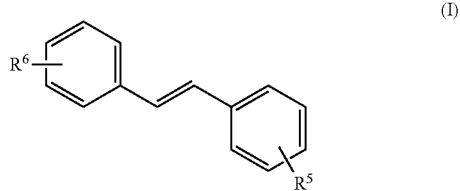

(I)

wherein $R^6$ is selected from the group consisting of —$NR^3R^4$, —$R^3$, —$OR^3$ and halo; $R^5$ is —$(CR\!=\!CR\!-\!)_n(CR\!=\!CR^2\!-\!)R^1$; n is an integer from 0 to 10, $R^1$ and $R^2$ are independently selected from the group consisting of —H, —CN, —COOR, CONHR, CON(H)OR, —$SO_3R$, —$SO_2R$—$OSO_3R$, —$PO_3HR$, and —$OPO_3HR$, further wherein at least one of $R^1$ and $R^2$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl, Also described herein is a solar cell dye for use in a DSSC, wherein the dye is a compound of formula V:

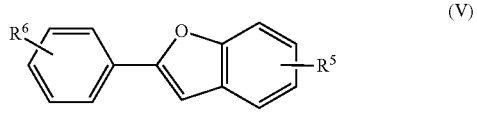

(V)

wherein either $R^6$ is selected from the group consisting of —$NR^3R^4$, —$R^3$, —$OR^3$ and halo, and $R^5$ is —$(CR\!=\!CR\!-\!)_n(CR\!=\!CR^2\!-\!)_m R^1$; or $R^6$ is —$(CR\!=\!CR\!-\!)_n(CR\!=\!CR^2\!-\!)_m R^1$, and $R^5$ is selected from the group consisting of —$NR^3R^4$, —$R^3$, —$OR^3$ and halo; and further wherein m is 0 or 1, n is an integer from 0 to 10, $R^1$ and $R^2$ are independently selected from the group consisting of —H, —CN, —COOR, CONHR, CON(H)OR, —$SO_3R$, —$SO_2R$ —$OSO_3R$, —$PO_3HR$, and —$OPO_3HR$, further wherein at least one of $R^1$ and $R^2$ is not —H, and if n=m=0 then $R^1$ is not —H; each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or $R^3$ and $R^4$ attached to their N together form a ring that is substituted or unsubstituted $C_5$-$C_{10}$ heterocycloalkyl.

Further described herein are DSSCs incorporating a solar cell dye as described above. Still further described herein are methods of making DSSCs comprising the step of incorporating a solar cell dye as described above.

DETAILED DESCRIPTION

Definitions

Unless specifically noted otherwise herein, the definitions of the terms used are standard definitions used in the art of organic chemistry and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

While particular embodiments are shown and described herein, it will be obvious to those skilled in the art that such embodiments are provided by way of example only. Numerous variations, changes, and substitutions will now occur to those skilled in the art. It should be understood that various alternatives to the embodiments described herein may be employed in practicing the methods described herein. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art. All patents and publications referred to herein are incorporated by reference.

As used in the specification and claims, the singular form "a," "an," and "the" include plural references unless the context clearly dictates otherwise.

Unless otherwise stated, structures depicted herein are also meant to include dyes which differ only in the presence of one or more isotopically enriched atoms. For example, dyes as described herein wherein one or more hydrogens are replaced by deuterium or tritium, or the replacement of one or more carbon atoms by the $^{13}$C- or $^{14}$C-enriched carbon isotope. Further, substitution with heavier isotopes, particularly deuterium ($^2$H or D) may afford certain therapeutic advantages resulting from greater metabolic stability, increased in vivo half-life, reduced dosage requirements or an improvement in therapeutic index. It is understood that deuterium in this context is regarded as a substituent of a dye of the formula (I).

The dyes described herein may also contain unnatural proportions of atomic isotopes at one or more of atoms that constitute such dyes. For example, the dyes may be radiolabeled with radioactive isotopes, such as for example tritium ($^3$H), iodine-125 ($^{125}$I) or carbon-14 ($^{14}$C). All isotopic variations of the dyes described herein, whether radioactive or not, are encompassed.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(..+−..)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the dyes described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When the dyes described herein contain olefinic double bonds or other centers of geometric asymmetry, and unless specified otherwise, it is intended that the dyes include both E and Z geometric isomers.

A "substituted" or "optionally substituted" group, means that a group (such as alkyl, aryl, heterocyclyl, cycloalkyl, hetrocyclylalkyl, arylalkyl, heteroaryl, or heteroarylalkyl) unless specifically noted otherwise, may have 1, 2 or 3 —H groups substituted by 1, 2 or 3 substituents selected from halo, trifluoromethyl, trifluoromethoxy, methoxy, —COOH, —CHO, —NH$_2$, —NO$_2$, —OH, —SH, —SMe, —NHCH$_3$, —N(CH$_3$)$_2$, —CN and the like.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Dyes described herein also include crystalline and amorphous forms of those dyes, including, for example, polymorphs, pseudopolymorphs, solvates, hydrates, unsolvated polymorphs (including anhydrates), conformational polymorphs, and amorphous forms of the dyes, as well as mixtures thereof. "Crystalline form," "polymorph," and "novel form" may be used interchangeably herein, and are meant to include all crystalline and amorphous forms of the dye listed above, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Compositions

Dye-Sensitized Solar Cells

Dye-sensitized solar cells described herein comprise a photoanode, a photocathode, and a redox electrolyte disposed between the photoanode and the photocathode.

The photoanode comprises a metal oxide such as titanium dioxide. The oxide can be in the form of nanoparticles such as mesoporous titanium oxide nanoparticles. The photoanode is sensitized with a solar cell dye deposited on a flexible metal, a transparent conducting substrate, or a fluorine-doped tin oxide coated glass. The photocathode comprises a catalytic layer comprising one or more thin layers of platinum, polythiophenes including PEDOT, polyanilines, polypyrroles, or carbon (including carbon nanotubes and graphenes). The redox electrolyte is commonly selected from a pair consisting of iodide/triiodide, Co(II)/Co(II) organic ligand complexes, and Cu(I)/Cu(II) organic ligand complexes.

Also described herein are solar cell dyes for use in a DSSC, wherein the dye is a compound of formula I:

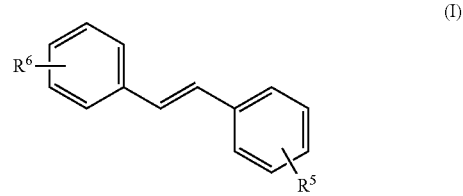

wherein R$^6$ is selected from the group consisting of —NR$^3$R$^4$, —R$^3$, —OR$^3$ and halo;

R$^5$ is —(CR=CR—)$_n$(CR=CR$^2$—)R$^1$;

n is an integer from 0 to 10;

R$^1$ and R$^2$ are independently selected from the group consisting of —H, —CN, —COOR, CONHR, CON(H)OR, —SO$_3$R, —SO$_2$R —OSO$_3$R, —PO$_3$HR, and —OPO$_3$HR, further wherein at least one of R$^1$ and R$^2$ is not —H;

each R is independently selected from —H and C$_{1-6}$ linear or branched alkyl; and R$^3$ and R$^4$ are independently selected from the group consisting of H, substituted or unsubstituted linear or branched C$_1$-C$_{10}$ alkyl, substituted or unsubstituted phenyl, substituted or unsubstituted C$_6$-C$_{10}$ aryl, substituted or unsubstituted C$_5$-C$_{10}$ heteroaryl, substituted or unsubstituted C$_5$-C$_{10}$ cycloalkyl, and substituted or unsubstituted C$_5$-C$_{10}$ heterocycloalkyl; or N, R$^3$ and R$^4$ together form a ring that is substituted or unsubstituted C$_5$-C$_{10}$ heterocycloalkyl.

In some embodiments, the solar cell dye may be of formula II, III or IV:

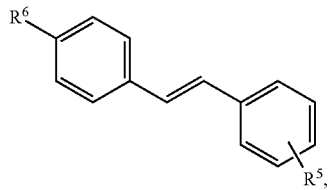

(II)

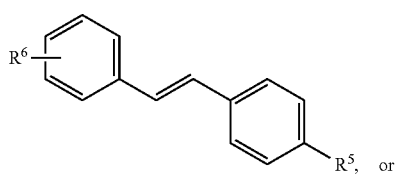

(III)

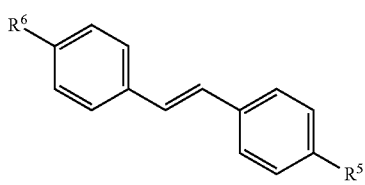

(IV)

where $R^5$ and $R^6$ are as described in the preceding paragraph.

The structures of the solar cell dyes described above, as shown in formulae I-IV, have a central stilbene structure with two substituent moieties, R5 and R6, attached thereto. One substituent moiety is attached to any position on each of the phenyl moieties, as shown in formula I. For example, the substituent moieties may be attached to positions on the phenyl moieties as shown in formulae II-IV.

In general, the substituent moiety $R^6$ will be a pi electron-donating moiety, and the other substituent moiety $R^5$ will be a pi electron-withdrawing moiety. The pi electron-donating moiety may be an amino, alkyl or alkoxy moiety represented herein by —$NR^3R^4$, —$R^3$, or —$OR^3$. One alternative pi electron-donating moiety is the amino moiety —$NR^3R^4$, which may, for example, be selected from the group consisting of diethylamino, diphenylamino, methyl(phenyl)amino, cyclohexyl(methyl)amino, bis(4-methoxyphenyl)amino, bis(4-(tert-butyl)phenyl)amino, di(pyridin-2-yl)amino, di(pyridin-3-yl)amino, di(pyridin-4-yl)amino, piperidin-1-yl, 4-methylpiperazin-1-yl, 4-phenylpiperazin-1-yl, pyrrolidin-1-yl, and morpholino. In other embodiments, the pi electron-donating moiety is —$R^3$, or —$OR^3$, and may, for example, be selected from the group consisting of 3',4'-dimethoxyphenyl, tert-butyl, phenyloxy, and methoxy. In still another alternative embodiment, the pi electron-donating moiety is halo selected from fluoro, bromo, chloro, and iodo. In one embodiment, the halo is bromo.

The pi electron-withdrawing moiety $R^5$ may be —H, —CN, —COOR, CONHR, CON(H)OR, —$SO_3R$, —$SO_2R$ —$OSO_3R$, —$PO_3HR$, or —$OPO_3HR$, and maybe directly attached to the central structure, or linked via from one to about ten conjugated carbon-carbon double bonds. This moiety is represented herein by the structure —(CR=CR—)n(CR=CR²—)$R^1$, wherein n is an integer from 0 to 10; and $R^1$ and $R^2$ are independently selected from the group consisting of —H, —CN, —COOR, CONHR, CON(H)OR, —$SO_3R$, —$SO_2R$ —$OSO_3R$, —$PO_3HR$, or —$OPO_3HR$, further wherein at least one of $R^1$ and $R^2$ is not —H. As used herein, each R is independently selected from —H and $C_{1-6}$ linear or branched alkyl. In one alternative embodiment, $R^1$ and $R^2$ together are —CN and —COOH, n=0 and m=1.

In the solar cell dyes described herein, $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or N, $R^3$ and $R^4$ together form a ring that is substituted or unsubstituted $C_5$-$C_{10}$ heterocycloalkyl. In alternative embodiments, $R^3$ and $R^4$ are methyl, ethyl, cyclohexyl, phenyl, 4-methoxyphenyl, 4-(tert-butyl)phenyl, pyridin-2-yl, pyridin-3-yl, or pyridin-4-yl, or N, $R^3$ and $R^4$ together are piperidin-1-yl, 4-methylpiperazin-1-yl, 4-phenylpiperazin-1-yl, pyrrolidin-1-yl, or morpholino.

The following exemplary solar cell dyes have been synthesized:

| Entry | Structure | Compound # |
|---|---|---|
| 1 | 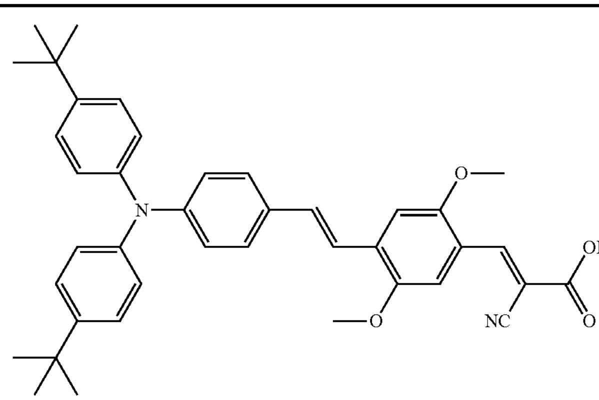 | WBI-PC-63 |

-continued
| Entry | Structure | Compound # |
|---|---|---|
| 2 | 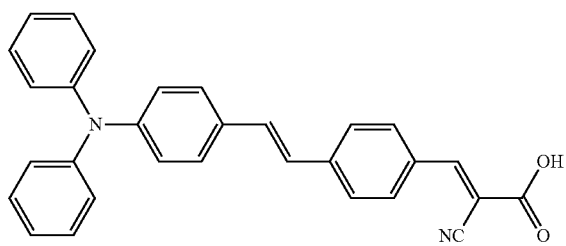 [SMILES: N#C/C(=C\c1ccc(/C=C/c2ccc(N(c3ccccc3)c3ccccc3)cc2)cc1)C(=O)O] | WBI-PC-64 |
| 3 | 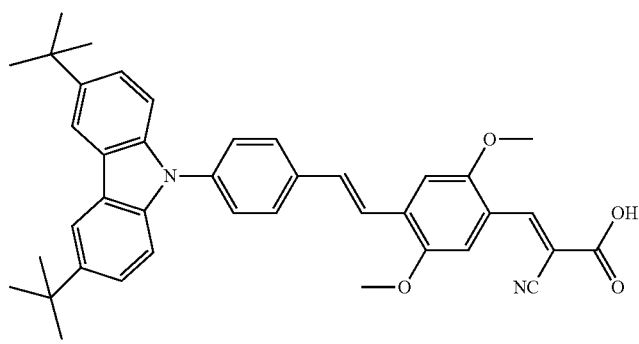 [SMILES: COc1cc(/C=C(\C#N)C(=O)O)c(OC)cc1/C=C/c1ccc(-n2c3ccc(C(C)(C)C)cc3c3cc(C(C)(C)C)ccc32)cc1] | WBI-PC-66 |
| 4 | 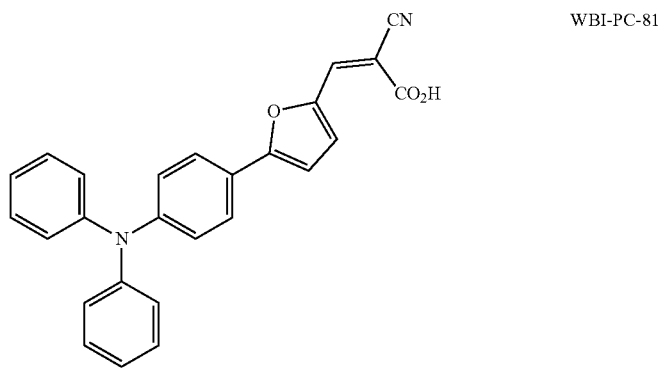 | WBI-PC-81 |
| 5 | 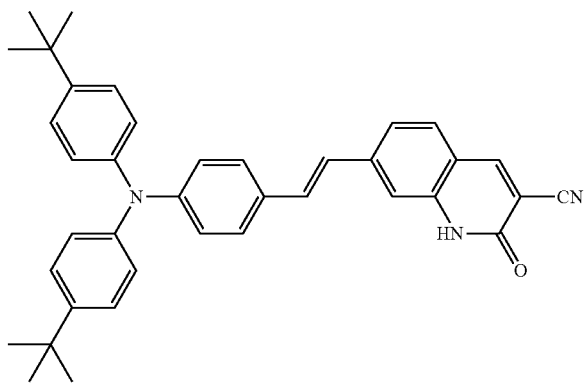 [SMILES: CC(C)(C)c1ccc(N(c2ccc(/C=C/c3ccc4cc(C#N)c(=O)[nH]c4c3)cc2)c2ccc(C(C)(C)C)cc2)cc1] | WBI-PC-174 |

-continued

| Entry | Structure | Compound # |
|-------|-----------|------------|
| 6 | 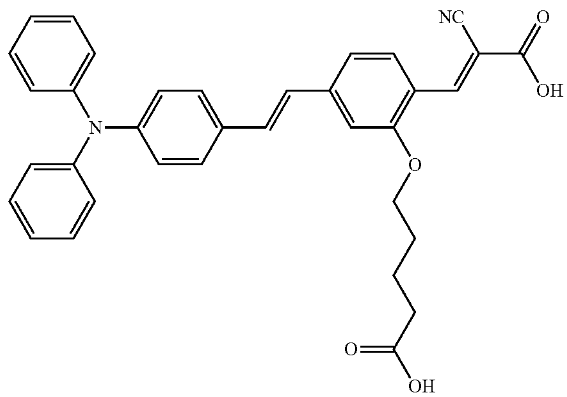 [SMILES: N#C/C(=C\c1ccc(/C=C/c2ccc(N(c3ccccc3)c3ccccc3)cc2)cc1OCCCCC(=O)O)C(=O)O] | WBI-PC-78 |
| 7 | 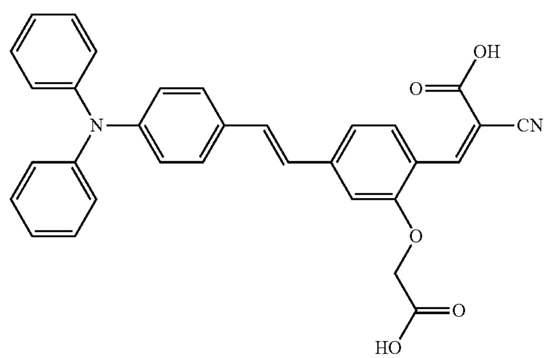 [SMILES: N#C/C(=C/c1ccc(/C=C/c2ccc(N(c3ccccc3)c3ccccc3)cc2)cc1OCC(=O)O)C(=O)O] | WBI-PC-190 |
| 8 | 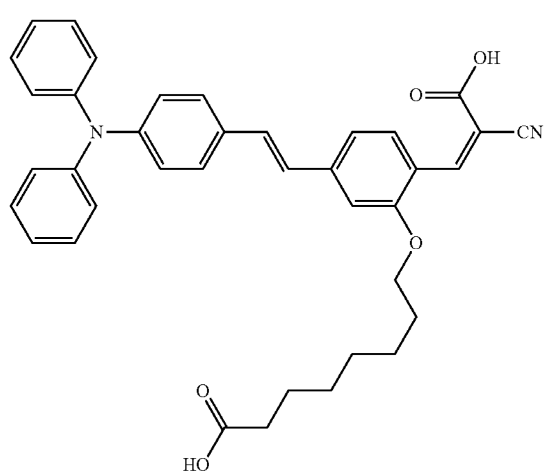 | WBI-PC-191 |

Target 2

| Entry | Structure | Compound # |
|---|---|---|
| 9 | 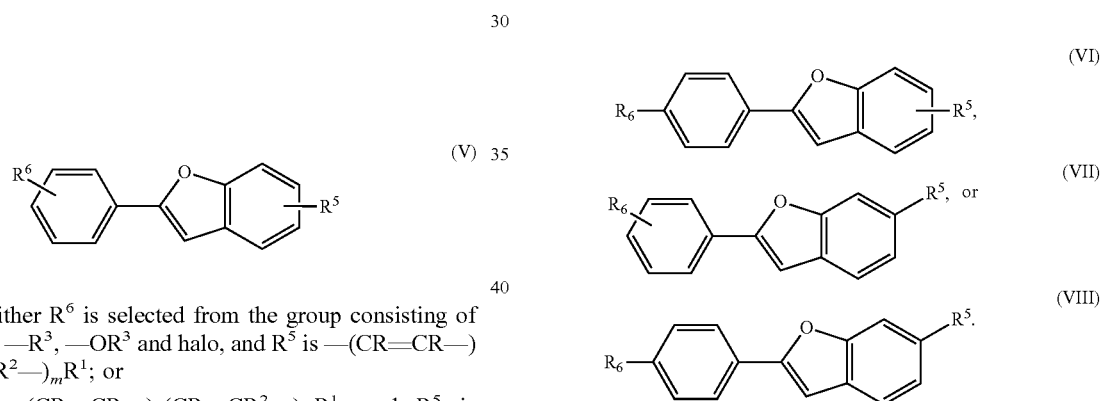
Target 3 | WBI-PC-192 |

Also described herein are solar cell dyes for use in a DSSC, wherein the dye is a compound of formula V:

(V)

wherein either $R^6$ is selected from the group consisting of —$NR^3R^4$, —$R^3$, —$OR^3$ and halo, and $R^5$ is —(CR=CR—)$_n$(CR=$CR^2$—)$_m R^1$; or $R^6$ is —(CR=CR—)$_n$(CR=$CR^2$—)$_m R^1$, and $R^5$ is selected from the group consisting of —$NR^3R^4$, —$R^3$, —$OR^3$ and halo; and further wherein m is 0 or 1;

n is an integer from 0 to 10;

$R^1$ and $R^2$ are independently selected from the group consisting of —H, —CN, —COOR, CONHR, CON(H)OR, —$SO_3R$, —$SO_2R$ —$OSO_3R$, —$PO_3HR$, and —$OPO_3HR$, further wherein at least one of $R^1$ and $R^2$ is not —H, and if n=m=0 then $R^1$ is not —H;

each R is independently selected from —H and $C_{1-6}$ linear or branched alkyl; and $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or N, $R^3$ and $R^4$ together form a ring that is substituted or unsubstituted $C_5$-$C_{10}$ heterocycloalkyl.

For example, the solar cell dye may be of formula VI, VII or VIII:

(VI)

(VII)

(VIII)

The structures of the solar cell dyes described above, as shown in formulae V-VII, have a phenyl-benzofuranyl central structure with two substituent moieties, $R^5$ and $R^6$, attached thereto. One substituent moiety is attached to any position on the phenyl moiety, and the other substituent moiety is attached to any position on the phenyl ring of the benzofuranyl moiety, as shown in formula I. For example, the substituent moieties may be attached to positions on the phenyl and benzofuranyl moieties as shown in formulae VI-VIII.

In general, one of the substituent moieties ($R^5$ or $R^6$) will be a pi electron-donating moiety, and the other substituent moiety ($R^6$ or $R^5$) will be a pi electron-withdrawing moiety. The pi electron-donating moiety may be an amino, alkyl or alkoxy moiety represented herein by —$NR^3R^4$, —$R^3$, or —$OR^3$. One alternative pi electron donating moiety is the amino moiety —$NR^3R^4$, which may, for example, be selected from the group consisting of diethylamino, diphenylamino, methyl(phenyl)amino, cyclohexyl(methyl)amino, bis(4-methoxyphenyl)amino, bis(4-(tert-butyl)phenyl)amino, di(pyridin-2-yl)amino, di(pyridin-3-yl)amino, di(pyridin-4-yl)amino, piperidin-1-yl, 4-methylpiperazin-1-yl, 4-phenylpiperazin-1-yl, pyrrolidin-1-yl, and morpholino. In other embodiments, the pi electron-donating moiety is —$R^3$, or —$OR^3$, and may be selected from the group consisting of 3',4'-dimethoxyphenyl, tert-butyl, phenyoxy, and methoxy. In still other embodiments, the pi electron-donating moiety is halo selected from fluoro, bromo, chloro, and iodo. In one embodiment, the halo is bromo.

The pi electron-withdrawing moiety may be —H, —CN, —COOR, CONHR, CON(H)OR, —$SO_3R$, —$SO_2R$ —$OSO_3R$, —$PO_3HR$, or —$OPO_3HR$, and maybe directly attached to the central structure, or linked via from one to about ten conjugated carbon-carbon double bonds. This moiety is therefore represented herein by the structure —$(CR{=}CR-)_n(CR{=}CR^2-)_mR^1$, wherein m is 0 or 1; n is an integer from 0 to 10; and $R^1$ and $R^2$ are independently selected from the group consisting of —H, —CN, —COOR, CONHR, CON(H)OR, —$SO_3R$, —$SO_2R$ —$OSO_3R$, —$PO_3HR$, or —$OPO_3HR$, further wherein at least one of $R^1$ and $R^2$ is not —H, and if n=m=0 then $R^1$ is not —H. As used herein, each R is independently selected from —H and $C_{1-6}$ linear or branched alkyl. In one embodiment, $R^1$ and $R^2$ together are —CN and —COOH, n=0 and m=1.

In the solar cell dyes described herein, $R^3$ and $R^4$ are independently selected from the group consisting of H, substituted or unsubstituted linear or branched $C_1$-$C_{10}$ alkyl, substituted or unsubstituted phenyl, substituted or unsubstituted $C_6$-$C_{10}$ aryl, substituted or unsubstituted $C_5$-$C_{10}$ heteroaryl, substituted or unsubstituted $C_5$-$C_{10}$ cycloalkyl, and substituted or unsubstituted $C_5$-$C_{10}$ heterocycloalkyl; or N, $R^3$ and $R^4$ together form a ring that is substituted or unsubstituted $C_5$-$C_{10}$ heterocycloalkyl. In alternative embodiments, $R^3$ and $R^4$ are methyl, ethyl, cyclohexyl, phenyl, 4-methoxyphenyl, 4-(tert-butyl)phenyl, pyridin-2-yl, pyridin-3-yl, or pyridin-4-yl, or N, $R^3$ and $R^4$ together are piperidin-1-yl, 4-methylpiperazin-1-yl, 4-phenylpiperazin-1-yl, pyrrolidin-1-yl, or morpholino.

Further exemplary solar cell dyes according to the present invention are shown in the Table below.

| Compound | Structure | MW |
|---|---|---|
| BC-146 | 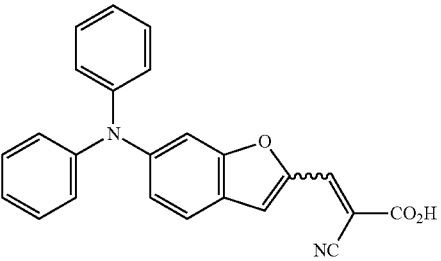<br>2-cyano-3-(6-diphenylamino)benzofuran-2-yl)acrylic acid | 380.40 |
| BC-147 | 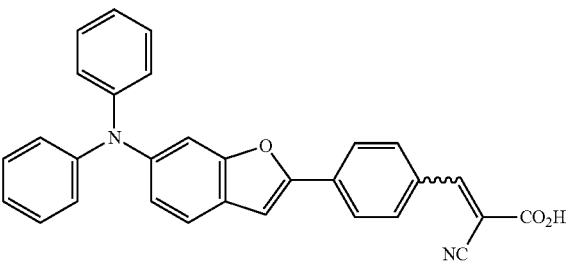<br>2-cyano-3-(4-(6-diphenylamino)benzofuran-2-yl)phenyl)acrylic acid | 456.50 |
| BC-149 | 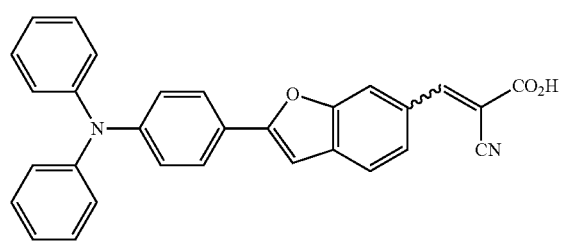<br>2-cyano-3-(2-(4-(diphenylamino)phenyl)benzofuran-6-yl)acrylic acid | 456.50 |

| Compound | Structure | MW |
|---|---|---|
| BC-151 | 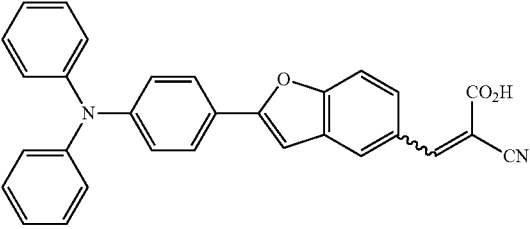<br>2-cyano-3-(2-(4-(diphenylamino)phenyl)benzofuran-5-yl)acrylic acid | 456.50 |
| BC-152 | 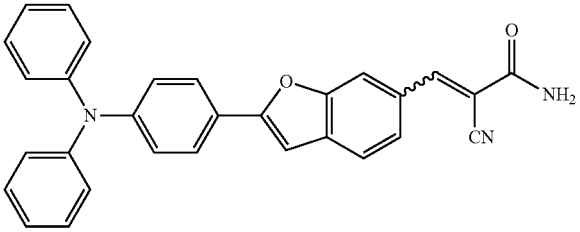<br>2-cyano-3-(2-(4-(diphenylamino)phenyl)benzofuran-6-yl)acrylamide | 455.52 |
| BC-153 | 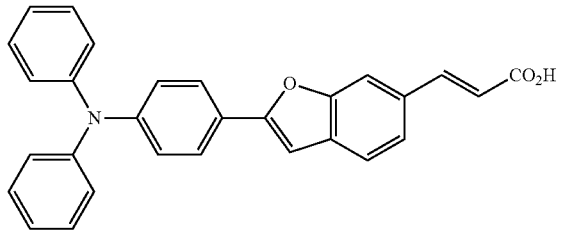<br>(E)-3-(2-(4-(diphenylamino)phenyl)benzofuran-6-yl)acrylic acid | 431.49 |
| BC-154 | 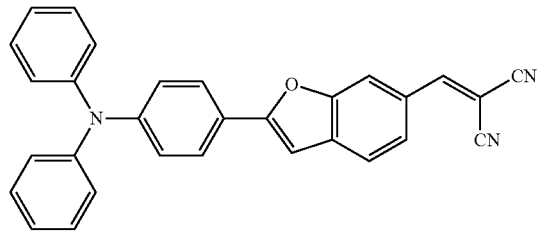<br>2-((2-(4-(diphenylamino)phenyl)benzofuran-6-yl)methylene)malononitrile | 437.50 |
| BC-155 | 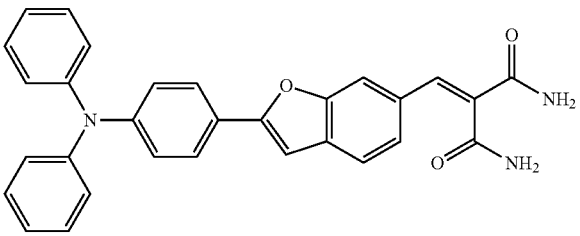<br>2-((2-(4-(diphenylamino)phenyl)benzofuran-6-yl)methylene)malonamide | 473.53 |

-continued
| Compound | Structure | MW |
|---|---|---|
| BC-156 | 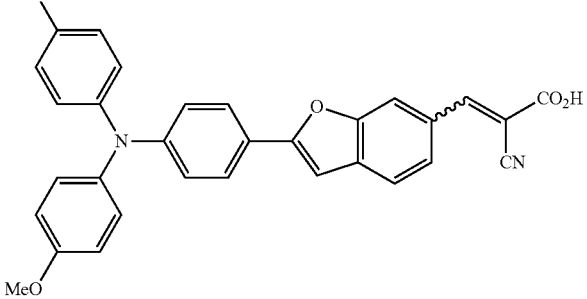 3-(2-(4-(bis-(4-methoxyphenyl)amino)phenyl)benzofuran-6-yl)-2-cyanoacrylic acid | 516.55 |
| BC-157 | 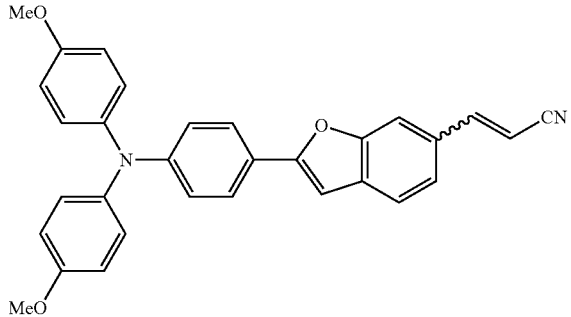 ~5:1 E:Z 3-(2-(4-(bis(4-methoxyphenyl)amino)phenyl)benzofuran-6-yl)acrylonitrile | 472.54 |
| BC-158 | 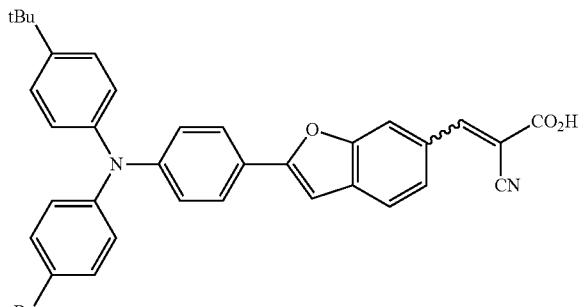 3-(2-(4-(bis(4-(tert-butyl)phenyl)amino)phenyl)benzofuran-6-yl)-2-cyanoacrylic acid | 568.72 |
| BC-159 | 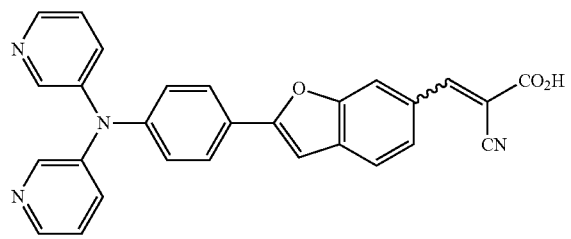 2-cyano-3-(2-(4-(di(pyridin-3-yl)amino)phenyl)benzofuran-6-yl)acrylic acid | 458.14 |

-continued

| Compound | Structure | MW |
|---|---|---|
| BC-160 | dimethyl 2-((2-(4-(diphenylamino)phenyl)benzofuran-6-yl)methylene)malonate | 503.55 |
| BC-161 | methyl 2-cyano-3-(2-(4-(diphenylamino)phenyl)benzofuran-6-yl)acrylate | 470.53 |
| BC-162 | 3-(2-(4-bromophenyl)benzofuran-6-yl)-2-cyanoacrylic acid | 368.19 |
| BC-163 | 2-cyano-3-(2-(4-(diphenylamino)phenyl)benzofuran-6-yl)-N-(pyridin-2-ylmethyl)acrylamide | 546.63 |
| BC-165 | 2-cyano-3-(2-(3',4'-dimethoxy-[1,1'-biphenyl]-4-yl)benzofuran-6-yl)-acrylic acid | 425.44 |
| BC-166 | 2-cyano-3-(2-(4-(piperidin-1-yl)phenyl)benzofuran-6-yl)-acrylic acid | 372.42 |

-continued

| Compound | Structure | MW |
|---|---|---|
| BC-167 | 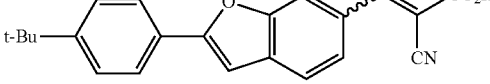<br>3-(2-(4-(tert-butyl)phenyl)benzofuran-6-yl)-2-cyanoacrylic acid | 345.40 |
| BC-168 | 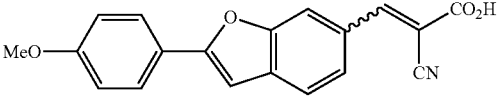<br>2-cyano-3-(2-(4-(methoxyphenyl)benzofuran-6-yl)-acrylic acid | 319.32 |
| BC-169 | 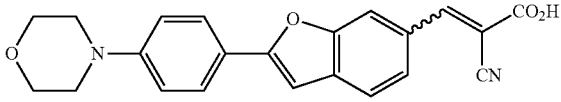<br>2-cyano-3-(2-(4-(morpholinophenyl)benzofuran-6-yl)acrylic acid | 374.40 |
| BC-170 | 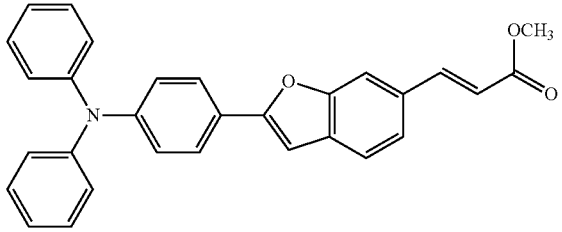<br>methyl (E)-3-(2-(4-(diphenylamino)phenyl)benzofuran-6-yl)acrylate | 445.52 |
| BC-171 | 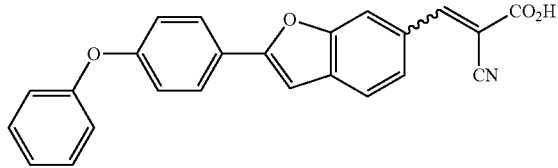<br>2-cyano-3-(2-(4-(phenoxyphenyl)benzofuran-6-yl)acrylic acid | 381.39 |
| BC-172 | 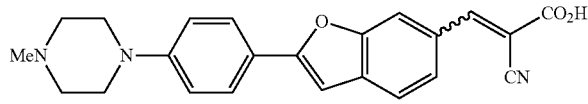<br>2-cyano-3-(2-(4-(4-methylpiperazin-1-yl)phenyl)benzofuran-6-yl)acrylic acid | 387.44 |
| BC-173 | 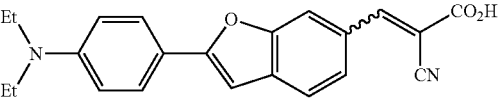<br>2-cyano-3-(2-(4-diethylamino)phenyl)benzofuran-6-yl)acrylic acid | 360.41 |

| Compound | Structure | MW |
|---|---|---|
| BC-175 | 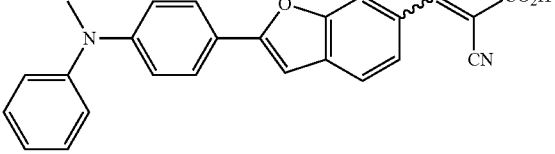<br>2-cyano-3-(2-(4-(methyl(phenyl)amino)phenyl)benzofuran-6-yl)acrylic acid | 394.43 |
| BC-176 | 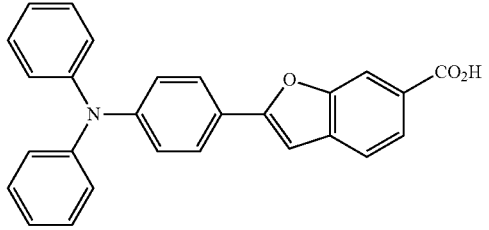<br>2-(4-(diphenylamino)phenyl)benzofuran-6-carboxylic acid | 405.45 |

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein. However, other equivalent separation or isolation procedures can also be used.

When desired, the (R)- and (S)-isomers of the solar cell dyes described herein, if present, may be resolved by methods known to those skilled in the art, for example by formation of diastereomeric salts or complexes which may be separated, for example, by crystallization; via formation of diastereomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The solar cell dyes described herein can be optionally contacted with a pharmaceutically acceptable acid to form the corresponding acid addition salts. Pharmaceutically acceptable forms of the solar cell dyes recited herein include pharmaceutically acceptable salts, chelates, non-covalent complexes or derivatives, prodrugs, and mixtures thereof. In certain embodiments, the dyes described herein are in the form of pharmaceutically acceptable salts. In addition, if the dye described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") include those embodiments, for example, an embodiment of any composition of matter, composition, method, or process, or the like, that "consist of" or "consist essentially of" the described features.

EXPERIMENTAL

All reagents were purchased from commercial suppliers and used as supplied unless stated otherwise. Reactions were carried out in air unless stated otherwise. 400 MHz $^1$H NMR spectra were obtained on a JEOL AS 400 spectrometer. Low-resolution mass spectra (LRMS) were obtained on a JEOL JMS-T100LC DART/AccuTOF mass spectrometer. Measurement of reversal of protein aggregation may be carried out using such assays as Bis-ANS Fluorescence as described in, for example, W. T. Chen et al., J. Biol. Chem, 2011, 286 (11), 9646.

General synthetic scheme for making the compounds in Examples 1-9 herein:

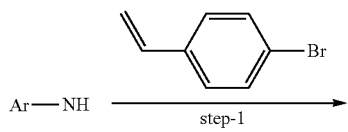

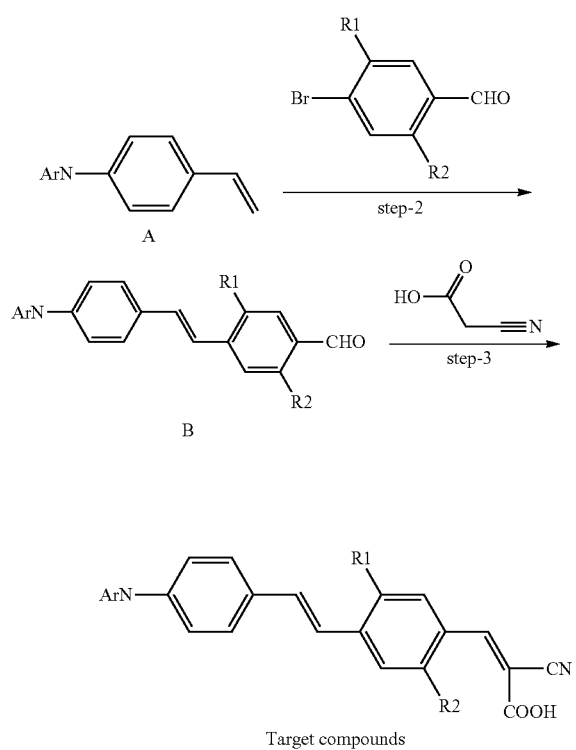

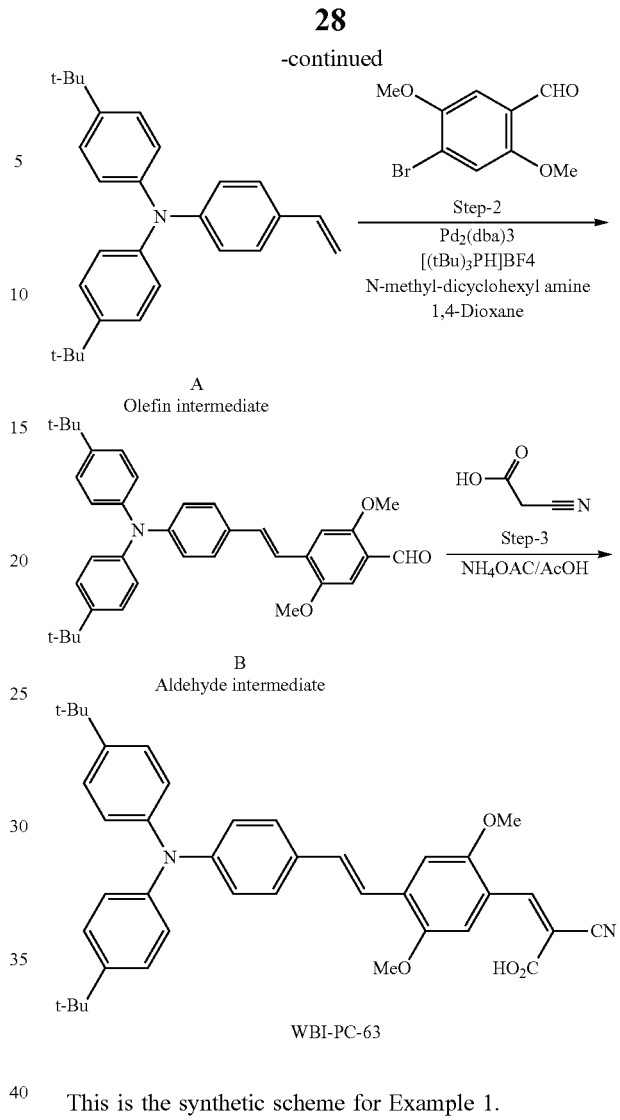

WBI-PC-63

This is the synthetic scheme for Example 1.

Synthesis of Olefin Intermediate A

To a mixture of Bis((4-t-butyl)phenyl)amine (15.0 g, 0.053 mol) and 4-bromostyrene (~7 mL, 0.053 mol, 1 equiv.) in an oven dried 500 mL Schlenck flask was added Pd$_2$(dba)$_3$ (488 mg, 0.533 mmol), phosphine (360 mg, 1.06 mmol) and NaOtBu (5.63 g, 0.059 mol). The flask was flushed with N$_2$ for 10 min, treated with degassed 1,4-dioxane (50 mL) and the mixture was heated to 80° C. for 1.5 hours under N$_2$. The reaction was monitored by TLC for completion before cooling to room temperature. The organic layer was washed with DI water (2×100 mL) and then saturated brine solution (100 mL). The combined organic layer was then dried with anhydrous Na$_2$SO$_4$ and concentrated. The resulting crude olefin was used directly in the following step without further purification.

Synthesis of Aldehyde Intermediate B

To the dark brown olefin (olefin intermediate A) in the Schlenck flask under N$_2$ was added 4-bromo-2,5-dimethoxy benzaldehyde (13.0 g, 0.053 mol), N-methyl-dicyclohexyl amine (23 mL, 0.112 mol), Pd$_2$(dba)$_3$ (488 mg, 0.533 mmol), and the phosphine salt (307 mg, 1.06 mmol) under N$_2$. Dry and degassed 1,4-dioxane (25 mL) was then added to the Example 1

Synthesis of (Z)-3-[4-[(E)-2-[4-(4-tert-butyl-N-(4-tert-butylphenyl)anilino)phenyl]vinyl]-2,5-dimethoxy-phenyl]-2-cyano-prop-2-enoic acid (WBI-PC-63)

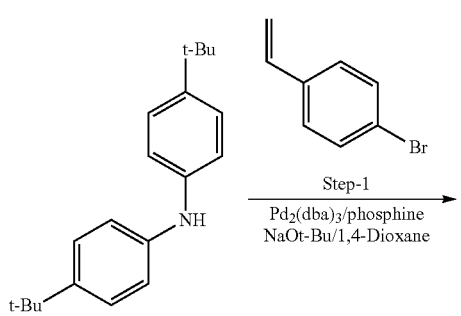

flask and the mixture was stirred at 60° C. under N₂ for 2.5 hours. The mixture turned from purple to yellow green during the course of the reaction. Crude LCMS showed the reaction was complete, and the mixture was filtered and the collected solid washed with copious amounts of CH₂Cl₂ to separate the product from the inorganic materials. The combined CH₂Cl₂/dioxane layer was concentrated under reduced pressure. The resulting orange-red residue was dissolved in CH₂Cl₂ (60 mL) and washed with 1N HCl (150 mL). The aqueous layer was extracted with CH₂Cl₂ (2×25 mL), and the combined organic layer was concentrated under reduced pressure to give a reddish yellow residue, which was dried on the vacuum line for 1 hour at room temperature and the resulting reddish yellow crude solid product was used directly in the following reaction without further purification.

Synthesis of WBI-PC-63

To the aldehyde intermediate B was added glacial acetic acid (150 mL) followed by cyanoacetic acid (11.0 g, 0.129 mol) and ammonium acetate (12.3 g, 0.160 mol), and the reaction was refluxed for 5 hours. The reaction was then cooled to room temperature, and was then slowly added to ice-cold DI water (1.5 L), and stirred at room temperature for 1 hour. The precipitate was filtered and washed with DI water and hexanes, and dried overnight in a vacuum oven at 60° C. to afford WBI-PC-63 as a dark red solid. (31.5 g; 95% overall yield). LCMS (M+1): 615.3; 1H NMR (400 MHz, d6-DMSO): 8.52 (s, 1H), 7.85 (s, 1H), 7.46-6.86 (m, 15H), 3.94 (s, 3H), 3.83 (s, 3H), 1.26 (s, 18H).

Example 2

Synthesis of (Z)-2-cyano-3-[4-[(E)-2-[4-(N-phenylanilino)phenyl]vinyl]phenyl]prop-2-enoic acid (WBI-PC-64)

Synthetic Scheme

Scheme-3 Synthesis of WBI-PC-64

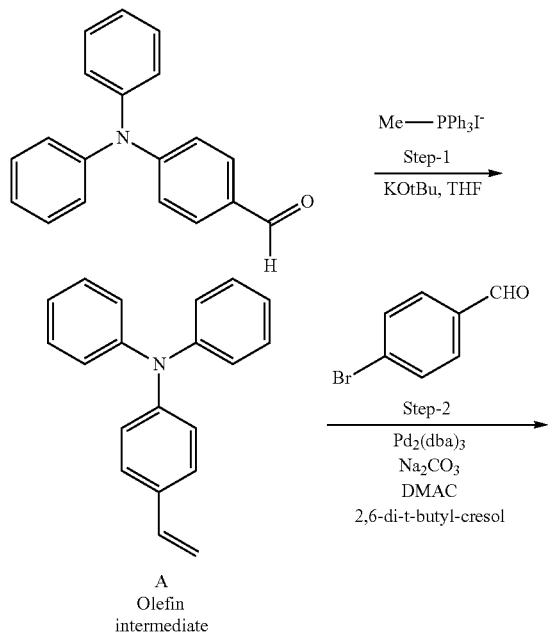

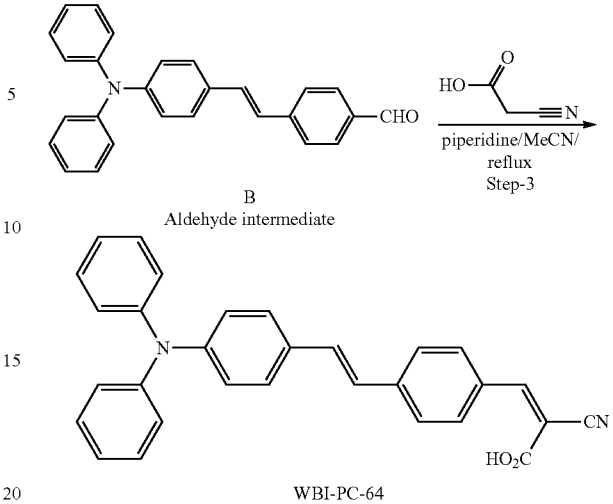

Synthesis of Olefin Intermediate A

The starting aldehyde (4.5 g, 0.0165 mol) was placed in a pear shaped flask with 25 mL of dry THF and the yellow solution was degassed for 20 min with N₂. KOtBu (2.5 g, 1.25 equiv.) and methyltriphenylphosphonium iodide (8.33 g, 1.25 equiv.) were combined in a separate 250 mL Schlenck flask equipped with a stir bar and placed under N₂. The THF solution of A was then cannula transferred under N₂ into the Schlenck flask. The solution was stirred at room temperature under N₂ for 5 hr. The reaction mixture was partitioned between 125 mL of CH₂Cl₂ and 100 mL of DI water. The mixture was acidified using concentrated HCl (pH~4). The separated organic layer was then washed with DI water (2×100 mL) and then saturated brine solution (100 mL). The combined organic layer was then dried over anhydrous Na₂SO₄ and concentrated under reduced pressure. 1H NMR of the crude product confirmed the formation of the desired Wittig product. The crude material was then purified on silica gel using n-hexanes as the eluent to afford 3.10 g of olefin product A as a white solid (78% yield).

Synthesis of Aldehyde Intermediate B

A Schlenck flask was charged sequentially with A (1.00 g, 3.69 mmol), 4-bromobenzaldehyde (310 mg, 1.68 mmol), Pd₂(dba)₃ (15 mg), sodium carbonate (444 mg, 1.13 equiv.), and 2,6-di-t-butylcresol (732 mg, 0.33 mmol). The reaction mixture was then treated with dry dimethylacetamide (DMAC, 10 mL) and the flask flushed with N₂ for 20 min at room temperature. The reaction was then placed in an oil bath at 120° C. under N₂ for 24 hours. The color of the solution changed from light yellow to dark yellow. The reaction was stopped and CH₂Cl₂ (100 mL) was added, and washed with of DI water (2×100 mL). The organic layer was washed with saturated brine solution (100 mL), dried over anhydrous Na₂SO₄, and concentrated under reduced pressure. The crude product was then purified on silica gel using hexanes/CH₂Cl₂ (85:15) as the eluent to give the desired aldehyde product B as a yellow solid (600 mg, 45% yield).

Synthesis of WBI-PC-64

Combined B (404 mg, 1.076 mmol) was treated with cyanoacetic acid (92 mg, 1 equiv.) and piperidine (0.22 mL, 2 equiv.) in 30 mL of dry MeCN and flushed with N₂ at room temperature for 15 min. The reaction flask was then placed into an oil bath (82° C.) and refluxed under N₂ for 18 hours. The reaction turned from yellow to orange red and became homogeneous. The reaction was stopped, allowed to cool to room temperature and the solvent removed under reduced pressure. The residue was placed in a separatory funnel with 100 mL of CH₂Cl₂. The organic layer was washed with 0.1 N HCl solution (100 mL) and DI water (100 mL). The organic layer was then dried over anhydrous Na₂SO₄ and dried under reduced pressure to yield WBI-PC-64 (350 mg, 79% yield) as dark red crude product. LCMS (M+1): 443.1; 1H NMR (400 MHz, d6-DMSO): 8.29 (s, 1H), 8.10 (s, 2H), 7.75 (s, 2H), 7.32-6.92 (m, 16H).

Example 3

Synthesis of (E)-2-cyano-3-[4-[(E)-2-[4-(3,6-ditert-butylcarbazol-9-yl)phenyl]vinyl]-2,5-dimethoxyphenyl]prop-2-enoic acid (WBI-PC-66)

Synthetic Scheme

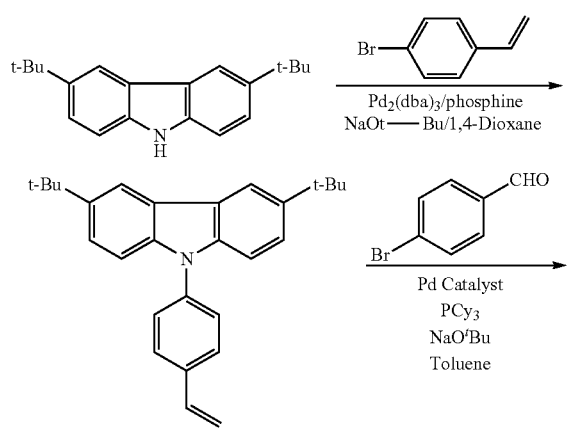

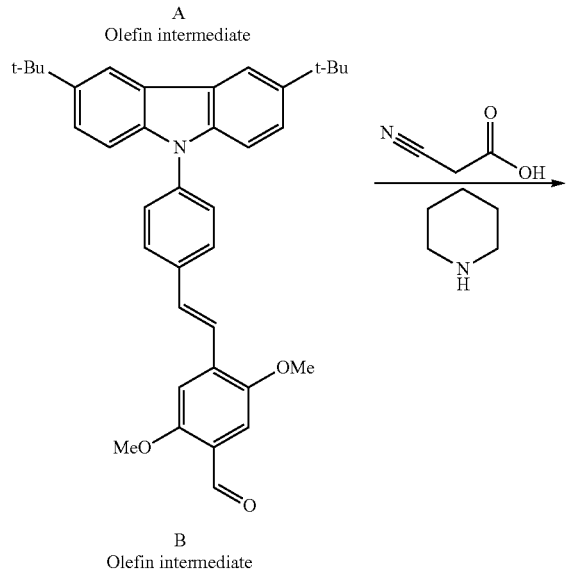

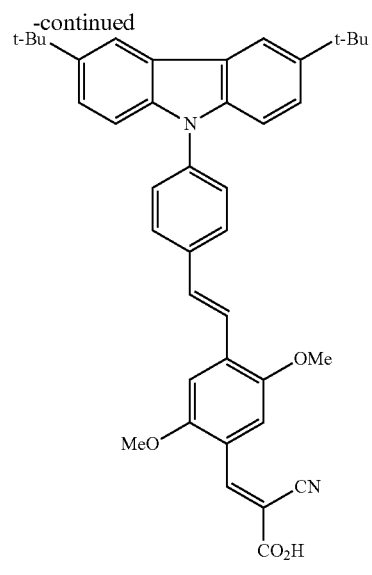

WBI-PC-66

Synthesis of Olefin Intermediate A

Bis(3,6-t-butyl)carbazole (0.0053 mol) and 4-bromostyrene (~0.7 mL, 10.0053 mol, equiv.) were combined in an oven dried 100 mL Schlenck flask with Pd₂(dba)₃ (48 mg, 0.0533 mmol), phosphine (36 mg, 1.06 mmol) and NaOtBu (0.56 g, 0.0059 mol). The flask was flushed with N₂ for 10 min, then dry, degassed 1,4-dioxane (10 mL) was added and the reaction was heated at 80° C. for 1.5 hours under N₂. The reaction was monitored by TLC to confirm consumption of starting materials and then cooled to room temperature. The organic layer was washed with DI water (2×25 mL), then saturated brine solution (25 mL). The organic layer was dried over anhydrous Na₂SO₄ and concentrated under reduced pressure. The resulting crude olefin intermediate A was used in the following step without further purification.

Synthesis of Aldehyde Intermediate B

The olefin intermediate A (5.0 mmol) was mixed with 4-bromo benzaldehyde (1.39 g, 5.0 mmol, 1.5 equiv.) in a 100 mL Schlenck vessel with dry toluene (30 mL) and flushed with N₂ for 20 min. To this solution were added Pd(dba)3 (92 mg, 2 mol %), tricyclohexylphosphine (57 mg, 4 mol %) and NaOtBu (724 mg, 1.5 equiv.) under N₂. The reaction mixture was then refluxed for 18 hours under N₂. The reaction was stopped and allowed to cool to room temperature. The mixture was treated with DI water (25 mL), the organic layer was then washed sequentially with 1 N HCl (25 mL) and saturated brine (25 mL) solution. The organic layer was concentrated under reduced pressure and purified on silica gel column using Hexanes:DCM to give the aldehyde product B as a yellow solid (2.54 g, 78% yield).

Synthesis of WBI-PC-66

The aldehyde intermediate B (0.82 g, 2.70 mmol, oily solid) was placed in a RB flask with cyanoacetic acid (505 mg, 2.2 equiv.). Piperidine (1.23 mL, 4.6 equiv.) was added with 15 mL of dry MeCN. The mixture was placed under N₂ and stirred for 15 min. The mixture was then refluxed for 12 hours under N₂. The reaction was stopped and the MeCN was concentrated under reduced pressure to yield a residue. The residue was dissolved in 100 mL of EtOAC and washed with 50 mL of DI water. The organic layer was then washed with 0.1N HCl (75 mL). The organic layer was then analyzed by TLC and DART/MS (negative ion mode) and product formation was confirmed. The organic layer was concentrated under reduced pressure and the crude product was purified on silica gel using DCM:MeOH (100:0 to 90:10) to afford WBI-PC-66 as a yellowish red solid. 1H NMR (400 MHz, d6-DMSO) δ 8.54 (s, 1H), 8.29 (d, 2H), 7.89– (m, 10H), 5.75 (s, 2H), 3.98, 3.88 (2s, 3H), 1.41 (s, 18H).

Example 4

Synthesis of (Z)-2-cyano-3-[5-[4-(N-phenylanilino) phenyl]-2-furyl]prop-2-enoic acid (WBI-PC-81)

Synthetic Scheme

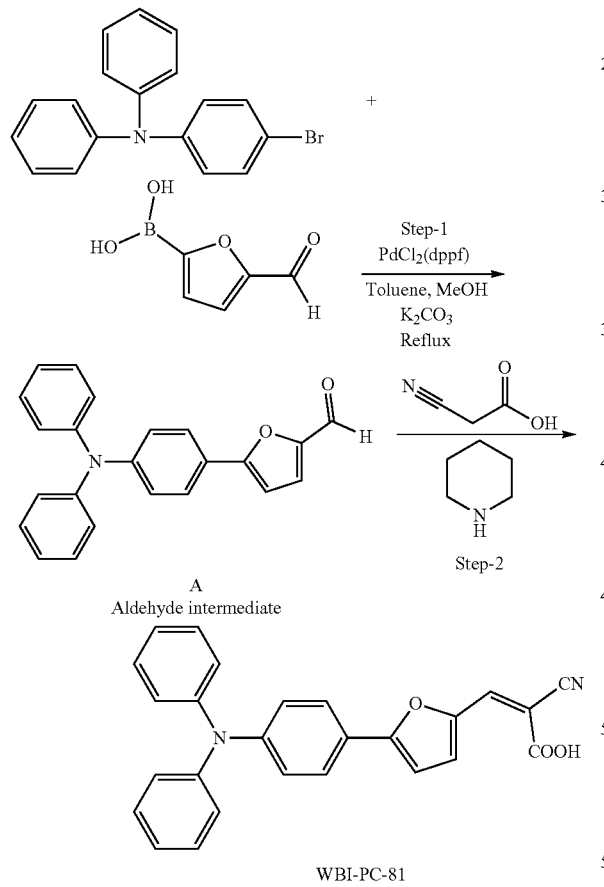

Synthesis of Aldehyde Intermediate A

A mixture of 4-bromo-N,N-diphenyl-aniline (1.0 g, 3.08 mmol), PdCl2(dppf) (250 mg, 10 mol %), K2CO3 (2.12 g, 5 equiv.) were combined with 15 mL of dry toluene in a Schlenck tube and stirred under $N_2$ for 15 min at room temperature. The mixture was treated with (5-formyl-2-furyl) boronic acid (964 mg, 2 equiv.) in dry MeOH (5 mL), and the reaction was refluxed for 18 hours under $N_2$. The mixture was then cooled to room temperature and the solvents were removed under reduced pressure. The resulting residue was treated with DI water (20 mL) and extracted with DCM (50 mL). The organic layer was sequentially washed with DI water (20 mL), 1N HCl (25 mL) and saturated brine solution (25 mL). The organic layer was concentrated under reduced pressure and purified on silica gel using Hexanes:EtOAc as eluent to afford 5-[4-(N-phenylanilino)phenyl]furan-2-carbaldehyde (A) as a yellow red solid (900 mg, 82% yield).

Synthesis of WBI-PC-81

5-[4-(N-phenylanilino)phenyl]furan-2-carbaldehyde A (640 mg, 1.80 mmol) was combined with cyanoacetic acid (382 mg, 2.5 eq) and piperidine (0.931 mL, 2.1 eq with respect to cyanoacetic acid) in 10 mL of dry MeCN. The reaction was refluxed for 4 hours whereby the TLC indicated consumption of all starting material. The reaction was cooled down to room temperature and the MeCN was removed under reduced pressure. To the residue was added EtOAc (50 mL), washed with DI water (50 mL) followed by 0.1 N HCl (50 mL). The organic layer was separated, concentrated and then the crude mixture was then purified using a silica gel column using DCM: MEOH as eluent to afford WBI-PC-81 as a dark red solid (600 mg, 79% yield). LCMS (M+1): 407.1; 1HNMR (400 MHz, d6-DMSO) 7.99 (s, 1H), 7.77 (s, 2H), 7.60 (s, 1H), 7.40 (m, 4H), 7.22-7.08 (m, 7H), 6.94 (s, 2H).

Example 5

Synthesis of 7-[(E)-2-[4-(4-tert-butyl-N-(4-tert-butylphenyl)anilino)phenyl]vinyl]-2-oxo-1H-quinoline-3-carbonitrile (WBI-PC-174)

Synthetic Scheme

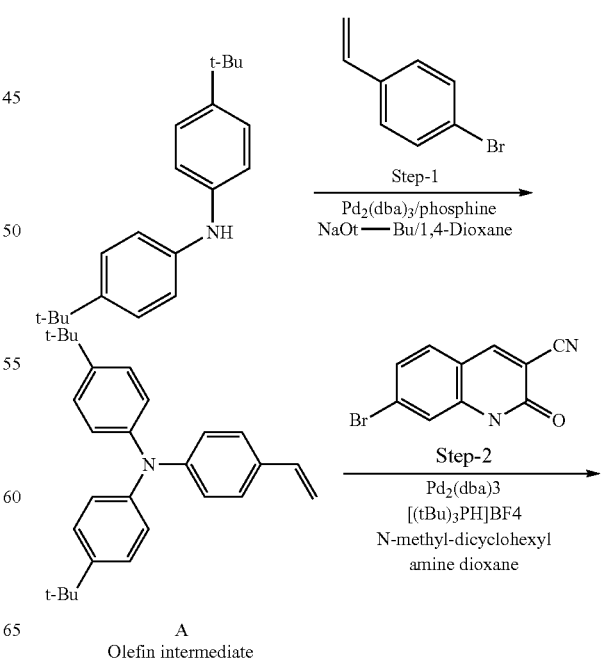

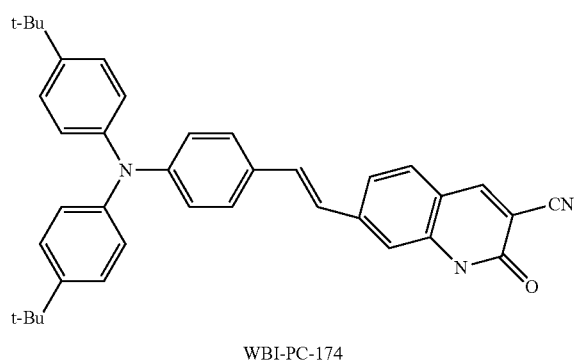

WBI-PC-174

Synthesis of Olefin Intermediate A

To a mixture of Bis((4-t-butyl)phenyl)amine (15.0 g, 0.053 mol) and 4-bromostyrene (~7 mL, 1 equiv.) in an oven dried 500 mL Schlenck flask was added Pd$_2$(dba)$_3$ (488 mg, 0.533 mmol), phosphine (360 mg, 1.06 mmol) and NaOtBu (5.63 g, 0.059 mol). The flask was flushed with N$_2$ for 10 min and treated with degassed 1,4-dioxane (50 mL) was added, and the mixture was heated at 80° C. for 1.5 hours under N$_2$. The reaction was monitored by TLC for completion before cooling to room temperature. The organic layer was washed with DI water (2×100 mL) and then saturated brine solution (100 mL). The organic layer was then dried over anhydrous Na$_2$SO$_4$ and concentrated under reduced pressure. The resulting crude olefin product was used in the following step without further purification.

Synthesis of WBI-PC-174

1.0 equiv. of 7-bromo-2-oxo-1H-quinoline-3-carbonitrile, 0.025 equiv. Pd$_2$(dba)$_3$ and 0.05 equiv. tBu3PHBF4 were added to 1.0 equiv. of N,N-bis(4-tert-butylphenyl)-4-vinylaniline in a round bottom flask. The flask was purged with N$_2$ for 20 min. Dry dioxane was degassed by bubbling with N$_2$ for 20 minutes. Dioxane was added to the reaction (0.2 M) followed by 1.5 equiv. N-methyl-di-cyclohexylamine. The solution was heated to 65° C. and monitored by LCMS, TLC 30% ethyl acetate/hexane. After 1.5 hours, the reaction had solidified. 4.0 mL of N$_2$ degassed dry dioxane were added to re-dissolve the material and the styrene was consumed within 2.5 hours as indicated by TLC. The reaction mixture, a solid mass, was cooled to room temperature, residual solvent was removed under reduced pressure. The crude reaction product was partitioned between 50 mL of CH$_2$Cl$_2$ and 20 mL of 1M HCl and the insoluble material was filtered off. The layers were separated and the aqueous layer was back extracted 2×25 mL of CH$_2$Cl$_2$. The combined organic layer was dried over Na$_2$SO$_4$, filtered and concentrated under reduced pressure to afford WBI-PC-174. 1HNMR (400 MHz, d6-DMSO) 8.10 (s, 1H), 7.60-6.91 (m, 17H), 1.26 (s, 18H).

General Synthetic Scheme for Making Compounds with Acid Linkers

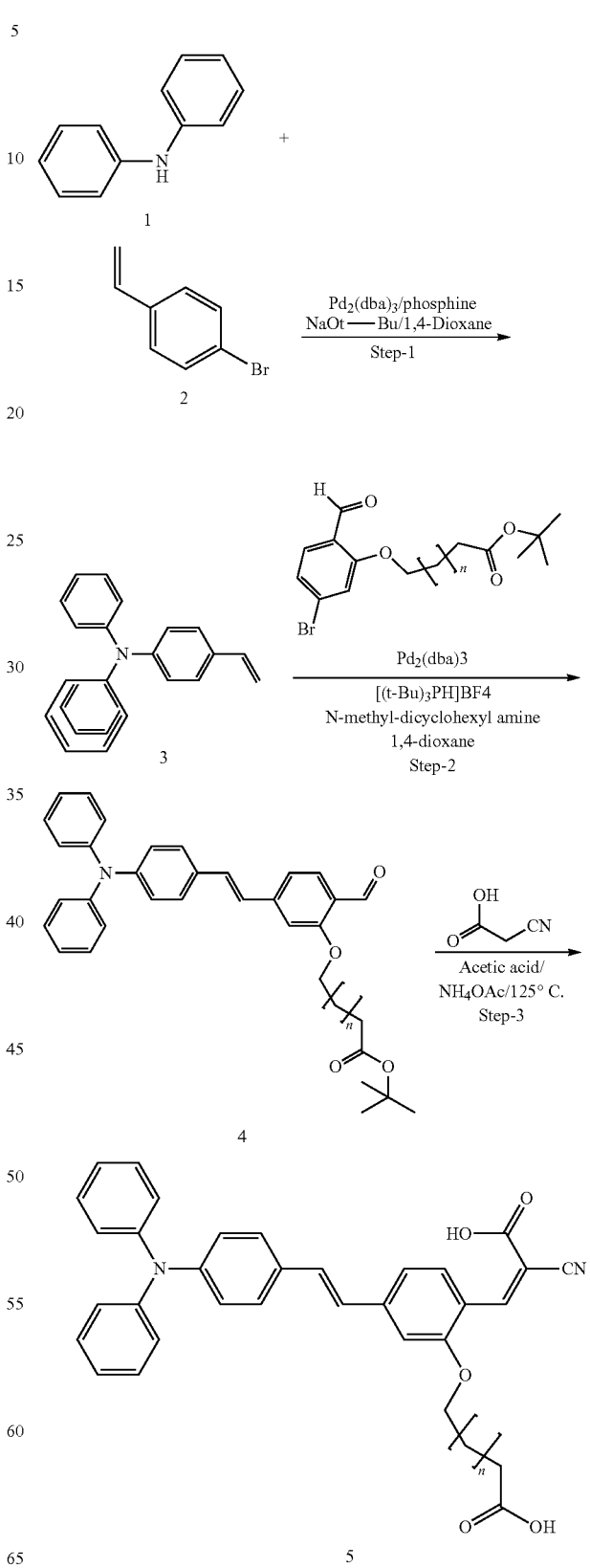

Example 6
Synthesis of (Z)-3-[2-(carboxymethoxy)-4-[(E)-2-[4-(N-phenylanilino)phenyl]vinyl]phenyl]-2-cyano-prop-2-enoic acid (WBI-PC-78)
Synthetic Scheme
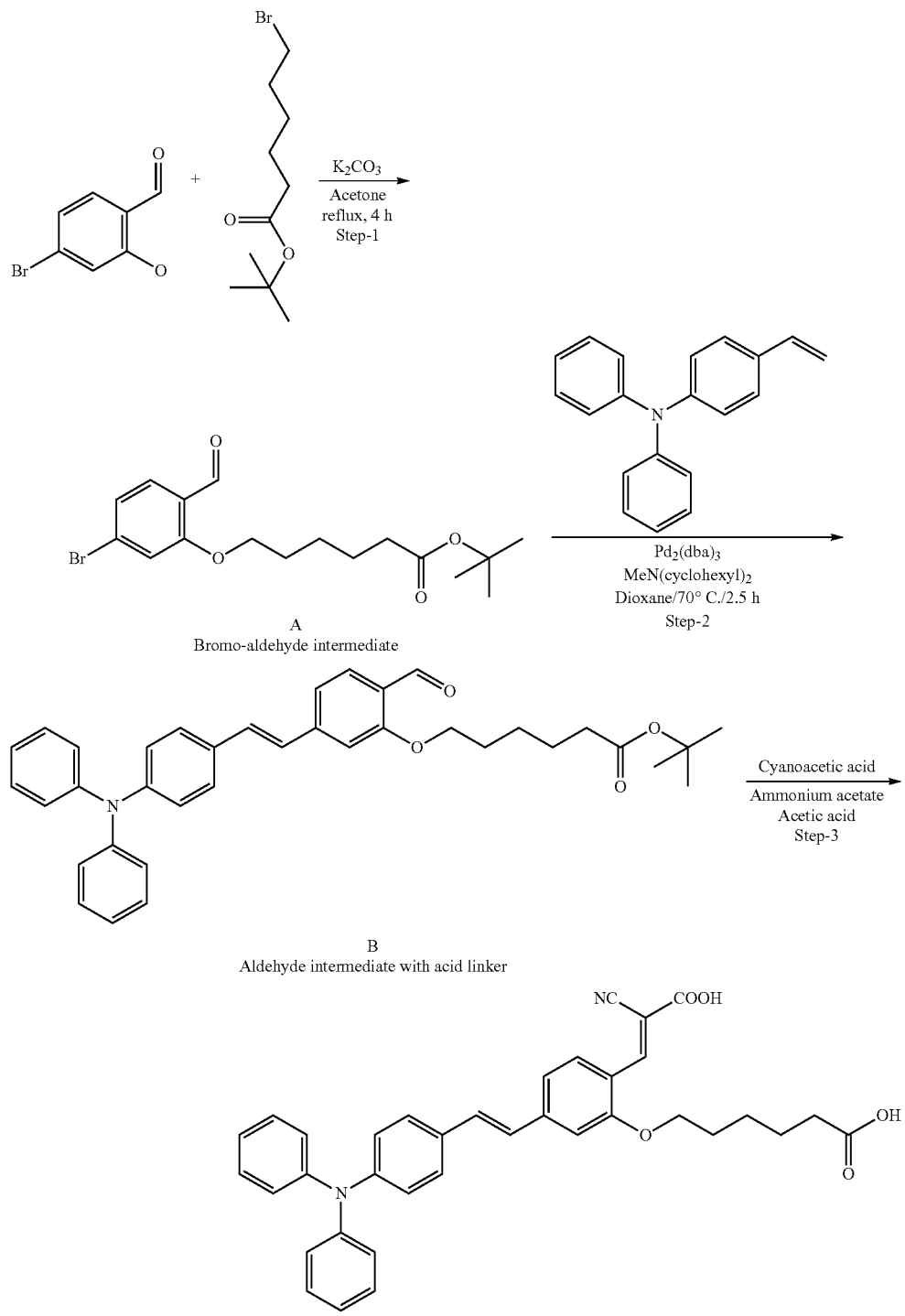
A
Bromo-aldehyde intermediate
B
Aldehyde intermediate with acid linker
WBI-PC-190

Synthesis of the Bromoaldehyde Intermediate with Acid Linker (A)

A mixture of 4-bromo-2-hydroxybenzaldehyde (1.5 g, 7.4 mmol), tert-butyl 6-bromohexanoate (9.0 mmol) and potassium carbonate (3.2 g, 22.5 mmol) were taken in acetone (10 mL). The reaction mixture was refluxed for 4 h. The reaction mixture was extracted with ethyl acetate (2×25 mL), dried over anhydrous $Na_2SO_4$ and concentrated under reduced pressure. Purification on silica gel afforded 1.1 g of the desired compound A as a white solid.

Synthesis of the Aldehyde Intermediate with Acid Linker (B)

To the N,N-diphenyl-4-vinyl-aniline (0.003 mol) in a two necked flask under $N_2$ was added the bromo-aldehyde intermediate A (0.004 mol) and N-methyl-dicylohexyl amine (0.008 mol). $Pd_2(dba)_3$ (0.04 g, 0.044 mmol) and phosphine salt (0.022 g, 0.007 mmol) were then added to the flask under $N_2$. Dry and degassed 1,4-dioxane (10 mL) was added to the flask. The mixture was stirred at 70° C. under $N_2$ for 2.5 hours. The reaction mixture was extracted with ethyl acetate, dried over anhydrous $Na_2SO_4$ and concentrated under reduced pressure. Purification on silica gel afforded 1.4 g of the desired compound B.

Synthesis of WBI-PC-78

In a 20 mL microwave tube, the intermediate B (3 mmol), 2-cyanoacetic acid (5.1 mmol) and ammonium acetate (8 mmol) were mixed in acetic acid (15 mL). The reaction mixture was heated at 130° C. for 90 min. Water (10 mL) was added, and the solid was filtered, and dried under reduced pressure to give the product WBI-PC-78. LCMS (M+1): 559.7; 1H NMR (400 MHz, d6-DMSO) 8.54 (s, 1H), 8.17 (s, 1H), 7.32-7.30 (m, 9H), 7.06-7.03 (m, 9H), 4.19 (t, 2H), 2.47 (t, 2H), 1.88-1.66 (m, 4H).

Example 7

Synthesis of (Z)-3-[2-(carboxymethoxy)-4-[(E)-2-[4-(N-phenylanilino)phenyl]vinyl]phenyl]-2-cyano-prop-2-enoic acid WBI-PC-190

Synthetic Scheme

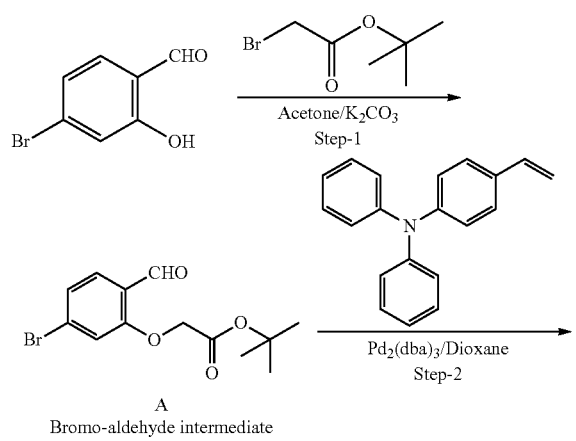

A
Bromo-aldehyde intermediate

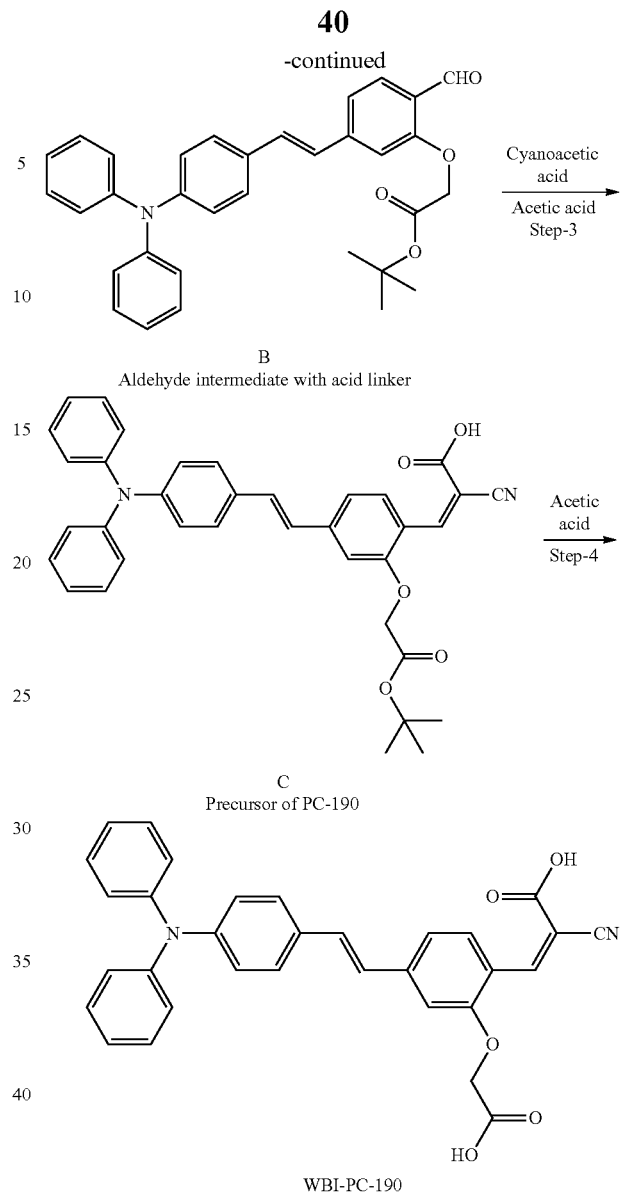

Synthesis of the Bromoaldehyde Intermediate with Acid Linker

In a 250 mL round bottom flask, 4-bromo-2-hydroxybenzaldehyde (3 g, 14.9 mmol), tert-Butyl bromoacetate (3.49 g, 17.9 mmol) and potassium carbonate (6.19 g, 44.8 mmol) were dissolved in acetone (30 mL). The reaction mixture was refluxed for 4 hours. The reaction mixture was then extracted with ethyl acetate (2×25 mL), dried over anhydrous $Na_2SO_4$ and concentrated under reduced pressure. Purification on silica gel afforded 2.8 g (59% yield) of the desired compound A as white solid. 1H NMR (400 MHz, CDCl3): 10.46 (s, 1H), 7.71 (d, 1H), 7.24 (s, 1H), 6.99 (s, 1H), 4.61 (s, 2H), 1.47 (s, 9H).

Synthesis of the Aldehyde Intermediate with Acid Linker

To the N,N-diphenyl-4-vinyl-aniline (2 g, 0.007 mol) in a two necked flask under $N_2$ was added 4-bromo-2,5-dimethoxy benzaldehyde (2.44 g, 0.008 mol) and N-methyl-dicyclohexyl amine (3.3 mL, 0.016 mol). Pd$_2$(dba)$_3$ (0.081 g, 0.088 mmol) and phosphine salt (0.043 g, 0.0014 mmol) were then added to the flask under N$_2$. Dry and degassed 1,4-dioxane (10 mL) was added to the flask. The mixture was stirred at 70° C. under N$_2$ for 2.5 hours. The mixture turned from purple to yellow green upon stirring. TLC analysis (Hex:Ethyl acetate 10:1) after 2.5 hours showed complete consumption of 4-bromo-2,5-dimethoxy benzaldehyde and the formation of the desired product (confirmed by LCMS). The reaction mixture was extracted with ethyl acetate, dried over anhydrous Na$_2$SO$_4$ and evaporated. Purification by combiflash afforded 2.2 g of desired compound B. LCMS (M+1): 505.9; 1H NMR (400 MHz, CDCl3): 10.48 (s, 1H), 7.80 (d, 1H), 7.40-7.04 (m, 19H), 6.99 (s, 1H), 4.67 (s, 2H), 1.47 (s, 9H).

Synthesis of WBI-PC-190

In a 20 mL microwave tube, tert-butyl 2-[2-formyl-5-[(E)-2-[4-(N-phenylanilino)phenyl]vinyl]-phenoxy]-acetate (1.3 g, 3 mmol), 2-cyanoacetic acid (0.46 g, 5.1 mmol) and ammonium acetate (0.595 g, 8 mmol) were mixed in 15 mL of acetic acid. The reaction mixture was heated at 130° C. for 20 min. LCMS showed desired mass peak along with tertiary group deprotected product. Water (10 mL) was added, and the solid was filtered, and dried under reduced pressure to give the product WBI-PC-190 (0.6 g, 83% yield) red solid. LCMS (M+1): 516.6; 1H NMR (400 MHz, d6-DMSO): 8.60 (s, 1H), 8.18 (s, 1H), 7.34-6.98 (m, 20H), 4.92 (s, 2H).

Example 8

Synthesis of WBI-PC-191

Synthesis of tert-Butyl-8-bromooctanoic acid Intermediate

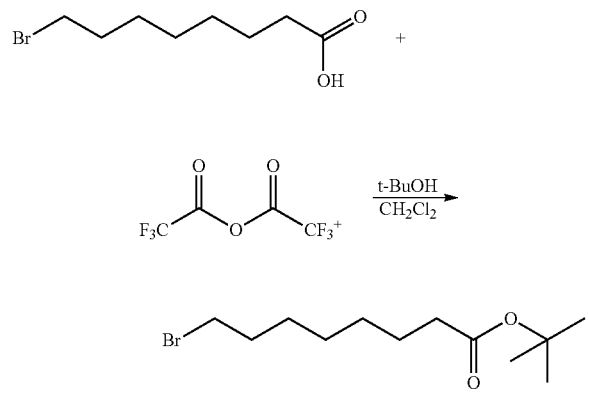

To a solution of 8-bromooctanoic acid (5 g, 22 mmol) in DCM (20 mL) was added TFAA (10.36 g, 49 mmol) dropwise at 0° C. After 2.5 hours, t-BuOH (5.81 g, 70 mmol) was slowly added. After 1 hour, the reaction had warmed to rt. After 2.5 hours, the reaction was quenched with H2O (10 mL) and extracted with ethyl acetate (2×20 mL). The combined organic layer was washed with brine and dried over MgSO$_4$, filtered, and concentrated under reduced pressure. The crude (6.89 g) was used in the next step without further purification.

Synthesis of the aldehyde Intermediate by O-alkylation of 4-bromo-2-hydroxy-benzaldehyde with tert-butyl ester Linker

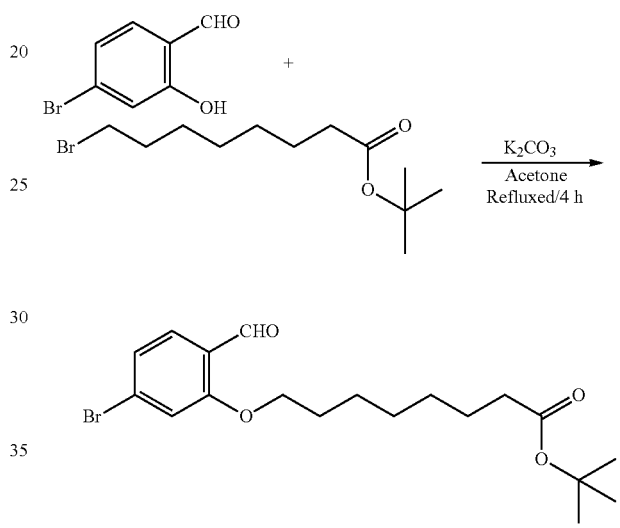

In a single necked round bottom flask, 4-bromo-2-hydroxy-benzaldehyde (3 g, 0.015 mol), tert-butyl 8-bromooctanoate (4.16 g, 0.015 mol) and K2CO3 (4.12 g, 0.03 mol) were dissolved in dry DMF (30 mL). The reaction mixture was heated at 70° C. for 16 hours. LCMS showed the desired mass peak. The crude reaction mixture was extracted with ethyl acetate, washed with water, dried over anhydrous Na$_2$SO$_4$ and concentrated under reduced pressure. Purification on silica gel using Hexane/Ethyl acetate (97:3) afforded 2.4 g (40% yield) of desired product. 1H NMR (400 MHz, CDCl3): 10.39 (s, 1H), 7.67 (d, 1H), 7.11 (d, 2H), 4.03 (t, 2H), 2.21 (t, 2H), 1.80-1.23 (m, 10H), 1.41 (s, 9H).

Synthesis of the triphenylamine styryl aldehyde Intermediate tert-butyl ester Linker Product

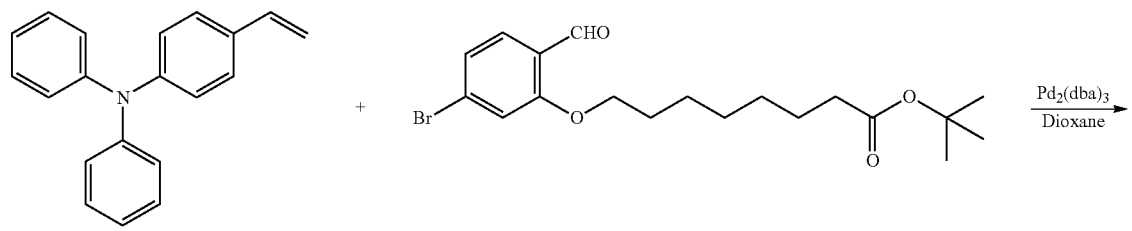

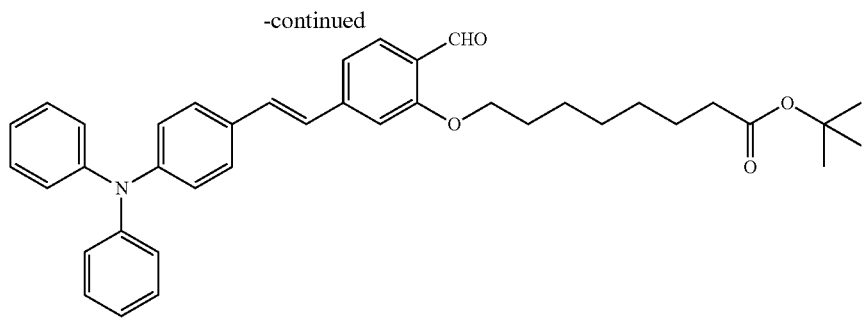

To the N,N-diphenyl-4-vinyl-aniline (2 g, 0.007 mol) in a two necked flask under $N_2$ was added tert-butyl 8-(5-bromo-2-formyl-phenoxy)octanoate (3.09 g, 0.008 mol) and N-methyl-dicylohexyl amine (3.05 g, 0.0.016 mol). $Pd_2(dba)_3$ (0.081 g, 0.088 mmol) and phosphine salt (0.043 g, 0.0014 mmol) were then added to the flask under $N_2$. Dry and degassed 1,4-dioxane (10 mL) was added to the flask. The mixture was stirred at 70° C. under $N_2$ for 2.5 hours. The mixture turned from purple to yellow green upon stirring. TLC analysis (Hexane:Ethyl acetate 10:1) after 2.5 hours showed complete consumption of tert-butyl 8-(5-bromo-2-formyl-phenoxy)octanoate and the formation of the desired product (confirmed by LCMS). Purification on silica gel afforded 2.3 g (50% yield) of the desired product. 1H NMR (400 MHz, CDCl3): 10.40 (s, 1H), 7.66 (d, 1H), 7.13 (d, 2H), 4.04 (t, 2H), 2.19 (t, 2H), 1.81-1.28 (m, 14H), 1.41 (s, 9H).

Synthesis of the cyanoacrylic acid Intermediate by Knoevenagel Condensation

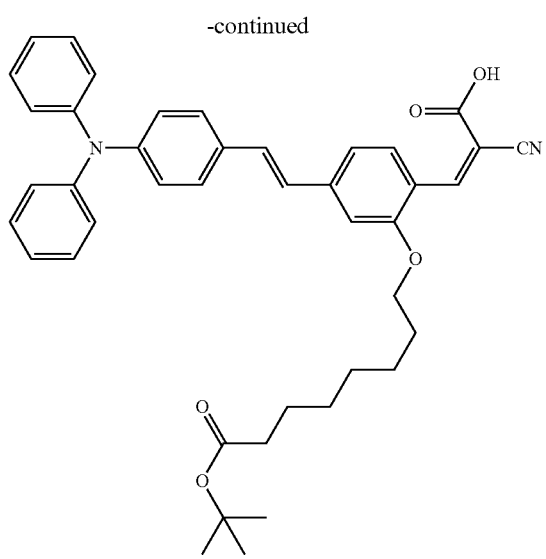

In a 20 mL microwave tube, tert-butyl 8-[2-formyl-5-[(E)-2-[4-(N-phenylanilino)phenyl]vinyl]phenoxy]octanoate (1.5 g, 3 mmol), 2-cyanoacetic acid (0.454 g, 5 mmol) and ammonium acetate (0.588 g, 8 mmol) were dissolved in 15 mL of acetic acid. The reaction mixture was heated at 130° C. for 20 min. LCMS showed the desired mass peak along with tertiary group deprotected product. Water (10 mL) was added and filtered. The collected solid was used in the next step without further purification.

Synthesis of WBI-PC-191 by tert-butyl Deprotection

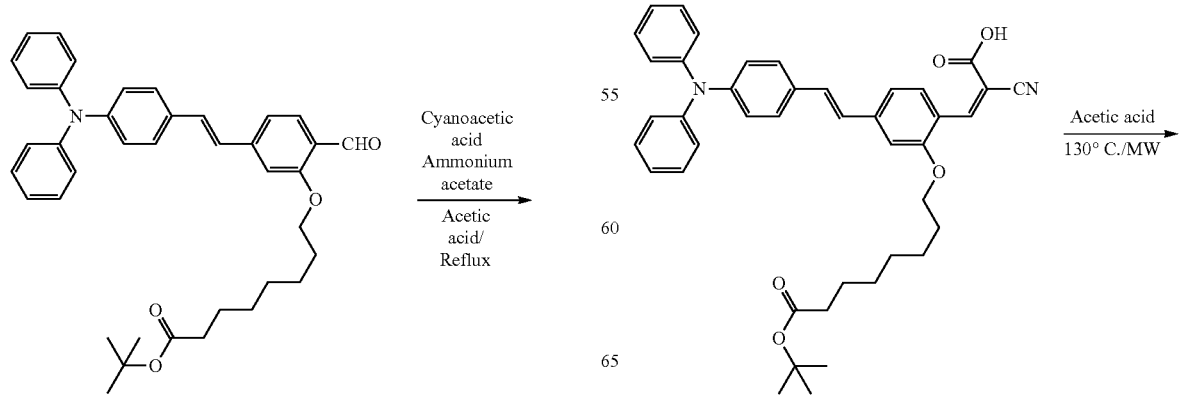

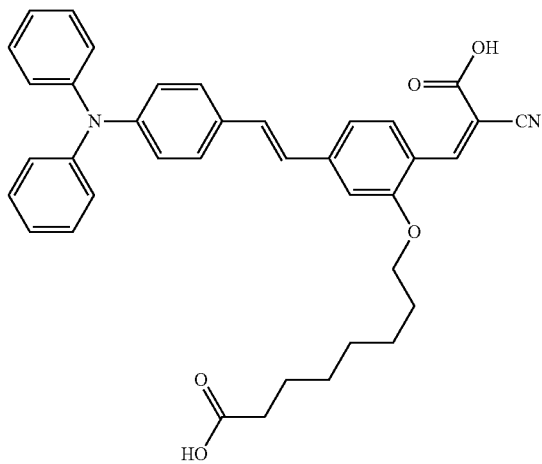

In a 20 mL microwave tube, (Z)-3-[2-(8-tert-butoxy-8-oxo-octoxy)-4-[(E)-2-[4-(N-phenylanilino)phenyl]vinyl]phenyl]-2-cyano-prop-2-enoic acid (1 g, 1.52 mmol) was dissolved in 10 mL acetic acid and 1 mL water. The reaction mixture was heated at 130° C. for 20 min. The reaction was repeated two times for 20 min each in the microwave. LCMS showed the desired mass peak. Water (10 mL) was added and filtered. The collected solid was dried under reduced pressure to give WBI-PC-191 0.650 g (61% yield) as a red solid. LCMS (M+1): 600.7; 1H NMR (400 MHz, d6-DMSO): 8.56 (s, 1H), 8.18 (s, 1H), 7.60-6.91 (m, 20H), 4.16 (br s, 2H), 2.18 (br s, 2H), 1.89 (br s, 2H), 1.58-1.20 (m, 8H).

Example 9

Synthesis of WBI-PC-192

Synthesis of the tert-Butyl-10-bromodecanoic acid Intermediate

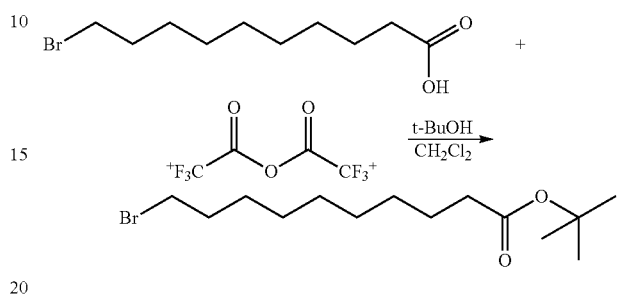

To solution of 10-bromdectanoic acid (5 g, 20 mmol) in DCM (20 mL) was added TFAA (9.2 g, 44 mmol) dropwise at 0° C. After 2.5 hours, t-BuOH (5.16 g, 70 mmol) was slowly added. After 1 hour the reaction had warmed to RT. After 2.5 hours, the reaction was quenched with H2O (5 mL) and extracted with ethyl acetate (2×20 mL). The combined organic layer was washed with brine and dried over MgSO4, filtered, and concentrated under reduced pressure. The crude (6.12 g) was used in the next step without further purification.

Synthesis of the aldehyde Intermediate by O-alkylation of 4-bromo-2-hydroxy-benzaldehyde with tert-butyl ester Linker

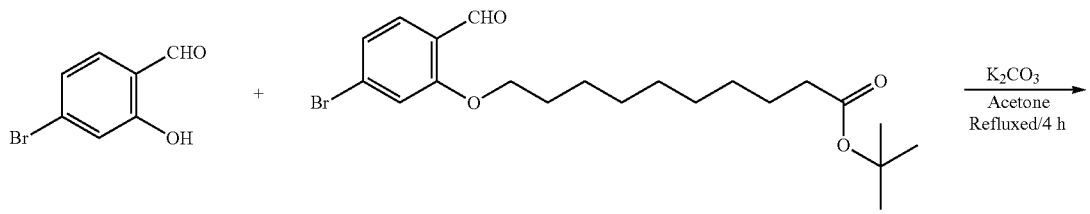

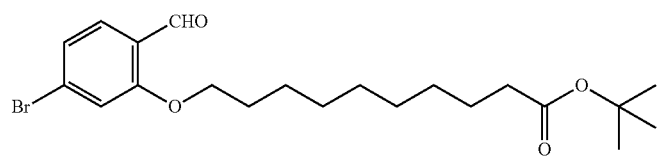

In a single necked round bottom flask, 4-bromo-2-hydroxy-benzaldehyde (3 g, 0.015 mol), tert-butyl 10-bromo-decanoate (5.04 g, 0.016 mol) and K2CO3 (6.18 g, 0.045 mol) were dissolved in dry DMF (30 mL). The reaction mixture was heated at 70° C. for 16 hours. LCMS showed the desired mass peak. The crude reaction mixture was extracted with ethyl acetate, washed with water, dried over anhydrous $Na_2SO_4$ and concentrated under reduced pressure. Purification on silica gel afforded 3.2 g (50% yield) of the desired product.

Synthesis of the triphenylamine styryl aldehyde intermediate tert-butyl ester Linker

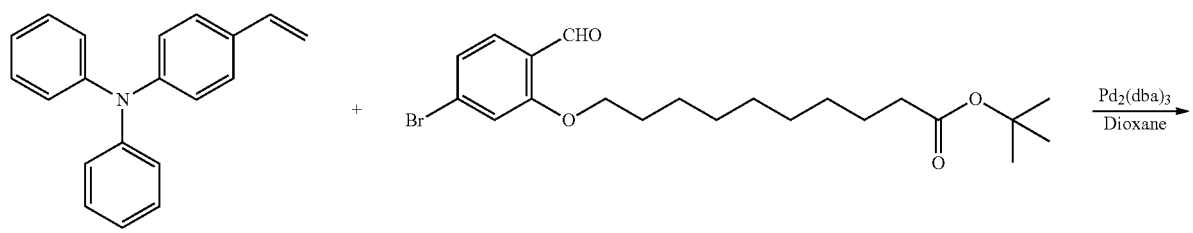

To the N,N-diphenyl-4-vinyl-aniline (2 g, 7.74 mmol) in a two necked flask under $N_2$ was added tert-butyl 10-(5-bromo-2-formyl-phenoxy)decanoate (3.307 g, 7.75 mmol) and N-methyl-dicyclohexyl amine (3.05 g, 15.56 mmol). $Pd_2(dba)_3$ (0.081 g, 0.8 mmol) and tri-tert-butylphosphonium tetrafluoroborate (0.043 g, 1.4 mmol) were then added to the flask under $N_2$. Dry and degassed 1,4-dioxane (10 mL) was added to the flask. The mixture was stirred at 70° C. under $N_2$ for 2.5 hours. The mixture turned from purple to yellow green upon stirring. TLC analysis (Hexane:Ethyl acetate 10:1) after 2.5 hours showed complete consumption of tert-butyl 10-(5-bromo-2-formyl-phenoxy)decanoate and the formation of the desired product (confirmed by LCMS). Purification on silica gel afforded 2.3 g of desired product as a yellow liquid. 1H NMR (400 MHz, d6-DMSO): 10.43 (s, 1H), 7.82 (s, 1H), 7.41-6.98 (m, 16H), 4.10 (t, 2H), 2.20 (t, 2H), 1.90-1.209 (m, 14H), 1.42 (s, 9H).

Synthesis of the cyanoacrylic acid intermediate by Knoevenagel Condensation

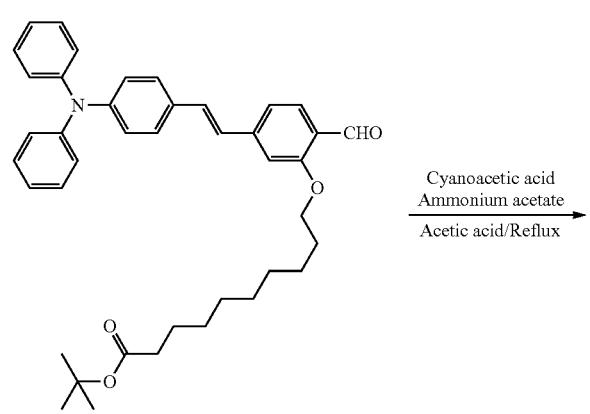

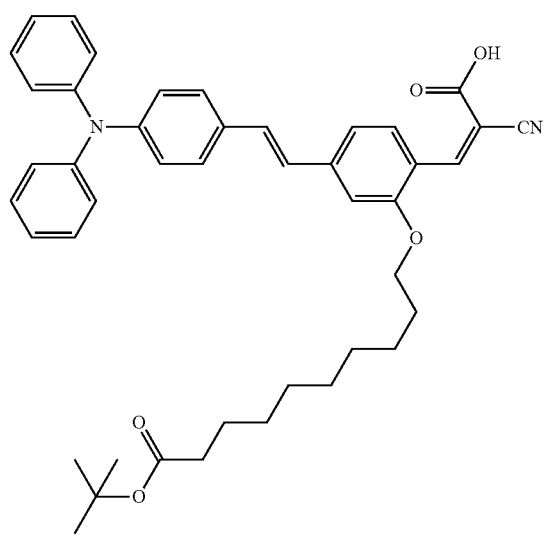

In a 20 mL microwave tube, tert-butyl 10-[2-formyl-5-[(E)-2-[4-(N-phenylanilino)phenyl]vinyl]phenoxy]-decanoate (1.5 g, 2.43 mmol), 2-cyanoacetic acid (0.434 g, 5.1 mmol) and ammonium acetate (0.561 g, 7.23 mmol) were dissolved in 15 mL acetic acid. The reaction mixture was heated at 130° C. for 20 min. LCMS showed the desired mass peak along with the tertiary group deprotected product. Water (10 mL) was added and filtered. The collected solid was used in the next step without further purification.

Synthesis of WBI-PC-192 by tert-butyl Deprotection

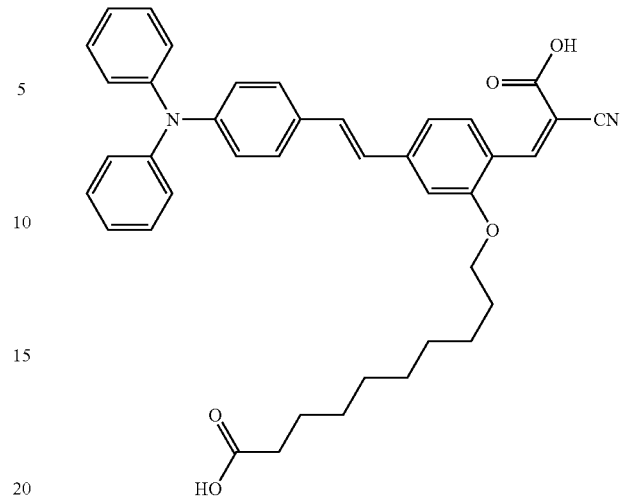

In a 20 mL microwave tube, (Z)-3-[2-(10-tert-butoxy-10-oxo-decoxy)-4-[(E)-2-[4-(N-phenylanilino)-phenyl]vinyl]phenyl]-2-cyano-prop-2-enoic acid(0.9 g, 1.31 mmol) was dissolved in 20 mL of acetic acid. The reaction mixture was heated at 130° C. for 20 min. The reaction was repeated two times for 20 min each in the microwave. LCMS showed the desired mass peak. Water (10 mL) was added and filtered. The collected solid was dried under reduced pressure to give 0.650 g (61% yield) of WBI-PC-192 as a red solid. LCMS (M+1): 628.7; 1H NMR (400 MHz, d6-DMSO): 8.54 (s, 1H), 8.19 (s, 1H), 7.61-6.90 (m, 20H), 4.18 (br s, 2H), 2.20 (br s, 2H), 1.88 (br s, 2H), 1.58-1.20 (m, 12H).

Example 10

Synthesis of BC-146 and -147

The two compounds BC-146 [2-cyano-3-(6-(diphenylamino)benzofuran-2-yl)acrylic acid] and BC-147 [2-cyano-3-(4-(6-(diphenylamino)benzofuran-2-yl)phenyl) acrylic acid] were synthesized from common intermediate 3-hydroxytriphenylamine. The 3-hydroxy functional group on triphenylamine enables a cyclization that incorporates one of the three phenyl groups as the benzo ring of the benzofuran.

A. Synthesis of 3-Hydroxytriphenylamine

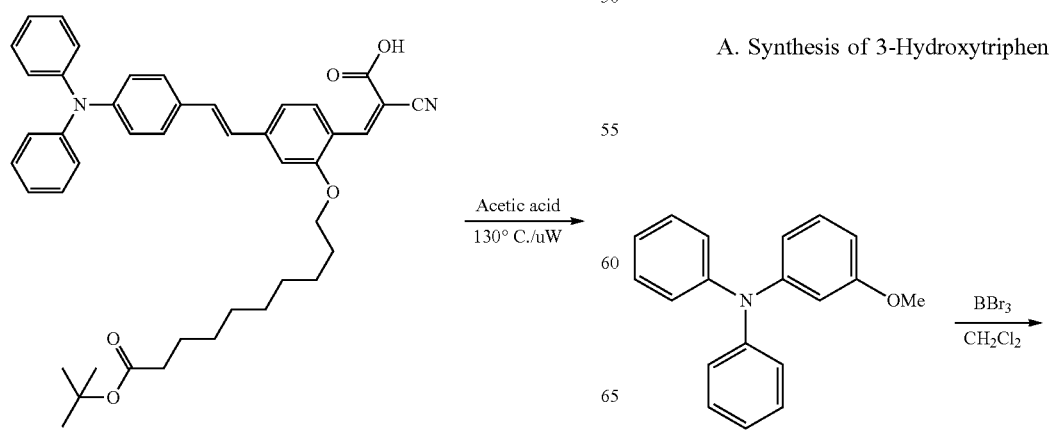

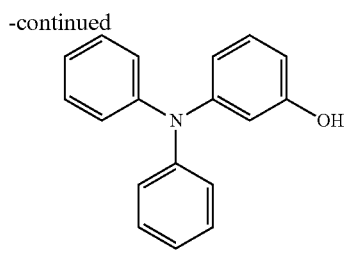

The synthesis of 3-hydroxytriphenylamine was adapted from a procedure reported by M.-k. Leung et al., Organic Letters (2006) 8:2623-2626. To a nitrogen purged flask containing 3-methoxytriphenylamine (2.90 g) was added anhydrous dichloromethane (21 mL). The reaction was cooled to −78° C. and boron tribromide (1.0 M in dichloromethane, 21 mL) was added dropwise over 10 minutes via syringe. The reaction was allowed to warm to room temperature slowly over 18 hours. The reaction was quenched by the careful addition of a 10% aqueous solution of potassium carbonate. The reaction was then allowed to stir at room temperature for 20 minutes before being extracted with dichloromethane (2×50 mL). The combined extract was washed with brine, dried over magnesium sulfate, filtered, and concentrated to afford 3-hydroxytriphenylamine (2.75 g) which was used without further purification. $^1$H NMR (400 MHz, Chloroform-d) δ 7.27-7.21 (m, 4H), 7.11-7.05 (m, 5H), 7.04-6.98 (m, 2H), 6.63 (ddd, 1H), 6.52 (t, 1H), 6.45 (ddd, Hz, 1H), 4.50 (broad s, 1H).

B. Synthesis of 4-(Diphenylamino)-2-hydroxybenzaldehyde

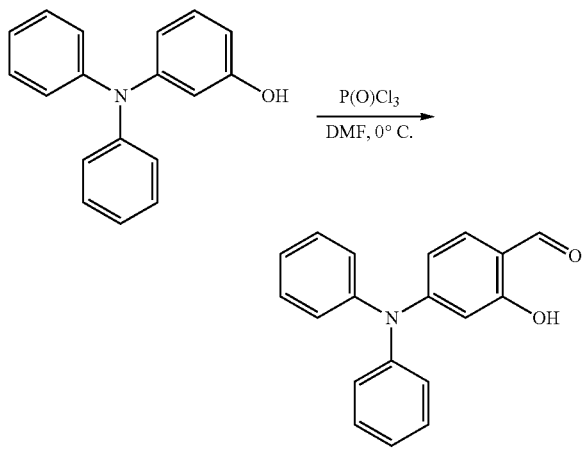

A solution of 3-hydroxytriphenylamine (1.47 g) in anhydrous N,N-dimethylformamide (28 mL) was cooled to 0° C. In a separate flask, phosphorous oxychloride (1.57 mL) was added dropwise to N,N-dimethylformamide (28 mL) at 0° C. After 10 minutes, the phosphorous oxychloride solution was added dropwise to the reaction via cannula over 20 minutes. The reaction mixture was stirred at 0° C. for 3 hours then quenched by the addition of water (20 mL) and warmed to room temperature. The aqueous mixture was extracted with dichloromethane (4×50 mL), and then the combined dichloromethane fractions washed with water (50 mL) and brine (50 mL). The dichloromethane solution was dried over magnesium sulfate, filtered and concentrated. The residue was purified via chromatography on silica gel (elution with 0 to 10% ethyl acetate in hexanes) to afford 4-(diphenylamino)-2-hydroxybenzaldehyde (1.07 g). $^1$H NMR (400 MHz, Chloroform-d) δ 11.40 (s, 1H), 9.59 (s, 1H), 7.35 (dd, 4H), 7.22-7.15 (m, 7H), 6.46 (dd, 1H), 6.34 (d, 1H).

C. Synthesis of 2-(2,2-Diethoxyethoxy)-4-(diphenylamino)benzaldehyde

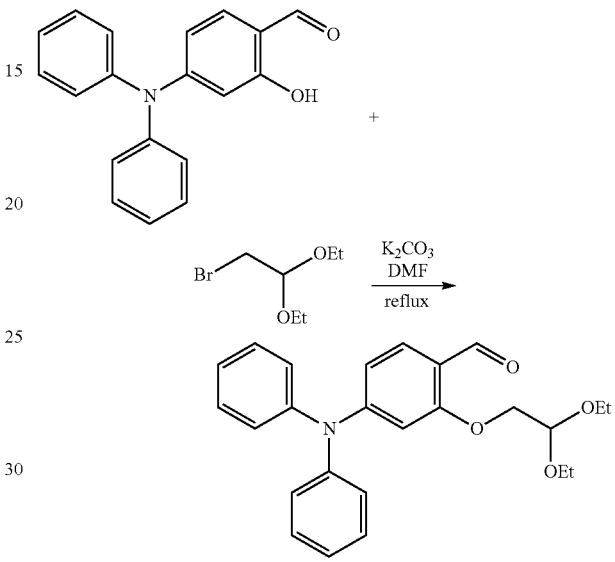

A flask containing 4-(diphenylamino)-2-hydroxybenzaldehyde (0.50 g) and potassium carbonate (0.26 g) was flushed with nitrogen for 20 minutes. Anhydrous N,N-dimethylformamide (3.5 mL) and bromodiethoxyethane (0.33 mL) were added and the reaction heated to 155° C. for 2 hours. The reaction was cooled to room temperature and water added (15 mL). The aqueous layer was extracted with ethyl acetate (3×30 mL) and the combined organic fractions washed with water and brine, dried over sodium sulfate, filtered and concentrated to afford 2-(2,2-diethoxyethoxy)-4-(diphenylamino)benzaldehyde (0.70 g) which was used without further purification. $^1$H NMR (400 MHz, Chloroform-d) δ 10.26 (d, 1H), 7.65 (d, 1H), 7.38-7.27 (m, 4H), 7.21-7.10 (m, 6H), 6.53 (ddd, 1H), 6.42 (d, 1H), 4.79 (t, 1H), 3.83 (d, 2H), 3.79-3.67 (m, 2H), 3.59 (m, 2H), 1.21 (t, 6H).

D. Synthesis of 6-(diphenylamino)benzofuran-2-carbaldehyde

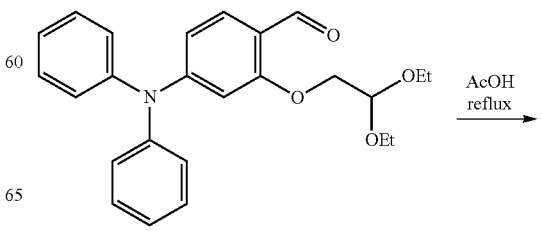

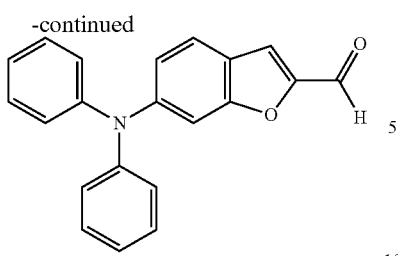

A solution of 2-(2,2-diethoxyethoxy)-4-(diphenylamino)benzaldehyde (0.21 g) in acetic acid (2.5 mL) was heated to reflux. After 5.5 hours, the reaction was cooled to room temperature and diluted with ethyl acetate (30 mL). The organic layer was washed with saturated sodium bicarbonate until the washes remained basic (4×10 mL). The combined aqueous washes were extracted with ethyl acetate (2×30 mL) and the combined organic fractions then washed with saturated sodium bicarbonate and brine. The organic layer was dried over magnesium sulfate, filtered and concentrated. The residue was purified via chromatography on silica gel (elution with 20% ethyl acetate in hexanes) to afford 6-(diphenylamino)benzofuran-2-carbaldehyde (0.12 g). $^1$H NMR (400 MHz, Chloroform-d) δ 9.72 (s, 1H), 7.51 (d, 1H), 7.45 (d, 1H), 7.33-7.26 (m, 4H), 7.17-7.07 (m, 7H), 7.05 (dd, 1H).

E. Synthesis of 2-Cyano-3-(6-(diphenylamino)benzofuran-2-yl)acrylic acid (BC-146)

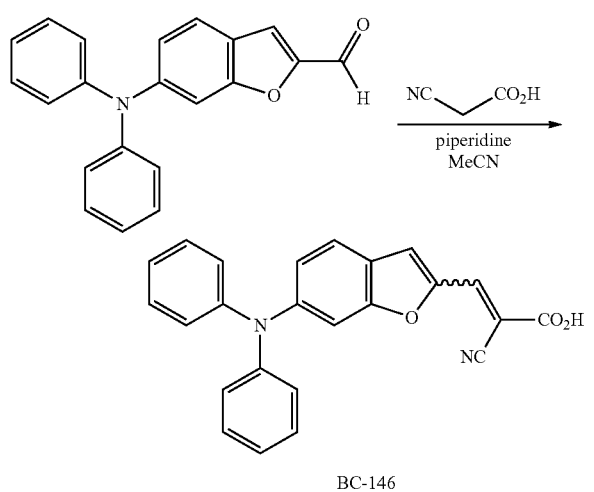

BC-146

To a solution of 6-(diphenylamino)benzofuran-2-carbaldehyde (0.16 g) in acetonitrile (2.6 mL) was added cyanoacetic acid (0.049 g) and piperidine (0.078 mL). The reaction was heated to reflux for 2 hours then cooled to room temperature. Water (10 mL) was added and the pH of the reaction adjusted to 2-3 with 1M HCl. The combined aqueous layer was extracted with dichloromethane (4×20 mL) and then the combined organic fractions dried over sodium sulfate, filtered and concentrated. The solid was dried under vacuum at 60° C. to afford 2-cyano-3-(6-(diphenylamino)benzofuran-2-yl)acrylic acid (BC-146, 0.19 g) as a single, unidentified olefin isomer. $^1$H NMR (400 MHz, DMSO-d6) δ 13.78 (s, 1H), 8.08 (s, 1H), 7.72 (s, 1H), 7.64 (d, 1H), 7.35 (t, 4H), 7.13 (dd, 6H), 6.90 (dd, 1H), 6.84 (s, 1H). Mass (m/z): 381 (M+1)+.

F. Synthesis of 5-(Diphenylamino)-2-iodophenol

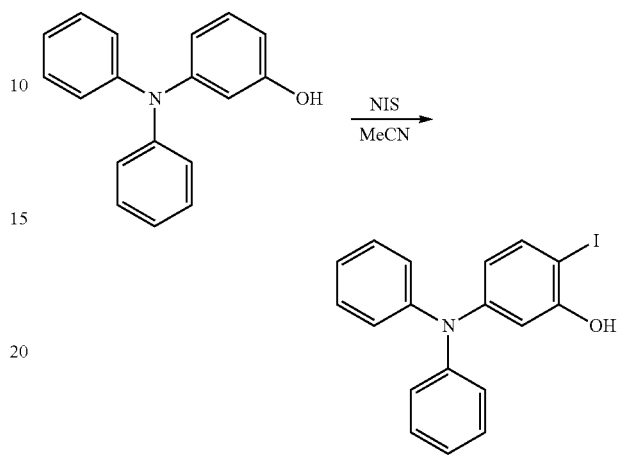

A flask was charged with 3-hydroxytriphenylamine (0.87 g) and N-iodosuccinimide (0.75 g) and purged with nitrogen. Anhydrous acetonitrile (16.6 mL) was degassed by purging with nitrogen, and then added to the reaction mixture. The reaction was stirred at room temperature for 1 hr. The reaction mixture was then concentrated and the residue was then purified via chromatography on silica gel (elution with 0 to 10% ethyl acetate in hexanes) to afford 5-(diphenylamino)-2-iodophenol (1.13 g). $^1$H NMR (400 MHz, Chloroform-d) δ 7.41 (d, 1H), 7.31-7.20 (m, 4H), 7.13-7.04 (m, 4H), 7.04 (s, 2H), 6.68 (d, 1H), 6.42 (dd, 1H), 5.14 (s, 1H).

G. Synthesis of 4-((4-(diphenylamino)-2-hydroxyphenyl)ethynyl)benzaldehyde

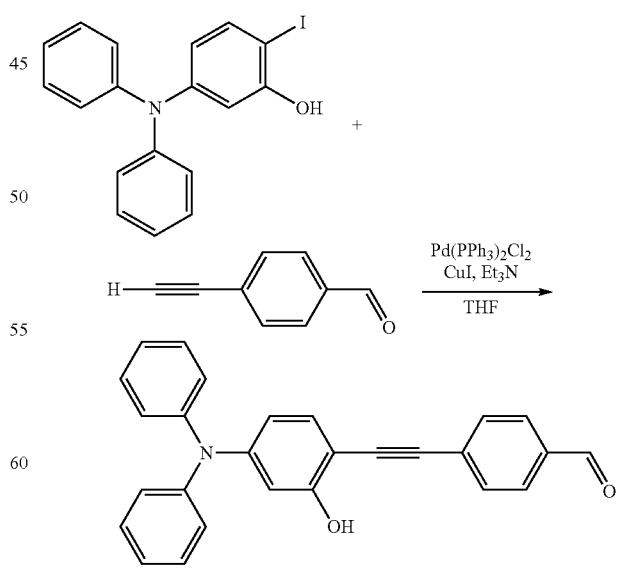

A flask was charged with 5-(diphenylamino)-2-iodophenol (0.14 g), 4-ethynylbenzaldehyde (0.73 g) bis(triphenylphosphine)palladium dichloride (0.008 g), and copper (I) iodide (0.006 g). The flask was purged with nitrogen for 20 minutes. Tetrahydrofuran was degassed by bubbling nitrogen through for 10 minutes, then 1.86 mL added to the reaction. The reaction mixture was stirred at room temperature for 10 minutes, triethylamine (0.10 mL) was added, and then the reaction stirred at room temperature for 3 hours. The reaction was heated to 50° C. for 3 hours, cooled to room temperature and then water (10 mL) and brine (5 mL) were added. The aqueous fraction was extracted with ethyl acetate (3×15 mL). The combined organic fractions were dried over sodium sulfate, filtered, and concentrated. The residue was purified via chromatography on silica gel (elution with 0 to 25% ethyl acetate in hexanes) to afford 4-((4-(diphenylamino)-2-hydroxyphenyl)ethynyl)benzaldehyde (0.094 g). $^1$H NMR (400 MHz, Chloroform-d) δ 10.01 (s, 1H), 7.86 (d, 2H), 7.64 (d, 2H), 7.30 (dd, 4H), 7.16-7.07 (m, 7H), 6.60-6.54 (m, 2H), 5.66 (s, 1H).

H. Synthesis of 4-(6-(Diphenylamino)benzofuran-2-yl)benzaldehyde

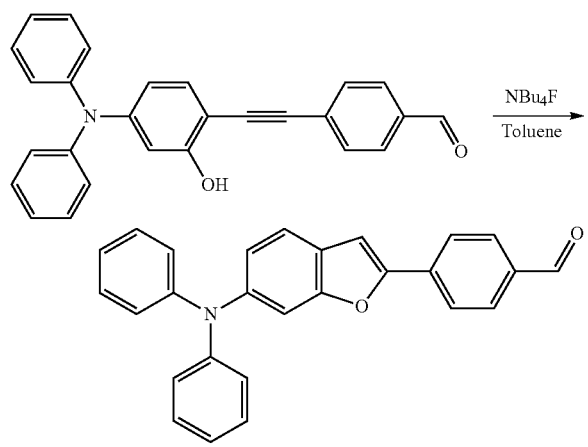

To a nitrogen flushed flask containing 4-((4-(diphenylamino)-2-hydroxyphenyl)ethynyl)benzaldehyde (0.094 g) was added anhydrous toluene (4.85 mL) and tetrabutylammonium fluoride (1.0 M, 0.48 mL). The reaction was heated to 80° C. for 1.5 hours then cooled to room temperature. Water (10 mL) was added and the aqueous layer extracted with ethyl acetate (3×15 mL). The combined organic fractions were washed with brine, dried over magnesium sulfate, filtered and concentrated to afford 4-(6-(diphenylamino)benzofuran-2-yl)benzaldehyde (0.11 g) which was used without further purification. $^1$H NMR (400 MHz, DMSO-d6) δ 9.98 (s, 1H), 8.03 (d, 2H), 7.96 (d, 2H), 7.62 (d, 1H), 7.58 (dd, 1H), 7.29 (dd, 4H), 7.14 (s, 1H), 7.07-7.00 (m, 6H), 6.93 (dd, 1H).

I. Synthesis of 2-cyano-3-(4-(6-(diphenylamino)benzofuran-2-yl)phenyl)acrylic acid (BC-147)

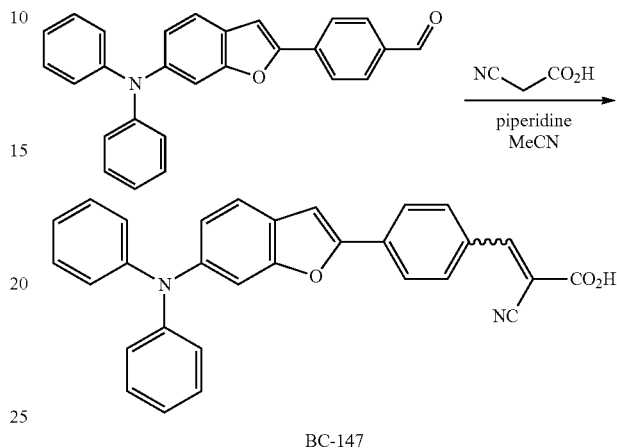

BC-147

To 4-(6-(diphenylamino)benzofuran-2-yl)benzaldehyde (0.048 g) was added acetonitrile (0.61 mL), cyanoacetic acid (0.012 g), and piperidine (0.018 mL). The reaction was heated to reflux for 2.5 hours then cooled to room temperature. Water (10 mL) was added and the aqueous fraction acidified to pH=2 with 1M HCl, then extracted with dichloromethane (3×15 mL). The combined organic fractions were dried over sodium sulfate, filtered, and the filtrate concentrated. The concentrated residue was purified via chromatography on silica gel (elution with 0 to 15% methanol in dichloromethane) to afford 2-cyano-3-(4-(6-(diphenylamino)benzofuran-2-yl)phenyl)acrylic acid (BC-147, 0.034 g) as a single, unidentified olefin isomer. 1H NMR (400 MHz, DMSO-d6) δ 13.96 (s, 1H), 8.22 (s, 1H), 8.07 (d, 2H), 7.99 (d, 2H), 7.57 (d, 2H), 7.29 (t, 4H), 7.12 (s, 1H), 7.04 (t, 6H), 6.93 (dd, 1H). Mass (m/z): 457 (M+1)+.

Example 11

Syntheses of BC-149, -152, -153, -154, -155, -160, -161, -163 and -170

The compounds of this Example (and others herein) were synthesized in accordance with Synthetic Scheme I:

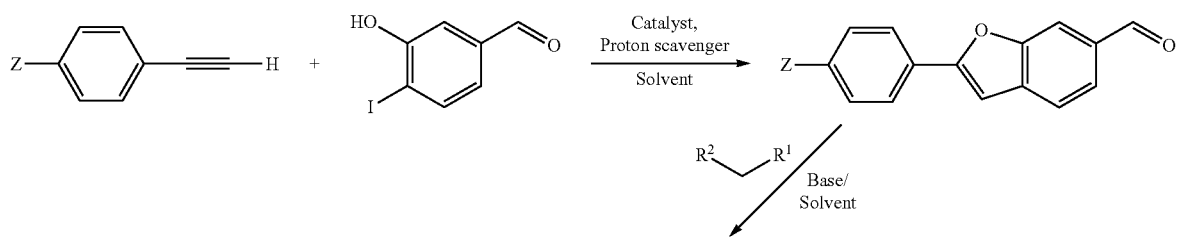

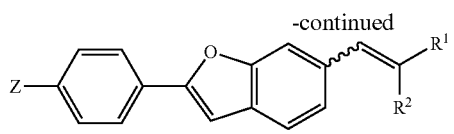

A. Synthesis of Common Intermediate 2-(4-(Diphenylamino)phenyl)benzofuran-6-carbaldehyde

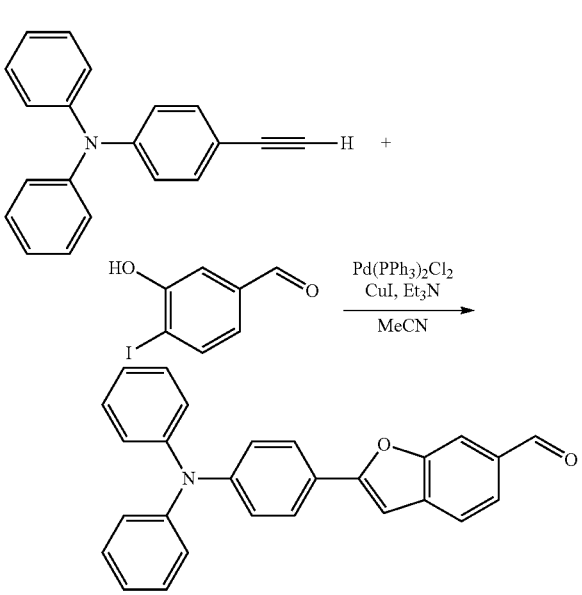

To a 50 mL flask was added 4-ethynyltriphenylamine (1.01 g), 3-hydroxy-4-iodobenzaldehyde (0.77 g), bis(triphenylphosphine)palladium dichloride (0.066 g), and copper (I) iodide (0.054 g). The flask was purged with nitrogen for 20 minutes. A solution of triethylamine (2.18 mL) in anhydrous acetonitrile (15.6 mL) was degassed by bubbling nitrogen through for 20 minutes. The triethylamine solution was added to the reaction and the reaction then heated to 50° C. for 3 hours. The reaction was cooled to room temperature and water (25 mL) added. The aqueous layer was extracted with ethyl acetate (3×30 mL) and the combined organic fractions washed with brine and dried over sodium sulfate. The organic layer was filtered and concentrated. The residue was purified via chromatography on silica gel (elution with 0 to 13% ethyl acetate in hexanes) to afford 2-(4-(diphenylamino)phenyl)benzofuran-6-carbaldehyde (1.08 g). $^1$H-NMR (400 MHz, DMSO-d6): δ 10.04 (s, 1H), 8.11 (d, 1H), 7.86 (d, 2H), 7.80 (s, 2H), 7.42-7.34 (m, 5H), 7.17-7.10 (m, 6H), 7.03 (d, 2H).

B. 2-cyano-3-(2-(4-(diphenylamino)phenyl)benzofuran-6-yl)acrylic acid (BC-149)

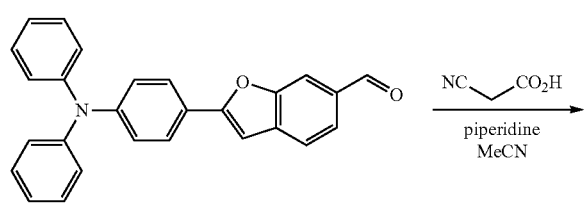

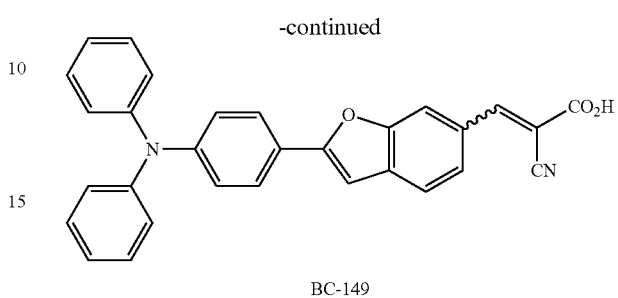

BC-149

Acetic acid (1.70 mL) was added to 2-(4-(diphenylamino)phenyl)-benzofuran-6-carbaldehyde (0.13 g), cyanoacetic acid (0.069 g), and ammonium acetate (0.078 g) and the reaction heated to reflux for 2 hours. The reaction was cooled to room temperature and water (10 mL) added. The reaction was stirred at room temperature for one hour then the precipitate collected by filtration. The solid material was washed with water (50 mL) and hexanes (50 mL) and dried under vacuum at 50° C. to afford 2-cyano-3-(2-(4-(diphenylamino)phenyl)benzofuran-6-yl)acrylic acid (BC-149, 0.14 g) as a single, unidentified olefin isomer. $^1$H NMR (400 MHz, DMSO-d6) δ 13.88 (broad s, 1H), 8.38 (s, 1H), 8.28 (s, 1H), 7.93 (dd, J=8.4, 1.4 Hz, 1H), 7.87-7.79 (m, 2H), 7.75 (d, J=8.3 Hz, 1H), 7.40-7.30 (m, 5H), 7.15-7.06 (m, 6H), 7.01-6.94 (m, 2H). Mass (m/z): 457 (M+1)+.

C. 2-Cyano-3-(2-(4-(diphenylamino)phenyl)benzofuran-6-yl)acrylamide (BC-152)

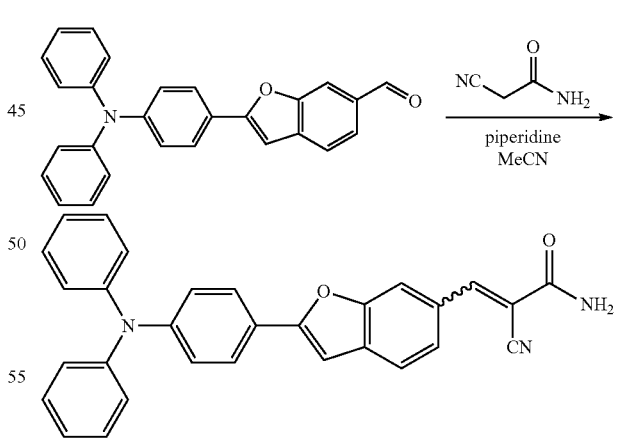

BC-152

To 2-(4-(diphenylamino)phenyl)benzofuran-6-carbaldehyde (0.15 g) and cyanoacetamide (0.035 g) was added acetonitrile (1.9 mL) and piperidine (0.019 mL). The reaction was heated to reflux for 22 hours then cooled to room temperature. Water (10 mL) and dichloromethane (15 mL) were added and the aqueous layer acidified with 1M HCl. The layers were separated and the aqueous fraction extracted with dichloromethane (2×15 mL). The combined organic layers were dried over sodium sulfate, filtered and concentrated. The residue was purified via chromatography on silica gel (elution with 0 to 75% ethyl acetate in hexanes) to afford 2-cyano-3-(2-(4-(diphenylamino)phenyl)benzofuran-6-yl)acrylamide (BC-152, 0.077 g) as a single, unidentified olefin isomer. $^1$H NMR (400 MHz, Chloroform-d) δ 8.41 (s, 1H), 8.20 (s, 1H), 7.77 (dd, 1H), 7.75-7.69 (d, 2H), 7.60 (d, 1H), 7.35-7.26 (m, 4H), 7.18-7.06 (m, 8H), 6.93 (d, 1H), 6.29 (broad s, 1H), 5.59 (broad s, 1H). Mass (m/z): 446 (M+1)+.

D. (E)-3-(2-(4-(diphenylamino)phenyl)benzofuran-6-yl)acrylic acid (BC-153)

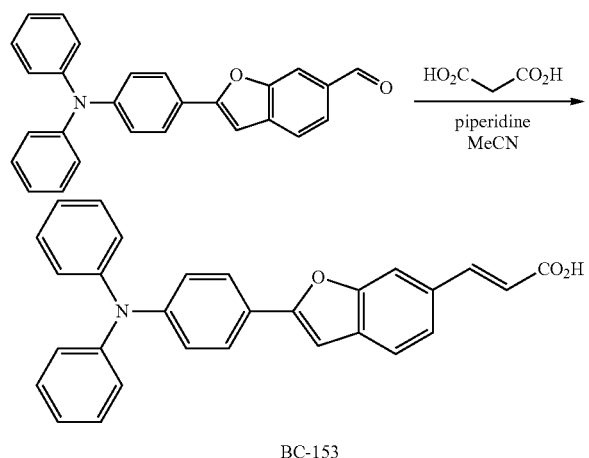

BC-153

To 2-(4-(diphenylamino)phenyl)benzofuran-6-carbaldehyde (0.15 g) and malonic acid (0.043 g) was added acetonitrile (1.9 mL) and piperidine (0.094 mL). The reaction was heated to reflux for 22 hours then cooled to room temperature. Water (10 mL) and dichloromethane (15 mL) were added and the aqueous layer acidified with 1M HCl. The layers were separated and the aqueous layer extracted with dichloromethane (2×15 mL). The combined organic fractions were dried over sodium sulfate, filtered and concentrated to afford (E)-3-(2-(4-(diphenylamino)phenyl)benzofuran-6-yl)acrylic acid (BC-153, 0.166 g). $^1$H NMR (400 MHz, DMSO-d6) δ 12.29 (broad s, 1H), 7.93 (s, 1H), 7.78 (d, 2H), 7.66 (d, 1H), 7.62-7.52 (m, 2H), 7.37-7.29 (m, 4H), 7.26 (d, 1H), 7.12-7.04 (m, 6H), 6.99 (d, 2H), 6.54 (d, J=16.0 Hz, 1H). Mass (m/z): 432 (M+1)+.

E. 2-((2-(4-(Diphenylamino)phenyl)benzofuran-6-yl)methylene)malononitrile (BC-154)

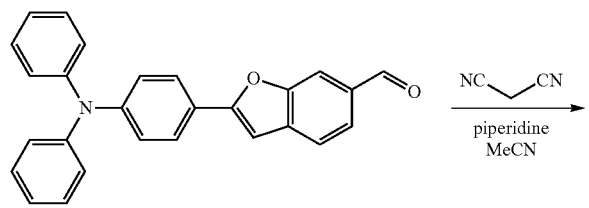

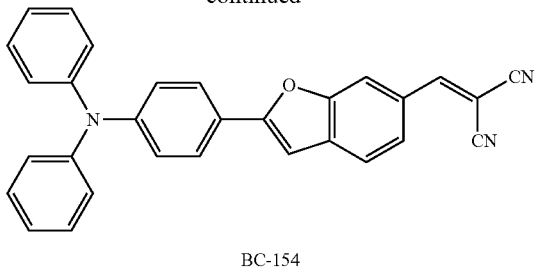

BC-154

To 2-(4-(diphenylamino)phenyl)benzofuran-6-carbaldehyde (0.16 g) and malononitrile (0.029 g) was added acetonitrile (2.0 mL) and piperidine (0.020 mL). The reaction was heated to reflux for 22 hours then cooled to room temperature. Water (10 mL) and dichloromethane (15 mL) were added and the aqueous layer acidified with 1M HCl. The layers were separated and the aqueous layer extracted with dichloromethane (2×15 mL). The combined organic fractions were dried over sodium sulfate, filtered and concentrated. The residue was purified via chromatography on silica gel (elution with 0 to 20% ethyl acetate in hexanes) to afford 2-((2-(4-(diphenylamino)phenyl)benzofuran-6-yl)methylene)malononitrile (BC-154, 0.051 g). $^1$H NMR (400 MHz, DMSO-d6) δ 8.53 (s, 1H), 8.17 (s, 1H), 7.88-7.77 (m, 4H), 7.39 (d, 2H), 7.35-7.31 (m, 3H), 7.17-7.07 (m, 6H), 6.97 (d, 2H). Mass (m/z): 438 (M+1)+.

F. 2-((2-(4-(Diphenylamino)phenyl)benzofuran-6-yl)methylene)malonamide (BC-155)

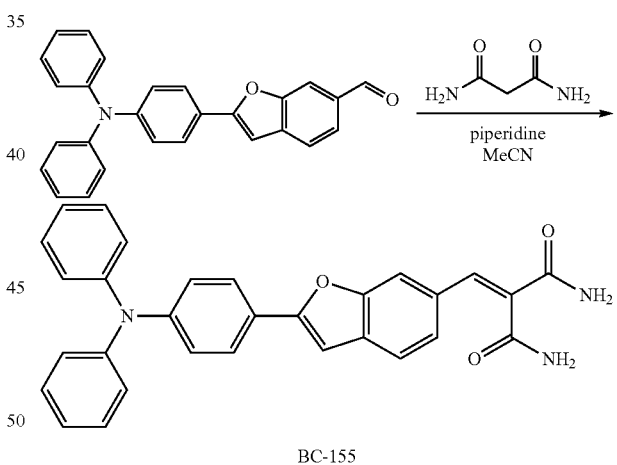

BC-155

To 2-(4-(diphenylamino)phenyl)benzofuran-6-carbaldehyde (0.16 g) and malonamide (0.046 g) was added acetonitrile (2.1 mL) and piperidine (0.020 mL). The reaction was heated to reflux for 24 hours, then additional malonamide (0.046 g), piperidine (0.02 mL) and 1,2-dichloroethane (1.0 mL) were added and the reaction heated at reflux for an additional 12 hours. A third portion of malonamide (0.046 g) and of piperidine (0.04 mL) was added and the reaction heated for an additional 24 hours. The reaction was cooled to room temperature and water (10 mL) and ethyl acetate (15 mL) were added. The reaction mixture was stirred at room temperature for 1 hour and then the precipitate collected by filtration. The precipitate was dried under vacuum at 60° C. to afford 2-((2-(4-(diphenylamino)phenyl)benzofuran-6-yl)

methylene)malonamide (BC-155, 0.64 g). ¹H NMR (400 MHz, DMSO-d6) δ 7.86 (s, 1H), 7.82-7.75 (m, 3H), 7.58 (d, 1H), 7.54 (s, 1H), 7.43-7.36 (m, 2H), 7.36-7.29 (m, 4H), 7.26 (broad s, 1H), 7.25 (d, 1H), 7.13 (broad s, 1H), 7.12-7.03 (m, 6H), 6.98 (d, 2H). Mass (m/z): 474 (M+1)+.

G. Dimethyl 2-((2-(4-(diphenylamino)phenyl)benzofuran-6-yl)methylene)malonate (BC-160)

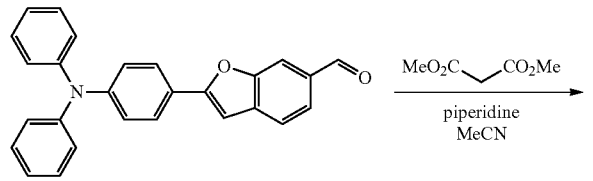

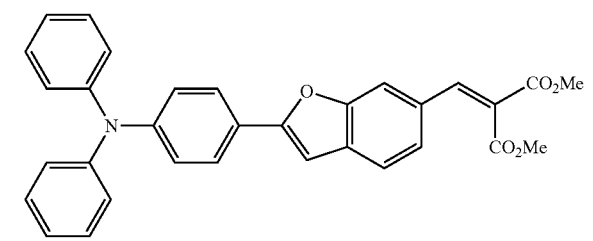

BC-160

To 2-(4-(diphenylamino)phenyl)benzofuran-6-carbaldehyde (0.15 g) and dimethyl malonate (0.10 g) was added acetonitrile (1.9 mL) and piperidine (0.038 mL). The reaction was heated to reflux for 21 hours then cooled to room temperature. Water (10 mL) and aqueous HCl (1M, 1.0 mL) were added and the reaction extracted with ethyl acetate (3×15 mL). The combined organic was washed with aqueous NaOH (1M, 6×10 mL) and washed with brine. The organic layer was dried over sodium sulfate, filtered, and concentrated to dimethyl 2-((2-(4-(diphenylamino)phenyl)benzofuran-6-yl)methylene)malonate (BC-160, 0.11 g). ¹H NMR (400 MHz, Chloroform-d) δ 7.86 (s, 1H), 7.70 (d, 2H), 7.58 (s, 1H), 7.52 (d, 1H), 7.34-7.26 (m, 5H), 7.18-7.03 (m, 8H), 6.88 (s, 1H), 3.90 (s, 3H), 3.86 (s, 3H). Mass (m/z): 504 (M+1)+.

H. Methyl 2-cyano-3-(2-(4-(diphenylamino)phenyl)benzofuran-6-yl)acrylate (BC-161)

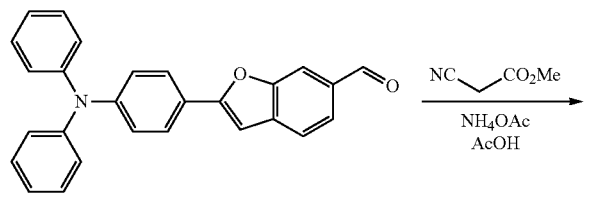

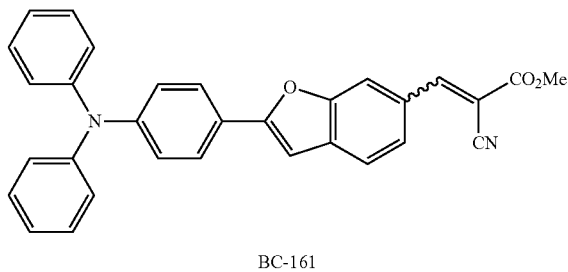

BC-161

Acetic acid (1.3 mL) was added to 2-(4-(diphenylamino)phenyl)benzofuran-6-carbaldehyde (0.10 g), methyl cyanoacetate (0.064 g), and ammonium acetate (0.062 g) and the reaction heated to reflux for 2 hours. The reaction was cooled to room temperature and water (10 mL) was added. The reaction was stirred at room temperature for one hour then the precipitate collected by filtration. The solid material was washed with water (50 mL) and hexanes (50 mL) and dried under vacuum at 50° C. to afford methyl 2-cyano-3-(2-(4-(diphenylamino)phenyl)benzofuran-6-yl)acrylate (BC-161, 0.12 g) as a single, unidentified olefin isomer. ¹H NMR (400 MHz, Chloroform-d) δ 8.34 (s, 1H), 8.30 (s, 1H), 7.78 (dd, 1H), 7.72 (d, 2H), 7.60 (d, 1H), 7.30 (dd, 5H), 7.18-7.06 (m, 7H), 6.93 (d, 1H), 3.94 (s, 3H). Mass (m/z): 471 (M+1)+.

I. 2-Cyano-3-(2-(4-(diphenylamino)phenyl)benzofuran-6-yl)-N-(pyridin-2-ylmethyl)acrylamide (BC-163)

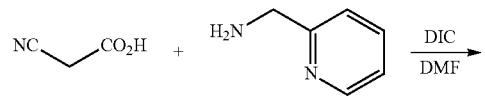

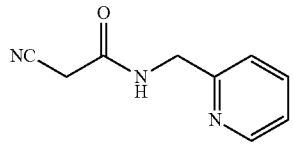

To a 0° C. solution of cyanoacetic acid (0.51 g) and 2-picaloylamine (0.62 mL) in anhydrous N,N-dimethylformamide (15.1 mL) was added N,N-diisopropylcarbodiimide (1.12 mL). The reaction was stirred at 0° C. for 10 minutes then this ice bath removed and the reaction stirred at room temperature for 65 hours. The precipitate was removed by filtration and the filtrate concentrated. The residue was purified via chromatography on silica gel (elution with 0 to 6% methanol in dichloromethane) to afford the intermediate 2-cyano-N-(pyridin-2-ylmethyl)acetamide (0.91 g). ¹H NMR (400 MHz, Chloroform-d) δ 8.56 (d, 1H), 7.69 (td, 2H), 7.51 (broad s, 1H), 7.28-7.18 (m, 2H), 4.59 (d, 3H), 3.45 (s, 3H).

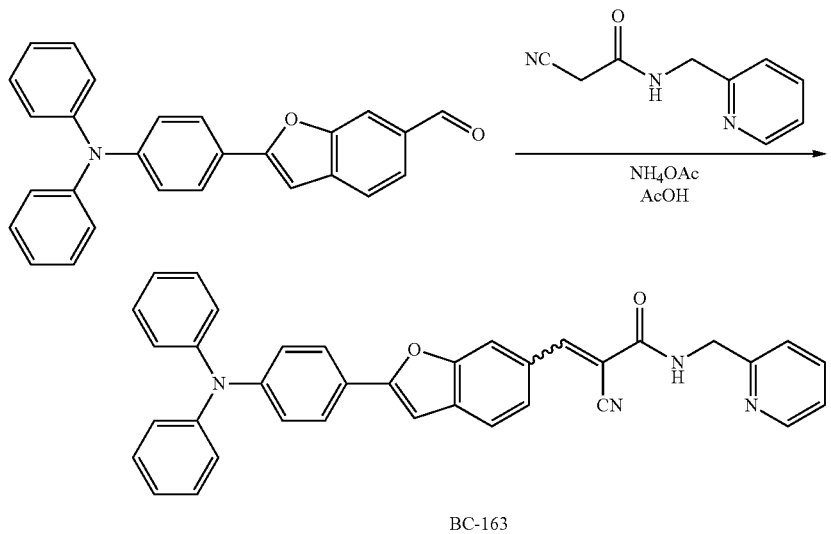

BC-163

Acetic acid (2.0 mL) was added to 2-(4-(diphenylamino) phenyl)benzofuran-6-carbaldehyde (0.15 g), 2-cyano-N-(pyridin-2-ylmethyl)acetamide (0.10 g), and ammonium acetate (0.091 g) and the reaction heated to reflux for 3 hours. The reaction was cooled to room temperature and water (15 mL) added. The reaction was stirred at room temperature for one hour then the precipitate collected by filtration. The solid material was washed with water (50 mL) and hexanes (50 mL) and dried under vacuum at 50° C. to afford 2-cyano-3-(2-(4-(diphenylamino)phenyl)benzofuran-6-yl)-N-(pyridin-2-ylmethyl)acrylamide (BC-163, 0.18 g) as a single, unidentified olefin isomer. $^1$H NMR (400 MHz, DMSO-d6) δ 8.97 (t, 1H), 8.50 (ddd, 1H), 8.33 (s, 1H), 8.24 (s, 1H), 7.91-7.79 (m, 3H), 7.78-7.69 (m, 2H), 7.41-7.29 (m, 6H), 7.26 (dd, 1H), 7.16-7.05 (m, 6H), 6.99 (d, 2H), 4.51 (d, 2H). Mass (m/z): 547 (M+1)+.

J. Methyl (E)-3-(2-(4-(diphenylamino)phenyl)benzofuran-6-yl)acrylate (BC-170)

Acetic acid (2.7 mL) was added to 2-(4-(diphenylamino) phenyl) benzofuran-6-carbaldehyde (0.21 g), methyl potassium malonate (0.20 g), and ammonium acetate (0.12 g) and the reaction heated to reflux for 6 hours. The reaction was cooled to room temperature and water (10 mL) added. The reaction was stirred at room temperature for 12 hours and the aqueous extracted with ethyl acetate (3×15 mL). The combined organic was washed with brine, dried over sodium sulfate, filtered and concentrated. The residue was purified via chromatography on silica gel (elution with 0 to 5% methanol in dichloromethane) to afford methyl (E)-3-(2-(4-(diphenylamino)phenyl)benzofuran-6-yl)acrylate (BC-170, 0.056 g). $^1$H NMR (400 MHz, Chloroform-d) δ 7.79 (d, 1H), 7.70 (d, 1H), 7.64 (s, 1H), 7.52 (d 1H), 7.40 (dd, 1H), 7.29 (dd, 4H), 7.18-7.04 (m, 9H), 6.88 (d, 1H), 6.46 (d, 1H), 3.82 (s, 3H). Mass (m/z): 446 (M+1)+.

Example 12

Syntheses of BC-167, -168 and -171

BC-167 (3-(2-(4-(tert-Butyl)phenyl)benzofuran-6-yl)-2-cyanoacrylic acid) was synthesized as shown in Synthetic Scheme I (where Z=R$^3$). 1-(R$^3$)-4-ethynylbenzene (where R$^3$ is tert-butyl) was condensed with 3-hydroxy-4-iodobenzaldehyde, followed by addition of R$^2$CH$_2$R$^1$ to the 2-(4-(tert-butyl)phenyl)benzofuran-6-carbaldehyde.

The intermediate 2-(4-(tert-butyl)phenyl)benzofuran-6-carbaldehyde was synthesized as follows:

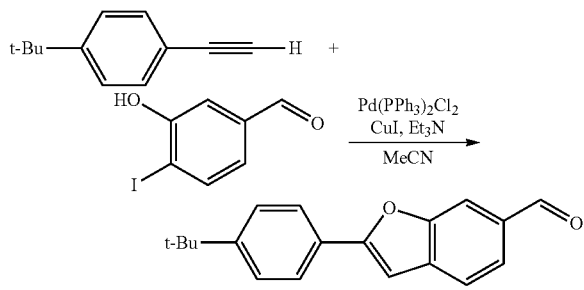

To a 25 mL flask was added 3-hydroxy-4-iodobenzaldehyde (0.25 g), bis(triphenylphosphine)palladium dichloride (0.021 g), and copper(I) iodide (0.017 g). The flask was purged with nitrogen for 20 minutes. A solution of triethylamine (0.70 mL) in anhydrous acetonitrile (5.0 mL) was degassed by bubbling nitrogen through it for 20 minutes. The triethylamine solution and 1-(tert-butyl)-4-ethynylbenzene (0.22 mL) were added to the reaction and this stirred at room temperature for 18 hours. Water (5 mL) and ethyl acetate (5 mL) were added and the reaction stirred at room temperature for 1 hour. Water (5 mL) and 1M HCl (1 mL) were added and then the aqueous extracted with ethyl acetate (3×15 mL). The combined organic layer was washed with brine, dried over magnesium sulfate, filtered, and concentrated. The residue was purified by chromatography on silica gel (elution with 0 to 10% ethyl acetate in hexanes) to afford 2-(4-(tert-butyl)phenyl)benzofuran-6-carbaldehyde (0.24 g). 1H NMR (400 MHz, Chloroform-d) δ 10.06 (s, 1H), 8.01 (s, 1H), 7.84 (d, 2H), 7.77 (dd, 1H), 7.68 (d, 1H), 7.51 (d, 2H), 7.05 (d, 1H), 1.36 (s, 9H).

BC-167 was then synthesized as follows:

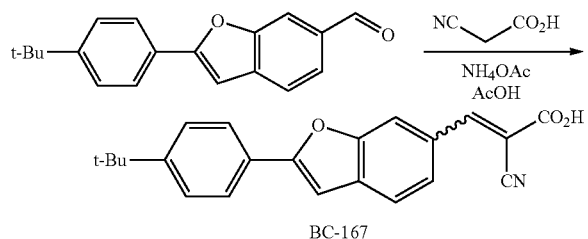

Acetic acid (4.31 mL) was added to 2-(4-(tert-butyl) phenyl)benzofuran-6-carbaldehyde (0.24 g), cyanoacetic acid (0.18 g), and ammonium acetate (0.20 g) and the reaction heated to reflux for 2 hours. The reaction was cooled to room temperature and water (10 mL) added. The reaction was stirred at room temperature for 17 hours and then the precipitate collected via filtration. The solid material was washed with water (50 mL) and hexanes (50 mL) and dried under vacuum at 50° C. to afford 3-(2-(4-(tert-butyl)phenyl)benzofuran-6-yl)-2-cyanoacrylic acid (BC-167, 0.28 g) as a single, unidentified olefin isomer. $^1$H NMR (400 MHz, DMSO-d6) δ 13.88 (broad s, 1H), 8.42 (s, 1H), 8.33 (s, 1H), 7.97 (dd, 1H), 7.90 (d, 2H), 7.80 (d, 1H), 7.57-7.48 (m, 3H), 1.29 (s, 9H). Mass (m/z): 346 (M+1)+.

BC-168 and -171 were also synthesized according to Synthetic Scheme I, Z is electron-donating group, X– at the 4-position of the resulting 2-(4-(X)phenyl)-benzofuran-6-carbaldehyde intermediate and final product.

2-Cyano-3-(2-(4-methoxyphenyl)benzofuran-6-yl)acrylic acid (BC-168) was made via the intermediate 2-(4-methoxyphenyl)benzofuran-6-carbaldehyde as follows:

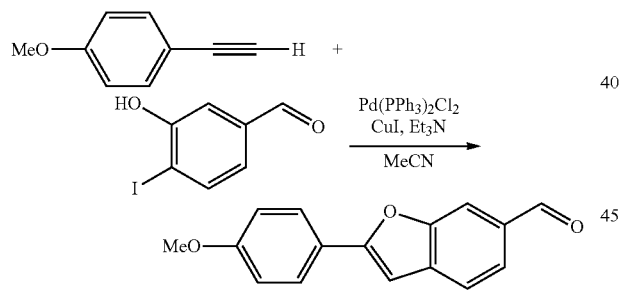

To a 25 mL flask was added 3-hydroxy-4-iodobenzaldehyde (0.25 g), bis(triphenylphosphine)palladium dichloride (0.021 g), and copper(I) iodide (0.017 g). The flask was purged with nitrogen for 20 minutes. A solution of triethylamine (0.70 mL) in anhydrous acetonitrile (5.0 mL) was degassed by bubbling nitrogen through for 20 minutes. The triethylamine solution and 1-ethynyl-4-methoxybenzene (0.16 mL) were then added to the reaction mixture. The reaction mixture was then stirred at room temperature for 18 hours. Water (5 mL) and ethyl acetate (5 mL) were added and the reaction stirred at room temperature for 1 hour. Water (5 mL) and 1M HCl (1 mL) were added and then the aqueous layer extracted with ethyl acetate (3×15 mL). The combined organic fractions were washed with brine, dried over magnesium sulfate, filtered, and the filtrate concentrated. The residue was purified via chromatography on silica gel (elution with 0 to 15% ethyl acetate in hexanes) to afford 2-(4-methoxyphenyl)benzofuran-6-carbaldehyde (0.25 g). 1H NMR (400 MHz, Chloroform-d) δ 10.05 (s, 1H), 7.99 (s, 1H), 7.84 (d, 2H), 7.76, (dd, 1H), 7.65 (d, 1H), 7.01 (d, 2H), 6.95 (d, 1H), 3.88 (s, 3H).

The final product BC-168 was derived from the intermediate as follows:

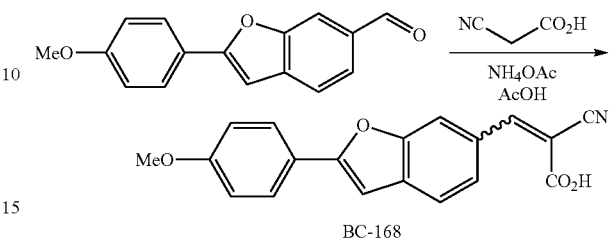

Acetic acid (4.87 mL) was added to 2-(4-methoxyphenyl) benzofuran-6-carbaldehyde (0.25 g), cyanoacetic acid (0.20 g), and ammonium acetate (0.23 g) and the reaction heated to reflux for 2 hours. The reaction was cooled to room temperature and water (10 mL) added. The reaction was stirred at room temperature for 17 hours and then the precipitate collected by filtration. The solid material was washed with water (50 mL) and hexanes (50 mL) and dried under vacuum at 50° C. to afford 2-cyano-3-(2-(4-methoxyphenyl)benzofuran-6-yl)acrylic acid (BC-168, 0.27 g) as a single, unidentified olefin isomer. $^1$H NMR (400 MHz, DMSO-d6) δ 13.85 (s, 1H), 8.41 (s, 1H), 8.31 (s, 1H), 7.98-7.88 (m, 3H), 7.77 (d, 1H), 7.42 (d, 1H), 7.07 (d, 2H), 3.81 (s, 3H). Mass (m/z): 320 (M+1)+.

2-Cyano-3-(2-(4-phenoxyphenyl)benzofuran-6-yl)acrylic acid (BC-171) was made via the intermediate 2-(4-phenoxyphenyl)benzofuran-6-carbaldehyde as follows:

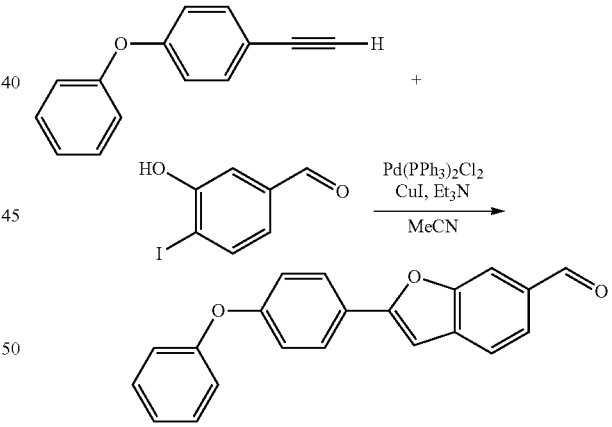

To a 25 mL flask was added 3-hydroxy-4-iodobenzaldehyde (0.25 g), bis(triphenylphosphine)palladium dichloride (0.021 g), and copper(I) iodide (0.017 g). The flask was purged with nitrogen for 20 minutes. A solution of triethylamine (0.70 mL) in anhydrous acetonitrile (5.0 mL) was degassed by bubbling nitrogen through for 20 minutes. The triethylamine solution and 1-ethynyl-4-phenoxybenzene (0.22 mL) were added to the reaction and this heated to 40° C. for 2.5 hours. The reaction was cooled to room temperature and water (5 mL) and 1M HCl (1 mL) added. The aqueous was extracted with ethyl acetate (3×15 mL) and the combined organic layer was washed with brine, dried over magnesium sulfate, filtered, and concentrated. The residue was purified via chromatography on silica gel (elution with 0 to 13% ethyl acetate in hexanes) to afford 2-(4-phenoxyphenyl)benzofuran-6-carbaldehyde (0.25 g). $^1$H NMR (400 MHz, Chloroform-d) δ 10.06 (s, 1H), 8.00 (s, 1H), 7.86 (d, 2H), 7.78 (dd, 1H), 7.67 (d, 1H), 7.39 (dd, 2H), 7.18 (d, 1H), 7.12-7.05 (m, 4H), 7.00 (d, 1H).

The final product BC-171 was derived from the intermediate as follows:

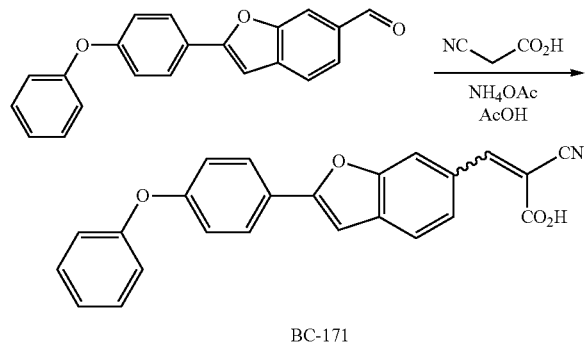

BC-171

Acetic acid (3.98 mL) was added to 2-(4-phenoxyphenyl)benzofuran-6-carbaldehyde (0.25 g), cyanoacetic acid (0.16 g), and ammonium acetate (0.18 g) and the reaction heated to reflux for 2 hours. The reaction was cooled to room temperature and water (10 mL) added. The reaction was stirred at room temperature for 1 hour and then the precipitate collected via filtration. The solid material was washed with water (50 mL) and hexanes (50 mL) and dried under vacuum at 50° C. to afford 2-cyano-3-(2-(4-phenoxyphenyl)benzofuran-6-yl)acrylic acid (BC-171, 0.28 g) as a single, unidentified olefin isomer. $^1$H NMR (400 MHz, DMSO-d6) δ 13.87 (s, 1H), 8.42 (s, 1H), 8.32 (s, 1H), 8.06-7.90 (m, 3H), 7.80 (d), 7.49 (d, 1H), 7.47-7.36 (m, 2H), 7.19 (t, 1H), 7.13-7.04 (m, 4H). Mass (m/z): 382 (M+1)+.

Example 13

Synthetic Scheme II—Synthesis of BC-151

Synthetic Scheme II

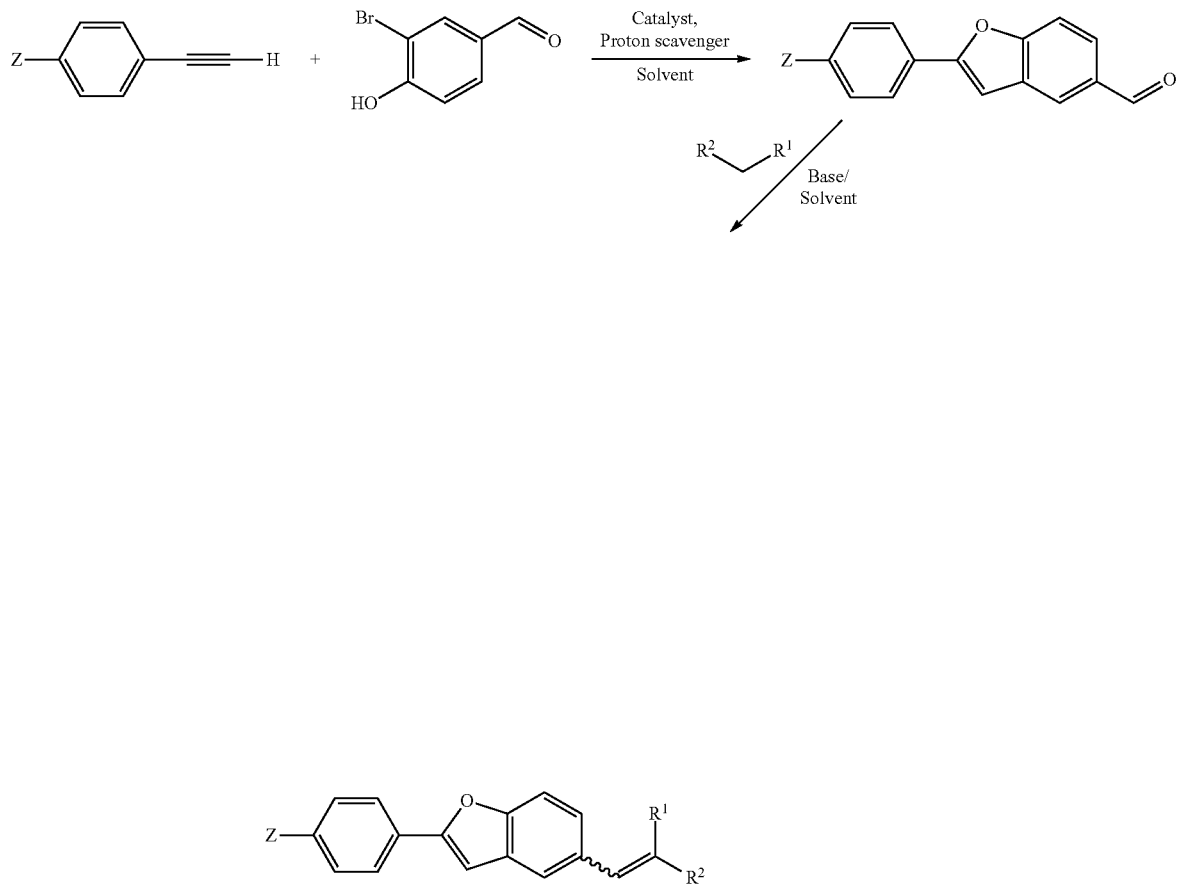

2-Cyano-3-(2-(4-(diphenylamino)phenyl)benzofuran-5-yl)acrylic acid (BC-151) was synthesized according to Synthetic Scheme II, starting with condensation of 4-(Z)ethynylbenzene (where Z=diphenylamine) with 3-bromo-4-hydroxybenzaldehyde to form the 2-(4-(Z)phenyl) benzofuran-5-carbaldehyde, followed by addition of R²CH₂R¹ to the carbaldehyde.

BC-151 was made via the intermediate 2-(4-(diphenylamino)phenyl)-benzofuran-5-carbaldehyde as follows:

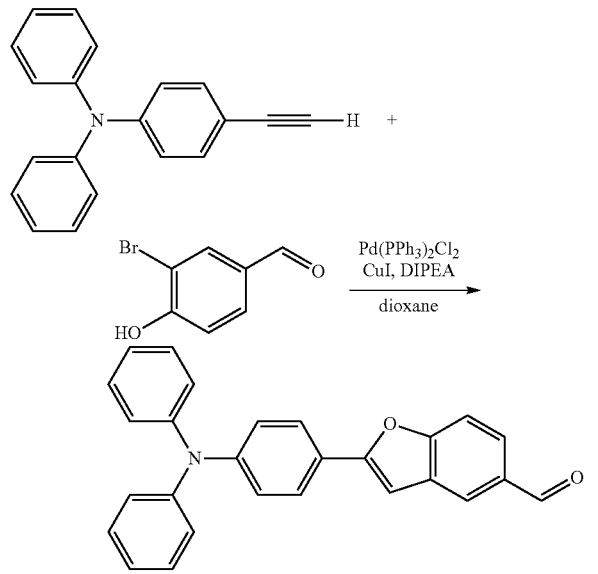

To a nitrogen filled flask was added 4-ethynyl-N,N-diphenylaniline (0.49 g), 3-bromo-4-hydroxybenzaldehyde (0.30 g), bis(triphenylphosphine)palladium dichloride (0.032 g), and copper(I) iodide (0.026 g) and the flask was purged with nitrogen for 20 minutes. Degassed 1,4-dioxane (7.5 mL) and N,N-diisopropylethylamine (1.3 mL) were added to the reaction and the reaction heated to 80° C. for 2 hours. The reaction temperature was increased to 100° C. for 22 hours. The reaction mixture was cooled to room temperature and water (10 mL) and brine (10 mL) were added. The aqueous layer was extracted with ethyl acetate (3×30 mL) and the combined organic layers dried over magnesium sulfate, filtered, and concentrated. The residue was purified via chromatography on silica gel (elution with 0 to 10% ethyl acetate in hexanes) to afford 2-(4-(diphenylamino)phenyl)benzofuran-5-carbaldehyde (0.24 g). ¹H NMR (400 MHz, Chloroform-d) δ 10.04 (s, 1H), 7.98 (s, 1H), 7.78-7.71 (m, 3H), 7.64 (d, 2H), 7.33-7.27 (m, 4H), 7.18-7.06 (m, 7H), 6.94 (d, 1H).

The final product BC-151 was derived from the intermediate as follows:

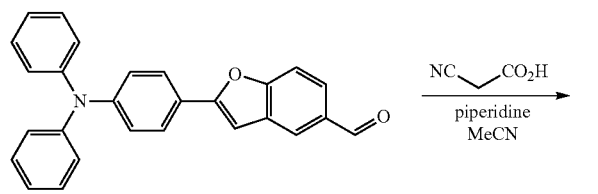

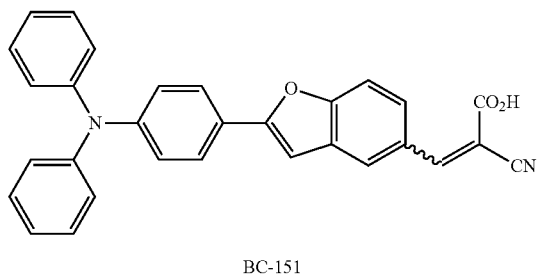

BC-151

To 2-(4-(diphenylamino)phenyl)benzofuran-5-carbaldehyde (0.24 g) was added acetonitrile (3.0 mL), cyanoacetic acid (0.057 g), and piperidine (0.090 mL). The reaction was heated to reflux for 3 hours then cooled to room temperature. Water (10 mL) and dichloromethane (20 mL) were added and the aqueous acidified to pH=2 with 1M HCl. The layers were separated and the aqueous extracted with dichloromethane (2×20 mL). The combined organic was washed with brine, dried over sodium sulfate, filtered, and concentrated. The residue was purified via chromatography on silica gel (elution with 0 to 15% methanol in dichloromethane) to provide 2-cyano-3-(2-(4-(diphenylamino)phenyl) benzofuran-5-yl)acrylic acid (BC-151, 0.14 g) as a single, unidentified olefin isomer. ¹H NMR (400 MHz, DMSO-d6) δ 13.96 (broad s, 1H), 8.38 (s, 1H), 8.31 (s, 1H), 7.95 (d, 1H), 7.78 (t, 3H), 7.39 (s, 1H), 7.33 (t, 4H), 7.09 (dd, 6H), 6.99 (d, 2H). Mass (m/z): 457 (M+1)+.

Example 14

Synthetic Scheme III—Syntheses of BC-156, -157, -158, -159 and -175

Synthetic Scheme III

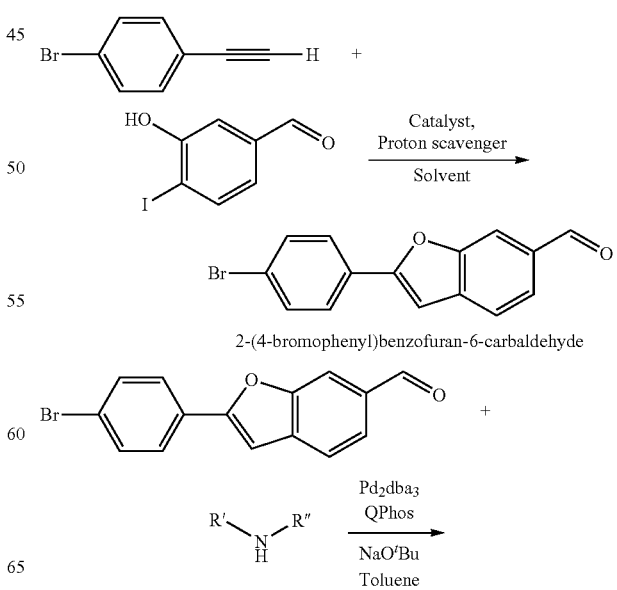

2-(4-bromophenyl)benzofuran-6-carbaldehyde

-continued

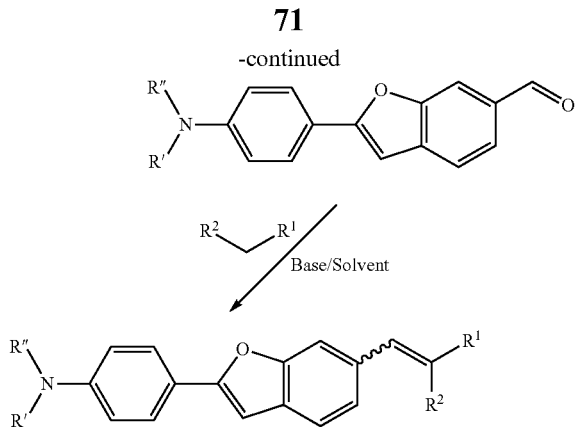

Products BC-156, -157, -158, -159 and -175, were all synthesized according to Synthetic Scheme III. First, 1-bromo-4-ethynylbenzene was condensed with 3-hydroxy-4-iodobenzaldehyde in the presence of a catalyst (bis(triphenylphosphine)-palladium dichloride/copper(I) iodide in acetonitrile) and proton scavenger (triethylamine) to form intermediate 2-(4-bromophenyl)benzofuran-6-carbaldehyde. The intermediate was then condensed with R'(R")'N to form 2-(4-(R'(R")amino)phenyl)-benzofuran-6-carbaldehyde which was followed by addition of $R^2CH_2R^1$ to form each of the BC products.

A. Synthesis of intermediate 2-(4-bromophenyl)benzofuran-6-carbaldehyde

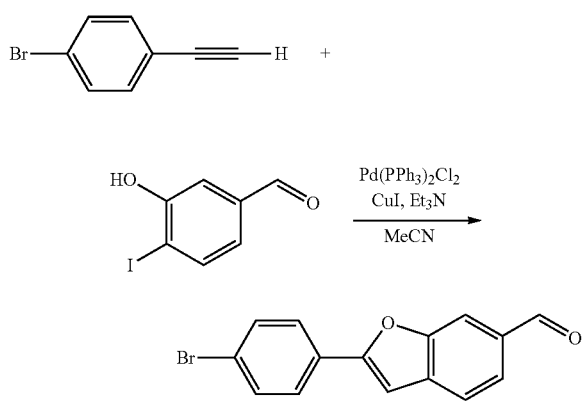

To a 100 mL flask was added 1-bromo-4-ethynylbenzene (1.75 g), 3-hydroxy-4-iodobenzaldehyde (2.00 g), bis(triphenylphosphine)palladium dichloride (0.17 g), and copper(I) iodide (0.14 g). The flask was purged with nitrogen for 20 minutes. A solution of triethylamine (5.62 mL) in anhydrous acetonitrile (40.3 mL) was degassed by bubbling nitrogen through for 20 minutes. The degassed triethylamine solution was added to the reaction and the reaction heated to 40° C. for 1.5 hours. The reaction was cooled to room temperature and concentrated. The residue was purified via chromatography on silica gel (elution with 0 to 25% ethyl acetate in hexanes) to afford 2-(4-bromophenyl)benzofuran-6-carbaldehyde (2.50 g). $^1$H NMR (400 MHz, Chloroform-d) δ 10.07 (s, 1H), 8.01 (s, 1H), 7.86-7.74 (m, 3H), 7.70 (d, 1H), 7.66-7.56 (m, 2H), 7.10 (d, 1H).

B. Synthesis of intermediate, 2-(4-(bis(4-methoxyphenyl)amino)phenyl)-benzofuran-6-carbaldehyde

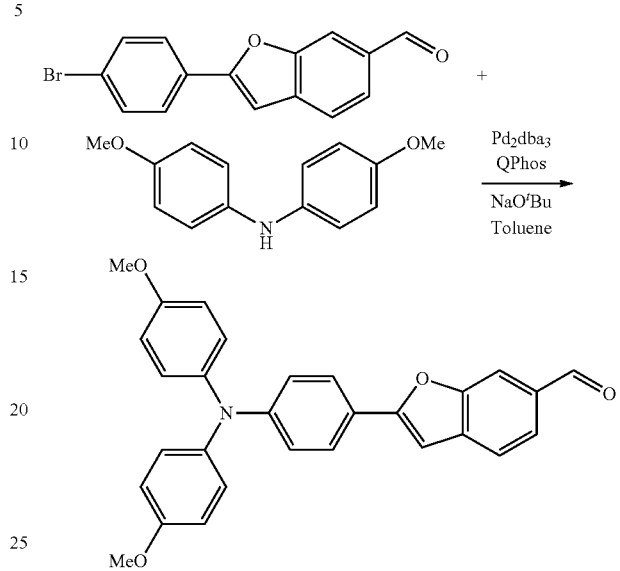

A 10 mL flask containing 2-(4-bromophenyl)benzofuran-6-carbaldehyde (0.053 g), bis(4-methoxyphenyl)amine (0.041 g), tris(dibenzylideneacetone)dipalladium (0.0041 g), QPhos (0.0063 g), and sodium tert-butoxide (0.026 g) was purged with nitrogen for 20 minutes. Anhydrous toluene (0.89 mL) was degassed by bubbling nitrogen through for 20 minutes then added to the reaction. The reaction was stirred at room temperature for 2.5 hours and quenched by the addition of water (10 mL). The aqueous was extracted with ethyl acetate (3×15 mL) and the combined organic dried over magnesium sulfate. The organic layer was filtered and concentrated. The residue was purified via chromatography on silica gel (elution with 0 to 20% ethyl acetate in hexanes) to afford 2-(4-(bis(4-methoxyphenyl)amino)phenyl)benzofuran-6-carbaldehyde (0.046 g). $^1$H NMR (400 MHz, Chloroform-d) δ 10.03 (s, 1H), 7.96 (s, 1H), 7.74 (dd, 1H), 7.66 (d, 2H), 7.61 (d, 1H), 7.10 (dd, 4H), 6.95 (dd, 2H), 6.89-6.83 (m, 5H), 3.81 (s, 6H).

C. Synthesis of 3-(2-(4-(Bis(4-methoxyphenyl)amino)phenyl)benzofuran-6-yl)-2-cyanoacrylic acid (BC-156) and 3-(2-(4-(Bis(4-methoxyphenyl)amino)phenyl)-benzofuran-6-yl)acrylonitrile (BC-157)

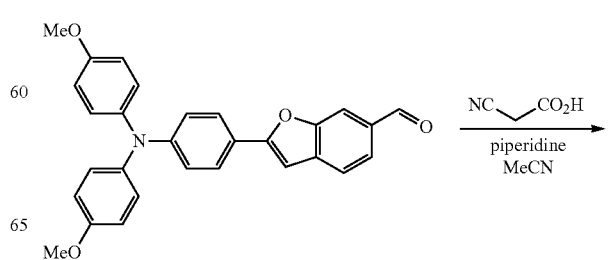

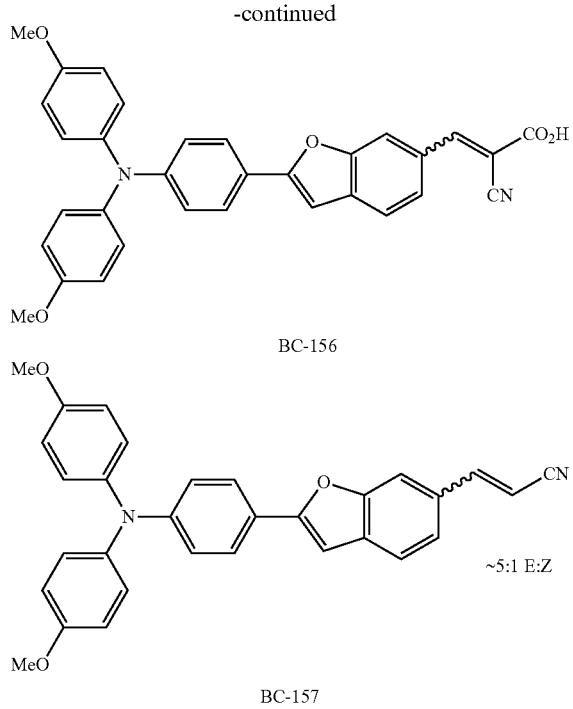

BC-156

BC-157

~5:1 E:Z

To a solution of 2-(4-(bis(4-methoxyphenyl)amino)phenyl)benzofuran-6-carbaldehyde (0.20 g) and cyanoacetic acid (0.042 g) in acetonitrile (2.27 mL) was added piperidine (0.067 mL). The reaction was heated to reflux for 24 hours. Additional cyanoacetic acid (0.042 g) and piperidine (0.067 mL) were added and the reaction heated at reflux for an additional 4 hours. The reaction was cooled to room temperature and water (10 mL) and dichloromethane (20 mL) were added. The aqueous layer was acidified to pH=2 with 1M HCl and the layers separated. The aqueous fraction was extracted with dichloromethane (2×15 mL) and the combined organic fractions dried over sodium sulfate, filtered and concentrated. The residue was purified via column chromatography (0 to 15% methanol in dichloromethane) to afford impure BC-156 and impure BC-157. BC-156 was further purified via column chromatography on silica gel ($1^{st}$ column: elution with 0 to 10% methanol in dichloromethane; $2^{nd}$ column: elution with 0 to 100% ethyl acetate in hexanes, then 0 to 20% methanol in dichloromethane) to afford 3-(2-(4-(bis(4-methoxyphenyl)amino)phenyl)benzofuran-6-yl)-2-cyanoacrylic acid (BC-156, 0.037 g) as a single, unidentified olefin isomer. The impure BC-157 was further purified via column chromatography on silica gel (elution with 0 to 20% ethyl acetate in hexanes) to afford 3-(2-(4-(bis(4-methoxyphenyl)amino)phenyl)benzofuran-6-yl)acrylonitrile (BC-157, 0.064 g) as an approximately 5:1 mixture of E:Z olefin isomers.

BC-156: $^1$H NMR (400 MHz, DMSO-d6) δ 8.11 (s, 1H), 8.01 (broad s, 1H), 7.72 (d, 3H), 7.63 (d, 1H), 7.21 (s, 1H), 7.08 (dd, 4H), 6.92 (dd, 4H), 6.76 (dd, 2H), 3.72 (s, 6H). Mass (m/z): 517 (M+1)+. BC-157, major isomer (E isomer): $^1$H NMR (400 MHz, Chloroform-d) δ 7.69-7.56 (m, 2H), 7.54 (s, 1H), 7.50 (d, 1H), 7.47 (d, 1H), 7.29 (dd, 1H), 7.14-7.05 (m, 4H), 6.94 (dd, 2H), 6.90-6.79 (m, 5H), 5.85 (d, J=16.6 Hz, 1H), 3.81 (s, 6H). Mass (m/z): 473 (M+1)+.

D. Synthesis of intermediate 2-(4-(bis(4-(tert-butyl)phenyl)amino)phenyl)-benzofuran-6-carbaldehyde

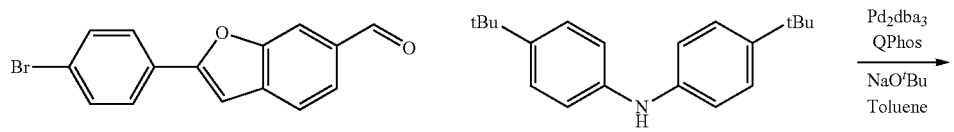

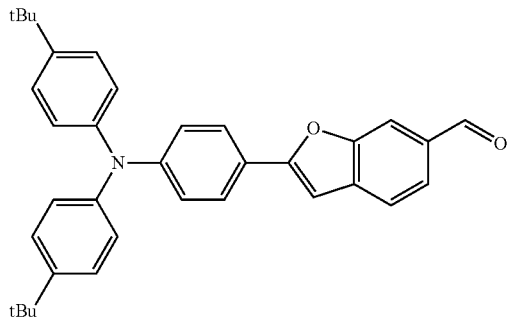

A 10 mL flask containing 2-(4-bromophenyl)benzofuran-6-carbaldehyde (0.21 g), bis(4-(tert-butyl)phenyl)amine (0.19 g), tris(dibenzylideneacetone)dipalladium (0.016 g), QPhos (0.024 g), and sodium tert-butoxide (0.099 g) was purged with nitrogen for 20 minutes. Anhydrous toluene (3.43 mL) was degassed by bubbling nitrogen through for 20 minutes then added to the reaction. The reaction was stirred at room temperature for 3 hours and quenched by the addition of water (15 mL) and 1M HCl (1.02 mL). The aqueous was extracted with ethyl acetate (3×20 mL) and the combined organic fractions dried over magnesium sulfate, filtered and concentrated. The residue was purified via chromatography on silica gel (elution with 0 to 10% ethyl acetate in hexanes) to afford 2-(4-(bis(4-(tert-butyl)phenyl)amino)phenyl)benzofuran-6-carbaldehyde (0.20 g). $^1$H NMR (400 MHz, Chloroform-d) δ 10.03 (s, 1H), 7.97 (s, 1H), 7.75 (dd, 1H), 7.70 (d, 2H), 7.62 (d, 1H), 7.30 (d, 4H), 7.07 (dd, Hz, 6H), 6.91 (d, 1H), 1.32 (s, 18H).

E. Synthesis of 3-(2-(4-(Bis(4-(tert-butyl)phenyl)amino)phenyl)benzofuran-6-yl)-2-cyanoacrylic acid (BC-158)

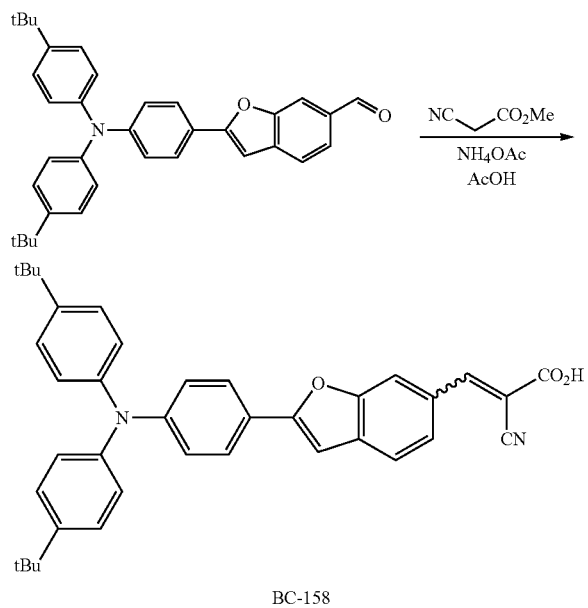

BC-158

Acetic acid (0.49 mL) was added to 2-(4-(bis(4-(tert-butyl)phenyl)amino)phenyl)benzofuran-6-carbaldehyde (0.049 g), cyanoacetic acid (0.020 g), and ammonium acetate (0.023 g) and the reaction heated to reflux for 1.5 hours. The reaction was cooled to room temperature and water (10 mL) added. The reaction was stirred at room temperature for 2 hours then the precipitate collected by filtration. The solid material was washed with water (50 mL) and hexanes (50 mL) and dried under vacuum at 50° C. to afford 3-(2-(4-(bis(4-(tert-butyl)phenyl)amino)phenyl)benzofuran-6-yl)-2-cyanoacrylic acid (BC-158, 0.049 g) as a single, unidentified olefin isomer. $^1$H NMR (400 MHz, DMSO-d6) δ 8.38 (s, 1H), 8.28 (s, 1H), 7.93 (d, 1H), 7.80 (d, 2H), 7.74 (d, 1H), 7.40-7.29 (m, 5H), 7.02 (d, 4H), 6.90 (d, 2H), 1.25 (s, 18H). Mass (m/z): 569 (M+1)+.

F. Synthesis of 2-Cyano-3-(2-(4-(di(pyridin-3-yl)amino)phenyl)benzofuran-6-yl)acrylic acid (BC-159)

The intermediate di(pyridin-3-yl)amine:

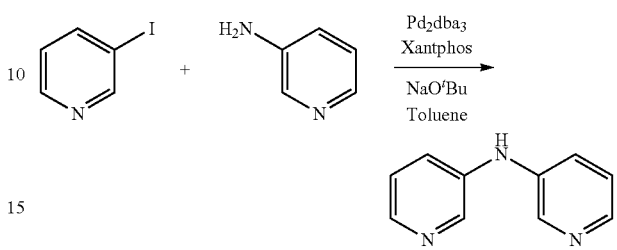

was synthesized by a procedure adapted from WO2007089735A2. A 25 mL flask containing 3-aminopyridine (0.30 g), 3-iodopyridine (0.99 g), tris(dibenzylideneacetone)dipalladium (0.0291 g), Xantphos (0.084 g), and sodium tert-butoxide (0.37 g) was purged with nitrogen for 20 minutes. Anhydrous toluene (6.41 mL) was degassed by bubbling nitrogen through for 20 minutes and then added to the reaction. The reaction was heated to 50° C. for 24 hours and then cooled to room temperature. The reaction mixture was diluted with dichloromethane (100 mL) and then washed with water (20 mL) and brine (20 mL). The organic layer was dried over sodium sulfate, filtered, and concentrated. The residue was purified via chromatography on silica gel (elution with 0 to 10% methanol in dichloromethane) to afford di(pyridin-3-yl)amine (0.54 g). $^1$H NMR (400 MHz, Chloroform-d) δ 8.41 (d, J=2.8 Hz, 2H), 8.23 (dd, J=4.7, 1.3 Hz, 2H), 7.41 (ddd, J=8.2, 2.5, 1.2 Hz, 2H), 7.21 (dd, J=8.3, 4.8 Hz, 2H), 5.81 (broad s, 1H).

Next the intermediate 2-(4-(di(pyridin-3-yl)amino)phenyl)benzofuran-6-carbaldehyde was synthesized as follows:

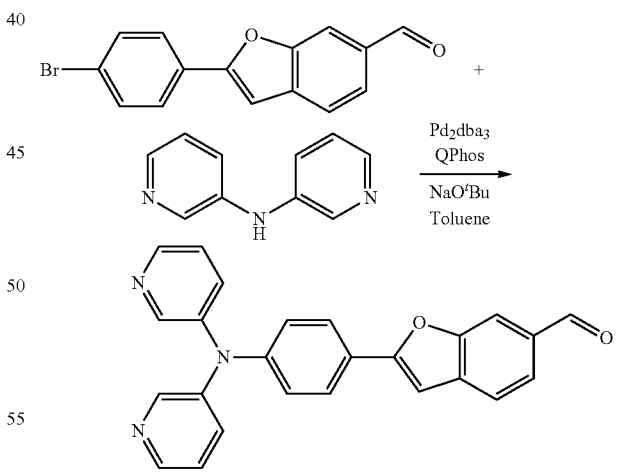

A 10 mL flask containing 2-(4-bromophenyl)benzofuran-6-carbaldehyde (0.19 g), di(pyridin-3-yl)amine (0.11 g), tris(dibenzylideneacetone)dipalladium (0.014 g), QPhos (0.022 g), and sodium tert-butoxide (0.089 g) was purged with nitrogen for 30 minutes. Anhydrous toluene (3.1 mL) was degassed by bubbling nitrogen through for 30 minutes then added to the reaction. The reaction was stirred at room temperature for 3 hours and quenched by the addition of water (15 mL). The aqueous was extracted with dichloromethane (3×15 mL) and the combined organic fractions dried over magnesium sulfate, filtered and concentrated. The residue was purified via chromatography on silica gel (elution with 0 to 5% methanol in dichloromethane) to afford 2-(4-(di(pyridin-3-yl)amino)phenyl)benzofuran-6-carbaldehyde (0.096 g). $^1$H NMR (400 MHz, Chloroform-d) δ 10.05 (s, 1H), 8.45 (d, 2H), 8.36 (dd, 2H), 8.00 (s, 1H), 7.84-7.79 (m, 2H), 7.77 (dd, 1H), 7.67 (d, 1H), 7.46 (ddd, 2H), 7.25 (m, 2H), 7.15 (d, 2H), 7.01 (d, 1H).

The final product 2-cyano-3-(2-(4-(di(pyridin-3-yl)amino)phenyl)-benzofuran-6-yl)acrylic acid (BC-159) was synthesized:

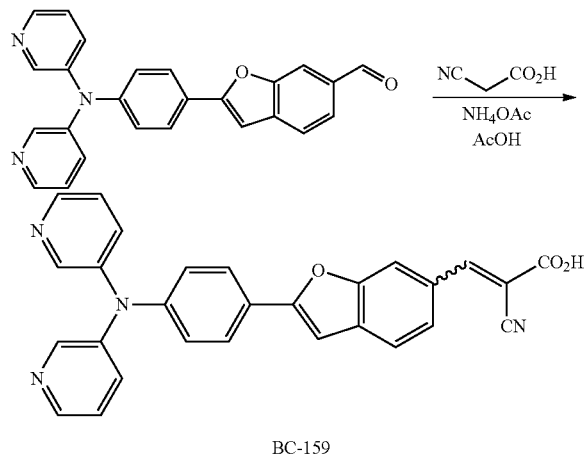

BC-159

Acetic acid (1.04 mL) was added to 2-(4-(di(pyridin-3-yl)amino)phenyl)benzofuran-6-carbaldehyde (0.096 g), cyanoacetic acid (0.043 g), and ammonium acetate (0.048 g) and the reaction heated to reflux for 2.5 hours. The reaction was cooled to room temperature and water (10 mL) added. The reaction was stirred at room temperature for 0.5 hours then the precipitate collected via filtration. The solid material was washed with water (50 mL) and hexanes (50 mL) and dried under vacuum at 50° C. The material was purified via chromatography on silica gel (elution with 0 to 20% methanol in dichloromethane) to afford 2-cyano-3-(2-(4-(di (pyridin-3-yl)amino)phenyl)benzofuran-6-yl)acrylic acid (BC-159, 0.066 g) as a single, unidentified olefin isomer. $^1$H NMR (400 MHz, DMSO-d6) δ 8.35 (d, 2H), 8.33 (dd, 2H), 8.21 (s, 1H), 8.17 (broad s, 1H), 7.91 (d, 2H), 7.84 (d, 1H), 7.73 (d, 1H), 7.55 (ddd, 2H), 7.42 (s, 1H), 7.38 (dd, 2H), 7.09 (d, 2H). Mass (m/z): 459 (M+1)+.

G. Synthesis of 2-cyano-3-(2-(4-(methyl(phenyl)amino)phenyl)benzofuran-6-yl)acrylic acid (BC-175)

First, the intermediate 2-(4-(methyl(phenyl)amino)phenyl)benzofuran-6-carbaldehyde was made as follows:

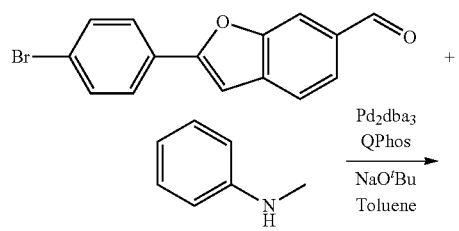

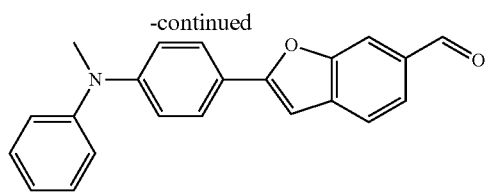

A 10 mL flask containing 2-(4-bromophenyl)benzofuran-6-carbaldehyde (0.19 g), tris(dibenzylideneacetone)dipalladium (0.014 g), QPhos (0.022 g), and sodium tert-butoxide (0.089 g) was purged with nitrogen for 30 minutes. Anhydrous toluene (3.1 mL) was degassed by bubbling nitrogen through for 30 minutes. The degassed toluene and N-methylaniline (0.07 mL) were added to the flask. The reaction mixture was stirred at room temperature for 1 hour and quenched by the addition of water (10 mL) and 1M HCl (1 mL). The aqueous layer was extracted with ethyl acetate (3×15 mL) and the combined organic fractions washed with brine and dried over magnesium sulfate, filtered and concentrated. The residue was purified via chromatography on silica gel (elution with 0 to 15% ethyl acetate in hexanes) to afford 2-(4-(methyl(phenyl)amino)phenyl) benzofuran-6-carbaldehyde (0.12 g). $^1$H NMR (400 MHz, Chloroform-d) δ 10.03 (s, 1H), 7.97 (s, 1H), 7.77-7.71 (m, 3H), 7.62 (d, 1H), 7.38 (dd, 2H), 7.20 (dd, 2H), 7.18-7.12 (m, 1H), 6.94 (d, 2H), 6.89 (d, 1H), 3.39 (s, 3H).

The final product BC-175 was made from the intermediate as follows:

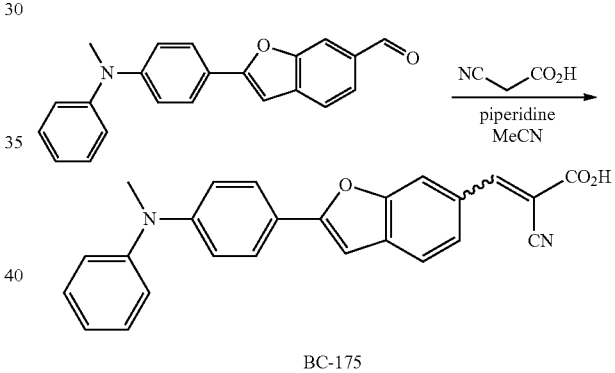

BC-175

Acetonitrile (1.92 mL) and piperidine (0.076 mL) were added to 2-(4-(methyl(phenyl)amino)phenyl)benzofuran-6-carbaldehyde (0.12 g) and cyanoacetic acid (0.049 g). The reaction heated to reflux for 2 hours. The reaction was cooled to room temperature and water (10 mL) and acetic acid (1 mL) were added. The reaction was stirred at room temperature for 4 hours then the precipitate collected by filtration. The solid material was washed with water (50 mL) and hexanes (50 mL) and dried under vacuum at 50° C. to afford 2-cyano-3-(2-(4-(methyl(phenyl)amino)phenyl)benzofuran-6-yl)acrylic acid (BC-175, 0.135 g) as a single, unidentified olefin isomer. $^1$H NMR (400 MHz, DMSO-d6) δ 13.9 (broad s, 1H), 8.37 (s, 1H), 8.27 (s, 1H), 7.92 (d, 1H), 7.84-7.76 (m, 2H), 7.72 (d, 1H), 7.42-7.35 (m, 2H), 7.30 (d, 1H), 7.21 (dd, 2H), 7.15 (t, 1H), 6.96-6.88 (d, 2H), 3.32 (s, 3H). Mass (m/z): 395 (M+1)+.

Example 15

Synthesis of BC-166, -169, -172 and -173

Final products BC-166, -169, -172 and -173, were synthesized from 2-(4-bromophenyl)benzofuran-6-carbaldehyde (synthesized in Example 14A above). For these molecules, the carbaldehyde was protected as the acetal prior to its reaction with a secondary amine, as shown in Synthetic Scheme IV, in which addition of a cyclic secondary amine to the acetal is shown (for illustrative purposes). The condensation with amine is followed by deprotection of the carbaldehyde and its reaction with R²CH₂R¹ (as in Synthetic Scheme I).

Synthetic Scheme IV

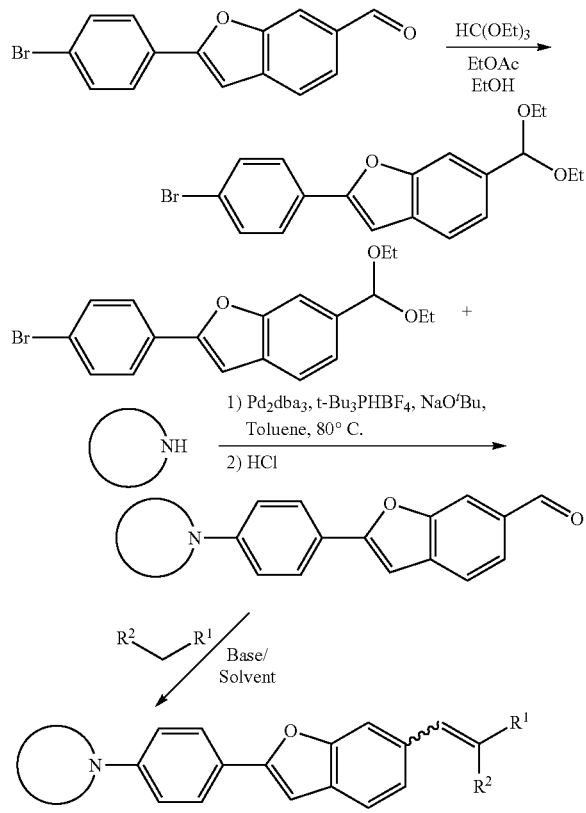

A. Synthesis of common intermediate 2-(4-Bromophenyl)-6-(diethoxymethyl)-benzofuran

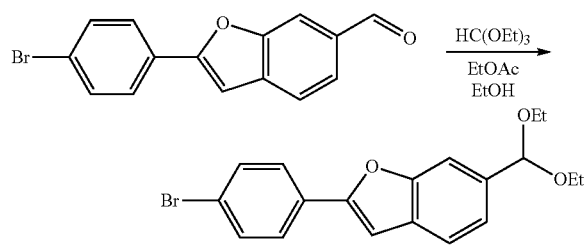

To a nitrogen flushed flask containing 2-(4-bromophenyl)benzofuran-6-carbaldehyde (1.0 g) was added p-toluenesulfonic acid monohydrate (0.063 g), ethanol (200 proof, 8.3 mL), ethyl acetate (8.3 mL) and triethylorthoformate (5.5 mL). The reaction was stirred at room temperature for 22 hours. Toluene (15 mL) was added and the reaction concentrated. Toluene (15 mL) was again added and the reaction again concentrated to afford 2-(4-bromophenyl)-6-(diethoxymethyl)benzofuran which was used without further purification. ¹H NMR (400 MHz, DMSO-d6) δ 7.84 (d, 2H), 7.68 (d, 2H), 7.62 (d, 1H), 7.58 (s, 1H), 7.48 (d, 1H), 7.29 (dd, 1H), 5.57 (s, 1H), 3.57-3.42 (m, 4H), 1.13 (t, 6H).

B. Synthesis of 2-Cyano-3-(2-(4-(piperidin-1-yl)phenyl)benzofuran-6-yl)acrylic acid (BC-166)

First, the intermediate 2-(4-(Piperidin-1-yl)phenyl)benzofuran-6-carbaldehyde was made as follows:

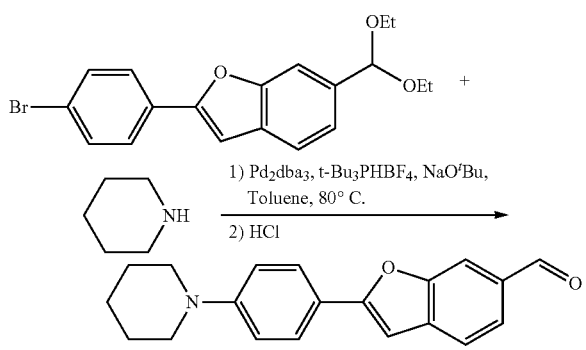

A 10 mL flask containing the 2-(4-bromophenyl)-6-(diethoxymethyl)benzofuran (0.075 g), tris(dibenzylideneacetone)dipalladium (0.005 g), tri-tert-butylphosphonium tetrafluoroborate (0.003 g), and sodium tert-butoxide (0.029 g) was purged with nitrogen for 20 minutes. Anhydrous toluene (0.40 mL) was degassed by bubbling nitrogen through for 20 minutes then added to the reaction. Piperidine (0.024 mL) was added and the reaction heated to 80° C. for 2 hours and then cooled to room temperature. Ethyl acetate (10 mL) and 1M HCl (10 mL) were added and the reaction stirred at room temperature for 1.5 hours. The aqueous layer was neutralized with saturated sodium bicarbonate and extracted with ethyl acetate (3×15 mL). The combined organic fractions were washed with brine, dried over magnesium sulfate, filtered and the filtrate concentrated. The residue was purified via chromatography on silica gel (elution with 0 to 10% ethyl acetate in hexanes) to afford 2-(4-(piperidin-1-yl)phenyl)benzofuran-6-carbaldehyde (0.044 g). ¹H NMR (400 MHz, Chloroform-d) δ 10.03 (s, 1H), 7.96 (s, 1H), 7.81-7.71 (m, 3H), 7.61 (d, J=7.9 Hz, 1H), 6.97 (d, J=7.9 Hz, 2H), 6.88 (s, 1H), 3.36-3.24 (m, 4H), 1.68 (d, J=29.2 Hz, 6H).

The final product BC-166 was then made as follows:

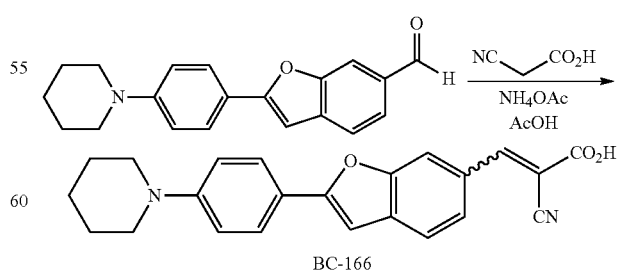

BC-166

Acetic acid (1.51 mL) was added to 2-(4-(piperidin-1-yl)phenyl)benzofuran-6-carbaldehyde (0.092 g), cyanoacetic acid (0.062 g), and ammonium acetate (0.070 g) and the reaction heated to reflux for 2.5 hours. The reaction was cooled to room temperature and water (20 mL) added. The reaction was stirred at room temperature for 1.5 hours then the precipitate collected by filtration. The solid material was washed with water (50 mL) and then with hexanes (50 mL) and then dried under vacuum at 50° C. to afford 2-cyano-3-(2-(4-(piperidin-1-yl)phenyl)benzofuran-6-yl)acrylic acid (BC-166, 0.090 g) as a single, unidentified olefin isomer. $^1$H NMR (400 MHz, DMSO-d6) δ 8.35 (s, 1H), 8.25 (s, 1H), 7.91 (dd, 1H), 7.77 (d, 2H), 7.70 (d, 1H), 7.27 (d, 1H), 7.01 (d, 2H), 3.30 (broad s, 4H), 1.56 (broad s, 6H). Mass (m/z): 373 (M+1)+.

C. Synthesis of 2-Cyano-3-(2-(4-morpholinophenyl) benzofuran-6-yl)acrylic acid (BC-169

First the intermediate 2-(4-Morpholinophenyl)benzofuran-6-carbaldehyde was made as follows:

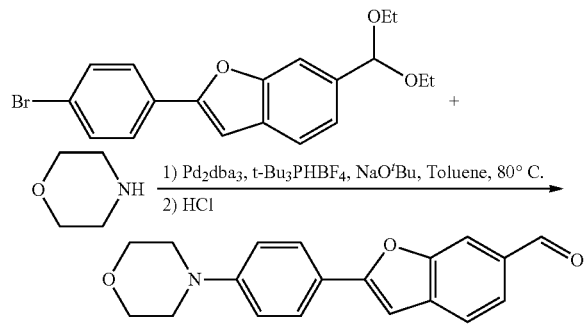

To 2-(4-bromophenyl)-6-(diethoxymethyl)benzofuran (0.309 g, 0.824 mmol) was added tris(dibenzylideneacetone)dipalladium(0) (19 mg), tri(tert-butyl)phosphine tetrafluoroborate (12 mg) and sodium tert-butoxide (118 mg). The reaction mixture was purged with nitrogen for 20 minutes. Dry toluene (3 mL) was degassed by purging with nitrogen for 20 minutes and then added to the reaction mixture. Morpholine (0.086 mL) was added and the reaction mixture was heated to 80° C. After 4 h, the reaction was cooled to room temperature, and 1 M HCl (10 mL) and ethyl acetate (10 mL) was added. The mixture was stirred at room temperature for 1.5 h. The reaction mixture was then neutralized with saturated sodium bicarbonate, extracted with ethyl acetate (3×15 mL), dried over sodium sulfate, filtered and concentrated. The solid was purified by silica gel column, eluting with hexanes:ethyl acetate (ethyl acetate as a gradient from 0 to 50%) to afford 2-(4-morpholinophenyl)-benzofuran-6-carbaldehyde (135 mg, 53%). $^1$H-NMR (400 MHz, CDCl3): δ 10.03 (s, 1H), 7.96 (s, 1H), 7.80 (d, 2H), 7.74 (dd, 1H), 7.62 (d, 1H), 6.99 (d, 2H), 6.91 (d, 1H), 3.88 (t, 4H), 3.26 (t, 4H). Mass (m/z): 308 (M+1)+.

The final product BC-169 was then made by reaction of 2-(4-morpholinophenyl)benzofuran-6-carbaldehyde with cyanoacetic acid in acetic acid in the presence of ammonium acetate (similarly to the methods described for synthesis of BC-166 from its corresponding aldehyde in Example 15B):

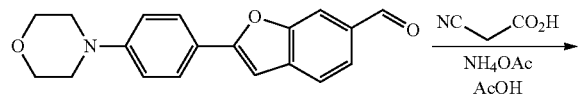

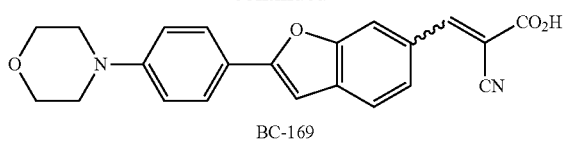

The yield was 143 mg. $^1$H NMR (400 MHz, DMSO-d6): δ 8.40 (s, 1H), 8.28 (s, 1H), 7.95 (dd, 1H), 7.82 (d, 2H), 7.73 (d, 1H), 7.33 (s, 1H), 7.05 (d, 2H), 3.73 (t, 4H), 3.22 (t, 4H). Mass (m/z): 375 (M+1)+.

D. Synthesis of 2-Cyano-3-(2-(4-(4-methylpiperazin-1-yl)phenyl)benzofuran-6-yl)acrylic acid (BC-172)

First, intermediate 2-(4-(4-Methylpiperazin-1-yl)phenyl)benzofuran-6-carbaldehyde was made

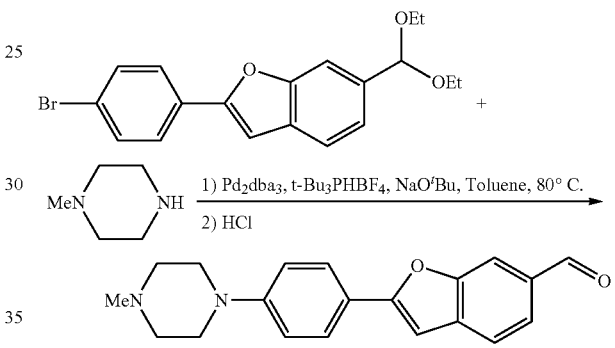

similarly to the methods described for synthesis of 2-(4-morpholinophenyl)benzofuran-6-carbaldehyde in Example 15C. The yield was 153 mg (58%). $^1$H NMR (400 MHz, DMSO-d6): δ 8.27 (s, 1H), 8.23 (s, 1H), 7.88 (dd, 1H), 7.83 (d, 2H), 7.71 (d, 1H), 7.32 (s, 1H), 7.09 (d, 2H), 3.42 (br s, 4H), 2.88 (br s, 4H), 2.49 (s, 3H). Mass (m/z): 388 (M+1)+.

The final product BC-172 was made

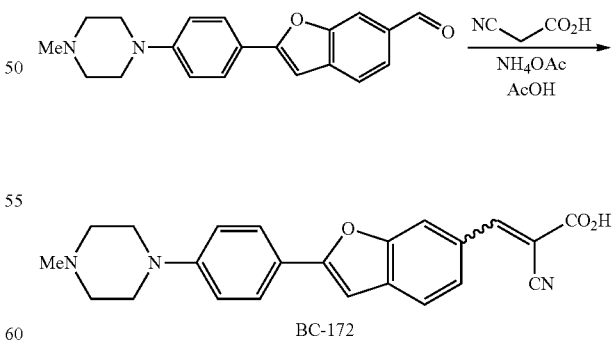

similar to the methods described for synthesis of BC-166 Example 15B, yield 64 mg, 70%. $^1$H-NMR (400 MHz, CDCl3): δ 10.02 (s, 1H), 7.95 (s, 1H), 7.78 (d, 2H), 7.73 (dd, 1H), 7.61 (d, 1H), 6.98 (d, 2H), 6.89 (d, 1H), 3.35 (t, 4H), 2.64 (t, 4H), 2.40 (s, 3H). Mass (m/z): 321 (M+1)+.

E. Synthesis of 2-Cyano-3-(2-(4-(diethylamino) phenyl)benzofuran-6-yl)acrylic acid (BC-173)

First, intermediate 2-(4-(Diethylamino)phenyl)benzofuran-6-carbaldehyde was made as follows:

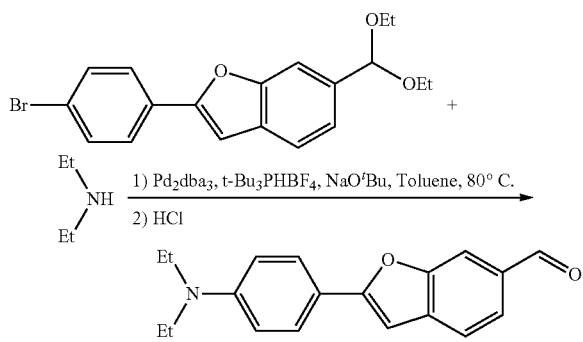

A 10 mL flask containing the 2-(4-bromophenyl)-6-(diethoxymethyl)benzofuran (0.22 g), tris(dibenzylideneacetone)dipalladium (0.013 g), tri-tert-butylphosphonium tetrafluoroborate (0.008 g), and sodium tert-butoxide (0.083 g) was purged with nitrogen for 20 minutes. Anhydrous toluene (1.2 mL) was degassed by bubbling nitrogen through for 20 minutes then added to the reaction. Diethylamine (0.12 mL) was added and the reaction heated to 80° C. for 2 hours and then cooled to room temperature. Ethyl acetate (5 mL) and 1M HCl (5 mL) were added and the reaction stirred at room temperature for 1 hour. The aqueous layer was neutralized with saturated sodium bicarbonate and extracted with ethyl acetate (3×15 mL). The combined organic fractions were washed with brine, dried over magnesium sulfate, filtered and concentrated. The residue was purified via chromatography on silica gel (elution with 0 to 10% ethyl acetate in hexanes) to afford 2-(4-(diethylamino)phenyl)-benzofuran-6-carbaldehyde (0.097 g). $^1$H NMR (400 MHz, DMSO-d6) δ 9.98 (s, 1H), 8.02 (s, 1H), 7.78-7.70 (m, 3H), 7.68 (d, 1H), 7.19 (d, 1H), 6.75 (d, 2H), 3.39 (q, 4H), 1.10 (t, 6H).

The final product BC-173 was then made as follows:

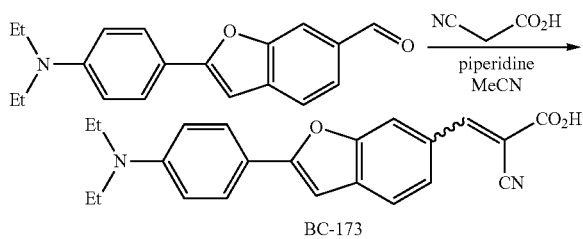

To 2-(4-(diethylamino)phenyl)benzofuran-6-carbaldehyde (0.097 g) and cyanoacetic acid (0.031 g) was added acetonitrile (1.6 mL) and piperidine (0.049 mL). The reaction was heated to reflux for 2 hours then additional cyanoacetic acid (0.006 g) was added. After an additional 2 hours, additional cyanoacetic acid (0.006 mg) and piperidine (0.024 mL) were added and the reaction heated at reflux for 20 hours. The reaction was cooled to room temperature, then water (10 mL) and acetic acid (1.0 mL) were added and the reaction stirred at room temperature for 2 hours. The precipitate was collected by filtration and washed with water (50 mL) and hexanes (50 mL). The solid was dried under vacuum at 50° C. to afford 2-cyano-3-(2-(4-(diethylamino) phenyl)-benzofuran-6-yl)acrylic acid (BC-173, 0.098 g) as a single, unidentified olefin isomer. $^1$H NMR (400 MHz, DMSO-d6) δ 13.76 (s, 1H), 8.38 (s, 1H), 8.25 (s, 1H), 7.91 (dd, 1H), 7.74 (d, 2H), 7.68 (d, 1H), 7.19 (d, 1H), 6.75 (d, 2H), 3.39 (q, 4H), 1.10 (t, 6H). Mass (m/z): 361 (M+1)+.

Example 16

Synthesis of BC-162 and BC-165

BC-162 and BC-165 were also synthesized from 2-(4-bromophenyl)benzofuran-6-carbaldehyde (synthesized in Example 14A above).

A. Synthesis of 3-(2-(4-bromophenyl)benzofuran-6-yl)-2-cyanoacrylic acid (BC-162)

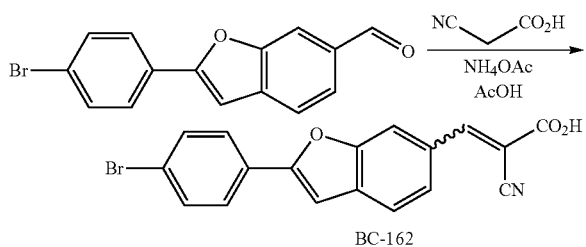

2-(4-Bromophenyl)benzofuran-6-carbaldehyde was converted to 3-(2-(4-bromophenyl)benzofuran-6-yl)-2-cyanoacrylic acid (BC-162) by reaction with cyanoacetic acid and ammonium acetate, similarly to the methods used for the synthesis of BC-166 in Example 15B, with a yield of 232 mg, 98%. $^1$H NMR (400 MHz, DMSO-d6): δ 8.27 (s, 1H), 8.26 (s, 1H), 7.94 (d, J=8.8 Hz, 2H), 7.90 (d, J=1.5 Hz, 1H), 7.80 (d, J=8.32 Hz, 1H), 7.73 (d, J=8.8 Hz, 2H), 7.62 (s, 1H), 7.22 (br s, 1H). Mass (m/z): 367 (M−1)−.

B. Synthesis of 2-Cyano-3-(2-(3',4'-dimethoxy-[1,1'-biphenyl]-4-yl)benzofuran-6-yl)acrylic acid (BC-165)

First, the intermediate 2-(3',4'-Dimethoxy-[1,1'-biphenyl]-4-yl)benzofuran-6-carbaldehyde was made as follows:

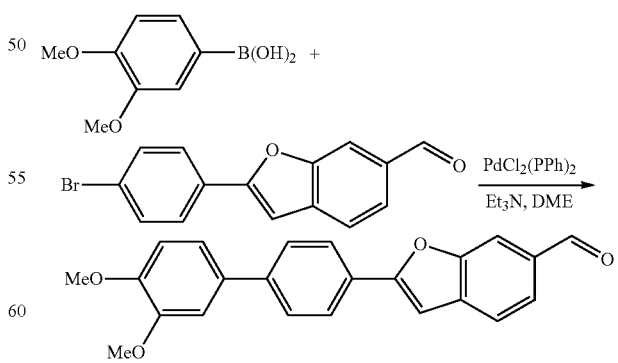

A round bottom flask (10 mL) was charged with 2-(4-bromophenyl)benzofuran-6-carbaldehyde (155 mg, 0.5 mmol), 3,4-dimethoxy phenyl boronic acid (100 mg, 0.5 mmol), and PdCl$_2$(PPh$_3$)$_2$ (17 mg), and then purged with nitrogen for 20 minutes. 1,2-Dimethoxyethane was degassed by bubbling nitrogen for 20 minutes. 1,2-Dimethoxyethane (3.5 mL) was added to the reaction, followed by the addition of triethylamine (101 mg) and stirred at 90° C. under nitrogen overnight. The reaction mixture was cooled to room temperature and the solvent was removed under vacuum. The solid was purified by silica gel column (hexanes with ethyl acetate from 0 to 30%) to afford 2-(3',4'-dimethoxy-[1,1'-biphenyl]-4-yl)benzofuran-6-carbaldehyde (88 mg, 49%) as light yellow solid. $^1$H-NMR (400 MHz, CDCl3): δ 10.06 (s, 1H), 8.02 (s, 1H), 7.94 (d, 2H), 7.78 (dd, 1H), 7.68 (m, 3H), 7.20 (m, 1H), 7.94 (d, 1H), 7.10 (s, 1H), 6.96 (d, 1H), 3.96 (s, 3H), 3.93 (s, 3H). Mass (m/z): 359 (M+1)+.

The final product BC-165 was then made as follows:

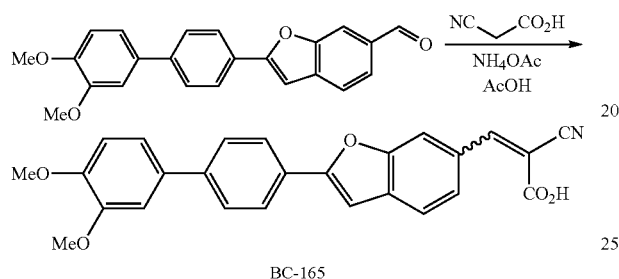

BC-165

To 2-(3',4'-dimethoxy-[1,1'-biphenyl]-4-yl)benzofuran-6-carbaldehyde (210.9 mg, 0.59 mmol) was added cyanoacetic acid (120 mg) and ammonium acetate (135 mg). Acetic acid (5 mL) was added and the reaction mixture was heated to reflux for 3 h, cooled to room temperature, added water (10 mL) and stirred 5 hr at room temperature. The solid was collected by filtration, and then the solid washed with water (40 mL) and then with hexanes (40 mL). The solid was then dried under high vacuum at 60° C. overnight to afford 2-cyano-3-(2-(3',4'-dimethoxy-[1,1'-biphenyl]-4-yl)benzofuran-6-yl)acrylic acid (BC-165, 0.165 g, 66%). $^1$H NMR (400 MHz, DMSO-d6): δ 8.44 (s, 1H), 8.36 (s, 1H), 8.04 (d, 2H), 8.00 (d, 1H), 7.84 (d, 3H), 7.63 (s, 1H), 7.39 (d, 2H), 7.06 (d, 1H), 3.87 (s, 3H), 3.80 (s, 3H). Mass (m/z): 424 (M−−1).

Example 17

Synthesis of BC-176

2-(4-(diphenylamino)phenyl)benzofuran-6-carboxylic acid (BC-176) was Synthesized According to Synthetic Scheme V Synthetic Scheme V

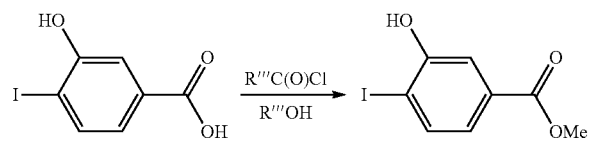

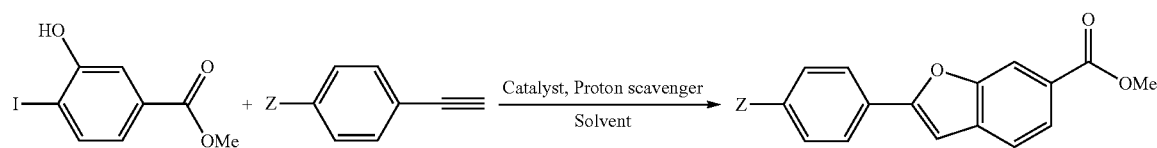

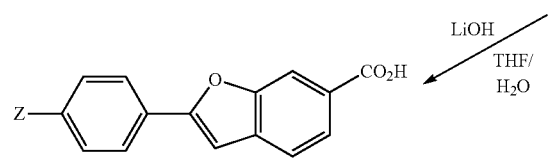

First, the intermediate methyl 2-hydroxy-3-iodobenzoate was made:

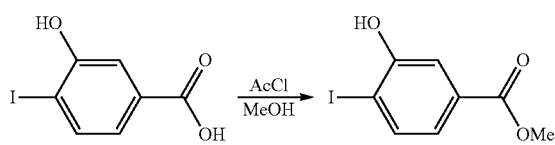 [SMILES: "MeOH" ; "AcCl" ; O=C(O)c1ccc(I)c(O)c1 ; COC(=O)c1ccc(I)c(O)c1]

A flask was fitted with a reflux condenser, flushed with nitrogen and charged with anhydrous methanol (7.9 mL) and acetyl chloride (0.03 mL). After 10 minutes 2-hydroxy-3-iodobenzoic acid (1.05 g) was added. The reaction was heated to reflux for 5.5 hours then cooled to room temperature. The methanol was removed under vacuum and the residue then redissolved in ethyl acetate (50 mL). The ethyl acetate solution was washed with saturated sodium bicarbonate (10 mL) and brine (10 mL), dried over magnesium sulfate, filtered and concentrated to afford methyl 2-hydroxy-3-iodobenzoate (1.1 g). $^1$H NMR (400 MHz, Chloroform-d) δ 7.74 (d, 1H), 7.61 (d, 1H), 7.33 (dd, 1H), 5.45 (s, 1H), 3.90 (s, 3H).

The next intermediate, methyl 2-(4-(diphenylamino)phenyl)benzofuran-6-carboxylate was made as follows:

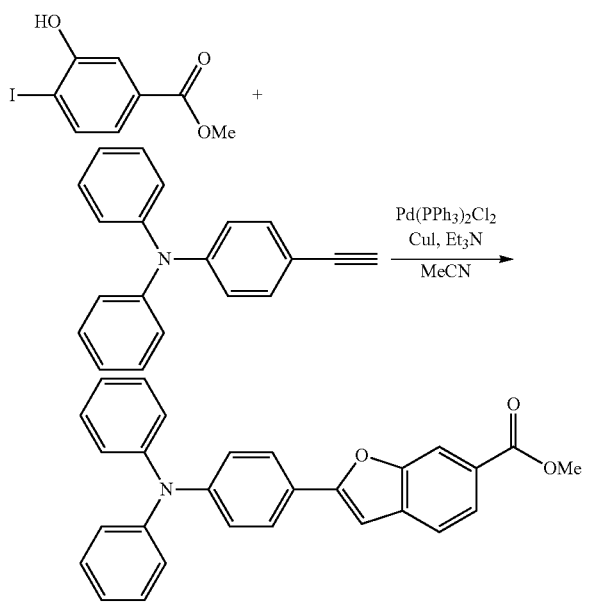

To a 100 mL flask was added methyl 2-hydroxy-3-iodobenzoate (1.1 g), 4-ethynyltriphenylamine (1.28 g), bis(triphenylphosphine)palladium dichloride (0.083 g), and copper(I) iodide (0.068 g). The flask was purged with nitrogen for 20 minutes. A solution of triethylamine (2.76 mL) in anhydrous acetonitrile (19.8 mL) was degassed by bubbling nitrogen through for 20 minutes. The triethylamine solution was added to the reaction flask and the reaction heated to 40° C. for 2.5 hours. The mixture was cooled to room temperature and water (15 mL) and brine (15 mL) added. The mixture was stirred at room temperature for 1 hour. The layers were then separated and the aqueous layer extracted with ethyl acetate (3×25 mL). The combined organic fractions were washed with 1M HCl and brine, dried over magnesium sulfate, filtered and concentrated. The residue was purified via chromatography on silica gel (elution with 0 to 8% ethyl acetate in hexanes) to afford methyl 2-(4-(diphenylamino)phenyl)benzofuran-6-carboxylate (1.5 g). $^1$H NMR (400 MHz, Chloroform-d) δ 8.17 (s, 1H), 7.93 (dd, 1H), 7.72 (d, 2H), 7.56 (d, 1H), 7.29 (dd, 5H), 7.19-7.05 (m, 7H), 6.91 (d, 1H), 3.94 (s, 3H).

Final product BC-176 was then made as follows:

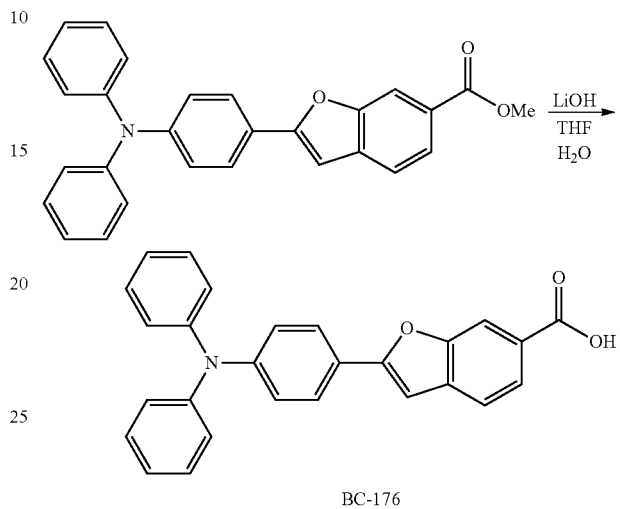

BC-176

To a solution of methyl 2-(4-(diphenylamino)phenyl)benzofuran-6-carboxylate (0.51 g) in THF (6.0 mL) was added 1M LiOH solution (1.2 mL). The reaction was stirred at room temperature for 40 min then heated to 40° C. for 2.5 hours. The reaction was heated to reflux for 19 hours then 1M LiOH (4.8 mL) was added. After an additional 4.5 hours the reaction was cooled to room temperature and water (10 mL) added. The aqueous was acidified to pH=4 with acetic acid, then extracted with ethyl acetate (3×20 mL). The combined organic fractions were dried over sodium sulfate, filtered, and concentrated to afford 2-(4-(diphenylamino)phenyl)benzofuran-6-carboxylic acid (BC-176, 0.49 g). $^1$H NMR (400 MHz, DMSO-d6) δ 12.88, (broad s, 1H), 8.04 (s, 1H), 7.85-7.77 (m, 3H), 7.66 (d, 1H), 7.39-7.29 (m, 5H), 7.15-7.04 (m, 6H), 7.04-6.96 (m, 2H). Mass (m/z): 406 (M+1)+.

Example 18

Synthesis of 2-(4-(diphenylamino)phenyl)-N-hydroxybenzofuran-6-carboxamide (BC-177)

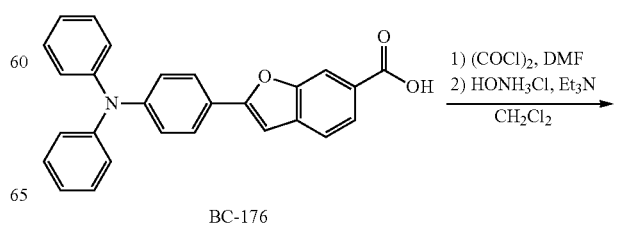

BC-176

-continued

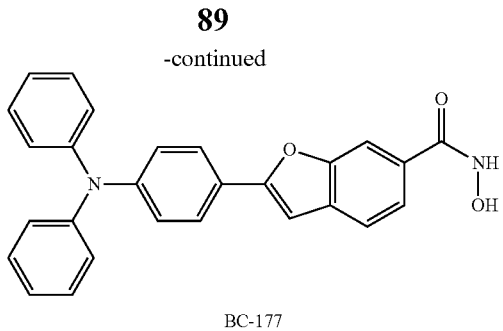

BC-177

A suspension of 2-(4-(diphenylamino)phenyl)benzofuran-6-carboxylic acid (BC-176, 0.13 g) in anhydrous dichloromethane (3.1 mL) was cooled to 0° C. and oxalyl chloride (0.053 mL) added. N,N-dimethylformamide (0.001 mL) was added and the reaction stirred at 0° C. for 10 min. The ice bath was removed and the reaction stirred at room temperature for 3 hours. The reaction was concentrated and anhydrous toluene (3 mL) was added and then removed in vacuo. Toluene (3 mL) was again added and removed in vacuo. The residue was dissolved in anhydrous dichloromethane (3.1 mL) and cooled to 0° C. Triethylamine (0.22 mL) and hydroxylamine hydrochloride (0.044 g) were added and the reaction was allowed to warm to room temperature slowly overnight. Water (10 mL) and saturated sodium bicarbonate (5 mL) were added and the aqueous extracted with dichloromethane (3×15 mL). The combined organic was washed with 1M HCl (10 mL), dried over sodium sulfate, filtered and concentrated. The residue was purified via chromatography on silica gel (elution with 0 to 5% methanol in dichloromethane) to afford 2-(4-(diphenylamino)phenyl)-N-hydroxybenzofuran-6-carboxamide (BC-177, 0.11 g). 1H NMR (400 MHz, DMSO-d6) δ 11.20 (broad s, 1H), 9.05 (broad s, 1H), 7.94 (d, 1H), 7.82 (d, 2H), 7.70-7.64 (m, 2H), 7.40-7.30 (m, 5H), 7.14-7.07 (m, 6H), 7.03 (d, 2H). Mass (m/z): 421 (M+H).

Example 19

Solar Cells Made Using Solar Cell Dyes—Set 1

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of $TiO_2$ (AEROXIDE® $TiO_2$ P 25, particle size of 21±5 nm, Evonik Industries, Essen, DE) and 5% by weight of poly (4-vinyl pyridine) was prepared and blade coated (6-8 microns thick) on the FTO coated side of the glass. The coating area was trimmed to 1.0 cm2. The $TiO_2$ coated anode was sintered at 450° C. for 30 minutes, cooled to about 80° C. and dropped into a dye solution containing 0.3 mM of selected dye and 0.3 mM chenodeoxycholic acid in 1:1 acetonitrile/t-butanol (v/v) solvent mixture. The anodes were kept in dye solution overnight, rinsed with acetonitrile and air dried in the dark. The dye sensitized anode was sandwiched with electrochemically deposited PEDOT catalyst on a FTO coated glass slide using Surlyn (Meltonix 1170-60PF from Solaronix, Switzerland) hot melt adhesive window by hot pressing at 125° C. for 45 seconds. A copper redox electrolyte solution consisting of 200 mM bis(6,6'-dimethyl-2,2'-bipyridine) copper (I) bis(trifluorosulfon)imide, 50 mM bis(6,6'-dimethyl-2,2'-bipyridine) copper (II) bis(trifluorosulfon)imide, 100 mM of lithium bis(trifluorosulfon)imide and 0.5 M 4-(t-butyl)pyridine in acetonitrile was injected between anode and cathode using a pinhole on the cathode. The pinhole was sealed using a surlyn/glass cover and a heat sealing process. A conductive silver paint was applied on the contact areas of anode and cathode and dried to form an electrical contact. Two cells were fabricated for each dye (denoted as "cell 1" and "cell 2"). The photovoltaic performance of the fabricated cells were measured under AM 1.5 conditions (1.5 atm) at a light intensity of 97 $mW/cm^2$. The solar performance of fabricated solar cells was characterized using open circuit voltage ($V_{oc}$ in mV), short circuit current density ($J_{sc}$ in milliamperes/square centimeter), fill factor and overall solar conversion efficiency (in %) and shown in Table 1. The fill factor (FF) is defined as the ratio of the maximum power from the solar cell to the product of $V_{oc}$ and $J_{sc}$.

TABLE 1

Photovoltaic characteristics of set 1 dye sensitized solar cells under 1 sun (AM 1.5) irradiation conditions

| Solar dye used in making cell | Cell Size ($cm^2$) | $V_{oc}$ (mV) | $J_{sc}$ ($mA/cm^2$) | FF | Efficiency (%) |
|---|---|---|---|---|---|
| BC-154 Cell 1 | 0.60 | 706.32 | 0.39 | 0.571 | 0.158 |
| BC-154 Cell 2 | 0.60 | 820.22 | 0.32 | 0.499 | 0.132 |
| WBI-PC-174 Cell 1 | 0.60 | 679.55 | 0.45 | 0.570 | 0.176 |
| WBI-PC-174 Cell 2 | 0.60 | 655.38 | 0.34 | 0.542 | 0.122 |
| BC-175 Cell 1 | 0.50 | 916.41 | 4.59 | 0.499 | 2.111 |
| BC-175 Cell 2 | 0.60 | 918.04 | 4.86 | 0.461 | 2.069 |
| WBI-PC-64 cell 1 | 0.60 | 975.64 | 7.54 | 0.438 | 3.241 |
| WBI-PC-64 cell 2 | 0.60 | 987.07 | 7.11 | 0.434 | 3.061 |
| WBI-PC-63 cell 1 | 0.60 | 1013.20 | 6.69 | 0.547 | 3.730 |
| WBI-PC-63 cell 2 | 0.60 | 1018.54 | 6.81 | 0.531 | 3.699 |

Example 20

Solar Cells Made Using Solar Cell Dyes—Set 2

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of $TiO_2$ (AEROXIDE® $TiO_2$ P 25, particle size of 21±5 nm, Evonik Industries, Essen, DE) and 5% by weight of poly (4-vinyl pyridine) was prepared and blade coated (6-8 microns thick) on the FTO coated side of the glass. The coating area was trimmed to about 1.0 cm2. The $TiO_2$ coated anode was sintered at 450° C. for 30 minutes, cooled to about 80° C. and dropped into a dye solution containing 0.3 mM of selected dye and 0.3 mM chenodeoxycholic acid in 1:1 acetonitrile/t-butanol (v/v) solvent mixture. The anodes were kept in dye solution overnight, rinsed with acetonitrile and air dried in the dark. The dye sensitized anode was sandwiched with electrochemically deposited PEDOT catalyst on a FTO coated glass slide using Surlyn (Meltonix 1170-60PF from Solaronix, Switzerland) hot melt adhesive window by hot pressing at 125° C. for 45 seconds. A copper redox electrolyte solution consisting of 200 mM bis(6,6'-dimethyl-2,2'-bipyridine) copper (I) bis(trifluorosulfon)imide, 50 mM bis(6,6'-dimethyl-2,2'-bipyridine) copper (II) bis(trifluorosulfon)imide, 100 mM of lithium bis(trifluorosulfon)imide and 0.5 M 4-(t-butyl)pyridine in acetonitrile was injected between anode and cathode using a pinhole on the cathode. The pinhole was sealed using a surlyn/glass cover and a heat sealing process. A conductive silver paint was applied on the contact areas of anode and cathode and dried to form an electrical contact. Two cells were fabricated for each dye (denoted as "cell 1" and "cell 2"). The photovoltaic performance of the fabricated cells were measured under AM 1.5 (1.5 atm) conditions at a light intensity of 97 mW/cm². The solar performance of fabricated solar cells was characterized using open circuit voltage ($V_{oc}$ in mV), short circuit current density ($J_{sc}$ in milliamperes/square centimeter), fill factor and overall solar conversion efficiency (in %) and shown in Table 2. The fill factor (FF) is defined as the ratio of the maximum power from the solar cell to the product of $V_{oc}$ and $J_{sc}$.

TABLE 2

Photovoltaic characteristics of set 2 dye sensitized solar cells using 6,6'-dimethyl-2,2'-bipyridine ligand based copper redox electrolyte under 1 sun (AM 1.5) irradiation conditions

| Dye | $V_{oc}$ (mV) | $J_{sc}$ (mA/cm²) | FF | Efficiency |
|---|---|---|---|---|
| WBI-PC-63 cell 1 | 1013.32 | 6.29 | 0.554 | 3.550 |
| WBI-PC-63 cell 2 | 1043.88 | 7.89 | 0.569 | 4.708 |
| WBI-PC-78 cell 1 | 943.79 | 4.42 | 0.588 | 2.466 |
| WBI-PC-78 cell 2 | 953.73 | 4.57 | 0.579 | 2.537 |
| WBI-PC-81 cell 1 | 1021.75 | 6.26 | 0.572 | 3.673 |
| WBI-PC-81 cell 2 | 992.13 | 7.11 | 0.574 | 4.066 |
| BC-146 cell 1 | 965.10 | 4.90 | 0.625 | 2.971 |
| BC-146 cell 2 | 930.88 | 4.39 | 0.630 | 2.589 |
| BC148 cell 1 | 1005.13 | 5.47 | 0.596 | 3.291 |
| BC148 cell 2 | 963.31 | 5.44 | 0.602 | 3.172 |
| BC-149 cell 1 | 1035.33 | 6.46 | 0.573 | 3.850 |
| BC-149 cell 2 | 1014.71 | 7.25 | 0.579 | 4.277 |
| BC-166 cell 1 | 842.81 | 2.71 | 0.640 | 1.469 |
| BC-166 cell 2 | 847.97 | 2.69 | 0.618 | 1.414 |
| BC-173 cell 1 | 890.33 | 4.49 | 0.614 | 2.465 |
| BC-173 cell 2 | 896.27 | 4.49 | 0.593 | 2.400 |

Example 21

Solar Cells Made Using Solar Cell Dyes—Set 3

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of $TiO_2$ (AEROXIDE® $TiO_2$ P 25, particle size of 21±5 nm, Evonik Industries, Essen, DE) and 5% by weight of poly (4-vinyl pyridine) was prepared and blade coated (6-8 microns thick) on the FTO coated side of the glass. The coating area was trimmed to 1.0 cm2. The $TiO_2$ coated anode was sintered at 450° C. for 30 minutes, cooled to about 80° C. and dropped into a dye solution containing 0.3 mM of selected dye and 0.3 mM chenodeoxycholic acid in 1:1 acetonitrile/t-butanol (v/v) solvent mixture. The anodes were kept in dye solution overnight, rinsed with acetonitrile and air dried in the dark. The dye sensitized anode was sandwiched with electrochemically deposited PEDOT catalyst on a FTO coated glass slide using Surlyn (Meltonix 1170-60PF from Solaronix, Switzerland) hot melt adhesive window by hot pressing at 125° C. for 45 seconds. A copper redox electrolyte solution consisting of 200 mM bis(2,9-dimethyl-1,10-phenanthroline) copper (I) bis(trifluorosulfo-n)imide, 50 mM bis(2,9-dimethyl-1,10-phenanthroline) copper (II) bis(trifluorosulfon)imide, 100 mM of lithium bis (trifluorosulfon)imide and 0.5 M 4-(tertiarybutyl)pyridine in acetonitrile was injected between anode and cathode using a pinhole on the cathode. The pinhole was sealed using a surlyn/glass cover and a heat sealing process. A conductive silver paint was applied on the contact areas of anode and cathode and dried to form an electrical contact. The photovoltaic performance of the fabricated cells were measured under AM 1.5 (1.5 atm) conditions at a light intensity of 97 mW/cm2. The solar performance of fabricated solar cells was characterized using open circuit voltage ($V_{oc}$ in mV), short circuit current density ($J_{sc}$ in milliamperes/square centimeter), fill factor and over all solar conversion efficiency (in %) and shown in Table 3. The fill factor (FF) is defined as the ratio of the maximum power from the solar cell to the product of $V_{oc}$ and $J_{sc}$.

TABLE 3

Photovoltaic characteristics of set 3 dye sensitized solar cells using 2,9-dimethyl-1,10-phenanthroline ligand based copper redox electrolyte under 1 sun (AM 1.5) irradiation conditions

| Dye | $V_{oc}$ (mV) | $J_{sc}$ (mA/cm²) | FF | Efficiency |
|---|---|---|---|---|
| WBI-PC-63 | 1053.07 | 5.96 | 0.651 | 4.102 |
| WBI-PC-78 | 954.63 | 2.32 | 0.672 | 1.498 |
| WBI-PC-81 | 1023.62 | 4.89 | 0.665 | 3.347 |
| BC-146 | 960.02 | 3.65 | 0.707 | 2.491 |
| BC148 | 1035.40 | 5.62 | 0.675 | 3.945 |
| BC-149 | 1076.35 | 6.52 | 0.682 | 4.808 |
| BC-166 | 872.23 | 1.55 | 0.653 | 0.888 |
| BC-173 | 860.07 | 2.66 | 0.367 | 0.844 |

Example 22

Electrochemical Characterization of Solar Dyes

Fluorine-doped tin oxide (FTO) coated glasses were cut into 2 cm×2 cm size and cleaned by washing with successive 1% aqueous Triton X-100 solution, deionized (DI) water, and isopropanol. After drying at room temperature, the cleaned FTO glasses were treated with Corona discharge (~13000V) for approximately 20 seconds on the conducting side. An aqueous dispersion containing 20% by weight of $TiO_2$ (AEROXIDE® $TiO_2$ P 25, particle size of 21±5 nm, Evonik Industries, Essen, DE) and 5% by weight of poly (4-vinyl pyridine) was prepared and blade coated (6-8 microns thick) on the FTO coated side of the glass. The coating area was trimmed to about 1.0 cm². The $TiO_2$ coated anode was sintered at 450° C. for 30 minutes, cooled to about 80° C. and dropped into a dye solution containing 0.3 mM of selected dye and 0.3 mM chenodeoxycholic acid in 1:1 acetonitrile/t-butanol (v/v) solvent mixture. The anodes were kept in dye solution overnight, rinsed with acetonitrile and air dried in the dark. CV measurements were then performed using selected dye-sensitized, titanium dioxide-coated electrodes in a three-electrode configuration (using a Pt wire counter electrode and Ag/AgNO₃ reference electrode) in 2 mM ferrocene and 100 mM tetrabutylammonium hexafluorophosphate (TBAHFP) in acetonitrile solution. The sweep rate used was 10 mV/s. Table 4 shows reduction, oxidation and redox potentials of the dyes.

TABLE 4

| Redox potentials of selected dyes | | | |
|---|---|---|---|
| Dye Sample | $E_{ox}$ vs NHE in mV | $E_{red}$ vs NHE in mV | $E_{1/2}$ vs NHE in mV |
| Commercial dye D35 from Dyenamo | 1249 | 1016 | 1132 |
| Commercial dye XY1b from Dyenamo | 1393 | 963 | 1178 |
| BC-064 | 1278 | 1106 | 1192 |
| WBI-PC-078 | 1331 | 1063 | 1197 |
| WBI-PC-081 | 1441 | 983 | 1212 |
| BC-146 | 1391 | 1083 | 1237 |
| BC-148 | 1312 | 1009 | 1161 |
| BC-149 | 1397 | 1086 | 1242 |
| BC-164 | 1278 | 1106 | 1192 |
| BC-173 | 1144 | 991 | 1068 |
| BC-175 | 1201 | 1025 | 1113 |

Example 23

Absorption Characteristics of Selected Solar Dyes

Selected dyes were dissolved in tetrahydrofuran in known concentrations (5 to 20 μM) and their absorption profiles were measured from 300 to 800 nm using a quartz cuvette with 1 cm path length using a UV-visible spectrophotometer (Agilent Technologies, Cary 60 UV-vis). Table 5 shows absorption maxima and molar extinction coefficients at the absorption maximum of selected dyes.

TABLE 5

| Absorption maxima and molar extinction coefficients of dyes | | | |
|---|---|---|---|
| Dye | MW (g/mol) | Absorption maximum in nm $\lambda_{max}$ | Molar extinction coefficient $\varepsilon_{max}$ (M$^{-1}$ cm$^{-1}$) |
| BOD-4 | 614.77 | 469 | 35148 |
| Commerical Dye D35 | 863.11 | 476 | 29737 |
| WBI-PC-78 | 558.62 | 434 | 30359 |
| WBI-PC-81 | 406.43 | 455 | 26416 |
| BC-146 | 380.4 | 462 | 25148 |
| BC-149 | 456.5 | 428 | 30303 |
| BC-154 | 437.5 | 454 | 33866 |
| BC165 | 425.44 | 400 | 34979 |
| BC-166 | 372.42 | 417 | 13996 |
| BC169 | 374.4 | 415 | 29447 |
| BC172 | 387.44 | 421 | 14794 |
| BC-173 | 360.41 | 448 | 35909 |
| WBI-PC-174 | 551.73 | 438 | 27363 |
| BC-175 | 394.43 | 430 | 31059 |

TABLE 5-continued

Commercial Dyenamo (Stockholm, SE) dye structures

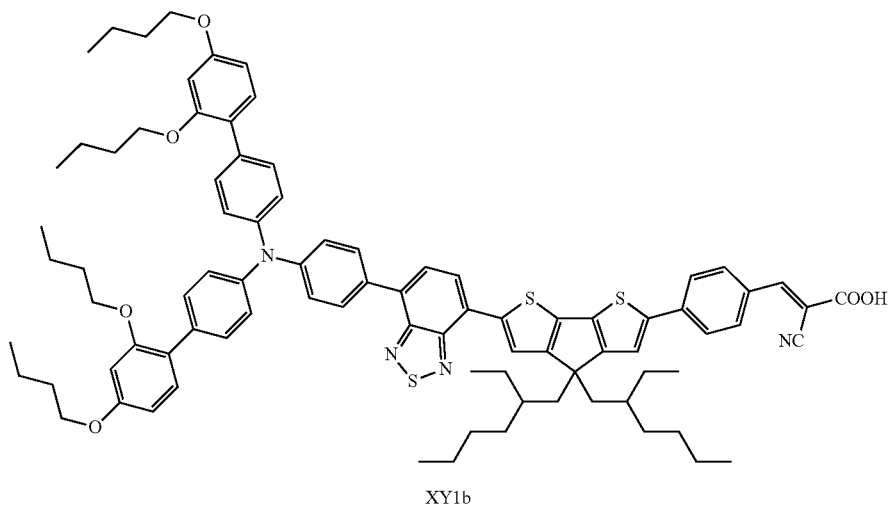 [SMILES: CCCCOc1ccc(-c2ccc(N(c3ccc(-c4ccc(OCCCC)cc4OCCCC)cc3)c3ccc(-c4ccc(-c5cc6c(s5)-c5sc(-c7ccc(/C=C(\C#N)C(=O)O)cc7)cc5C6(CC(CC)CCCC)CC(CC)CCCC)c5nsnc45)cc3)cc2)c(OCCCC)c1]

XY1b

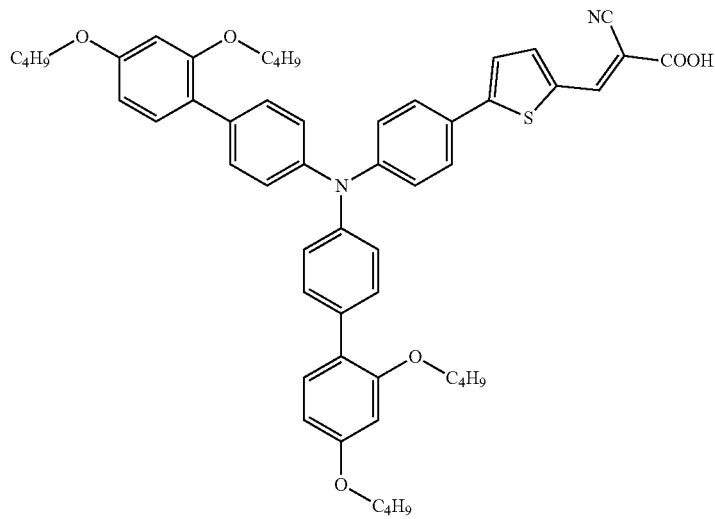

Dyenamo Orange D35

What is claimed is:

1. A solar cell dye for use in a DSSC, wherein the solar cell dye is a compound of formula I:

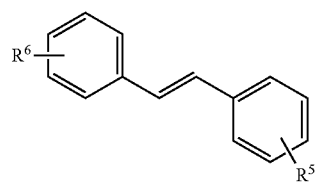

(I)

wherein
R$^6$ is selected from the group consisting of —NR$^3$R$^4$, —R$^3$, —OR$^3$ and halo;
R$^5$ is —(CR=CR—)$_n$(CR=CR$^2$—)R$^1$;
n is an integer from 0 to 10;
R$^1$ and R$^2$ are independently selected from the group consisting of —H, —CN, —COOR, CONHR, CON(H)OR, —SO$_3$R, —SO$_2$R —OSO$_3$R, —PO$_3$HR, and —OPO$_3$HR, further wherein at least one of R$^1$ and R$^2$ is not —H;
each R is independently selected from —H and C$_{1-6}$ linear or branched alkyl; and
R$^3$ and R$^4$ are independently selected from the group consisting of H, substituted or unsubstituted linear or branched C$_1$-C$_{10}$ alkyl, substituted or unsubstituted phenyl, substituted or unsubstituted C$_6$-C$_{10}$ aryl, substituted or unsubstituted C$_5$-C$_{10}$ heteroaryl, substituted or unsubstituted C$_5$-C$_{10}$ cycloalkyl, and substituted or unsubstituted C$_5$-C$_{10}$ heterocycloalkyl; or R$^3$ and R$^4$ attached to their N together form a ring that is substituted or unsubstituted C$_5$-C$_{10}$ heterocycloalkyl, provided that
if n=0, and R$^3$ and R$^4$ are both: (a) H; (b) substituted or unsubstituted linear or branched C$_1$-C$_{10}$ alkyl; or (c) substituted or unsubstituted phenyl or C$_6$-C$_{10}$ aryl, then R$^1$ and R$^2$ are not both selected from the group consisting of —H, —CN, —COOR, and —CONHR.

2. The dye of claim 1 having the formula II:

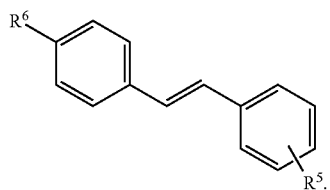

3. The dye of claim 1 having the formula III:

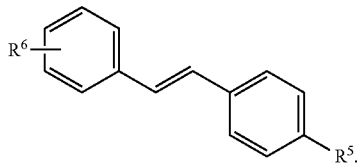

4. The dye of claim 1 having the formula IV:

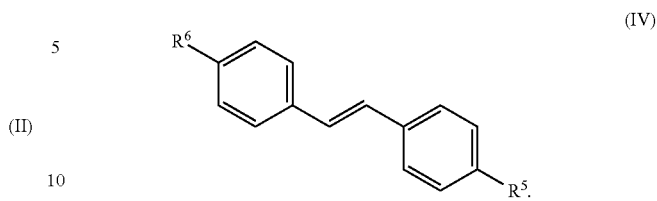

5. The dye of claim 4 wherein $R^6$ is —$NR^3R^4$.

6. The dye of claim 5 wherein $R^6$ is selected from the group consisting of diethylamino, diphenylamino, methyl(phenyl)amino, cyclohexyl(methyl)amino, bis(4-methoxyphenyl)amino, bis(4-(tert-butyl)phenyl)amino, di(pyridin-2-yl)amino, di(pyridin-3-yl)amino, di(pyridin-4-yl)amino, piperidin-1-yl, 4-methylpiperazin-1-yl, 4-phenylpiperazin-1-yl, pyrrolidin-1-yl, and morpholino.

7. The dye of claim 5, wherein $R^6$ is —$R^3$ or —$OR^3$.

8. The dye of claim 7 wherein $R^6$ is selected from the group consisting of 3',4'-dimethoxyphenyl, Cert-butyl, phenyoxy, and methoxy.

9. The dye of claim 5 wherein $R^6$ is halo.

10. The dye of claim 9 wherein $R^6$ is bromo.

11. The dye of claim 5 wherein $R^3$ and $R^4$ are substituted or unsubstituted phenyl.

12. The dye of claim 4 wherein $R^1$ and $R^2$ together are —CN and —COOH.

13. A dye sensitized solar cell comprising the solar cell dye of claim 1.

14. A method of making a DSSC comprising the step of incorporating the solar cell dye of claim 1 into the DSSC.

* * * * *